(12) United States Patent
Zuk, Jr.

(10) Patent No.: US 7,270,757 B1
(45) Date of Patent: *Sep. 18, 2007

(54) HIGH CAPACITY GRAVITY FEED FILTER FOR FILTERING BLOOD AND BLOOD PRODUCTS

(75) Inventor: Peter Zuk, Jr., Harvard, MA (US)

(73) Assignee: Hemerus Medical LLC, St. Paul, MN (US)

(*) Notice: Subject to any disclaimer, the term of this patent is extended or adjusted under 35 U.S.C. 154(b) by 264 days.

This patent is subject to a terminal disclaimer.

(21) Appl. No.: 10/693,757

(22) Filed: Oct. 24, 2003

Related U.S. Application Data

(63) Continuation-in-part of application No. 09/818,108, filed on Mar. 27, 2001, now Pat. No. 6,660,171.

(60) Provisional application No. 60/192,733, filed on Mar. 27, 2000.

(51) Int. Cl.
*B01D 37/00* (2006.01)
*B01D 29/00* (2006.01)

(52) U.S. Cl. .................. 210/767; 210/435; 210/455; 210/456

(58) Field of Classification Search ............. 210/650, 210/767, 321.6, 433.1, 435, 446, 455, 456, 210/477

See application file for complete search history.

(56) References Cited

U.S. PATENT DOCUMENTS

| | | | | |
|---|---|---|---|---|
| 4,304,670 A | * | 12/1981 | Watanabe et al. | 210/446 |
| 4,422,939 A | * | 12/1983 | Sharp et al. | 210/445 |
| 4,963,260 A | * | 10/1990 | Naoi et al. | 210/446 |
| 5,439,587 A | * | 8/1995 | Stankowski et al. | 210/321.64 |
| 5,622,626 A | * | 4/1997 | Matkovich et al. | 210/649 |
| 6,010,633 A | * | 1/2000 | Zuk et al. | 210/767 |
| 6,214,574 B1 | * | 4/2001 | Kopf | 435/41 |
| 6,231,770 B1 | * | 5/2001 | Bormann et al. | 210/767 |
| 6,251,292 B1 | * | 6/2001 | Zuk, Jr. | 210/767 |
| 6,274,055 B1 | * | 8/2001 | Zuk, Jr. | 210/767 |
| 6,660,171 B2 | * | 12/2003 | Zuk, Jr. | 210/767 |

* cited by examiner

*Primary Examiner*—John Kim
(74) *Attorney, Agent, or Firm*—Marshall & Melhorn LLC

(57) ABSTRACT

A high capacity gravity feed filter for filtering blood and blood products or the like includes a body having an inlet port, an outlet port, two filter wells, at least one filter element disposed in each of said filter wells, between the inlet port and outlet port so as to filter liquid which flows into the filtration device via the inlet port. The filter elements divide each of said filter wells into a first chamber and a second chamber. The device allows gases to vent the filtration device through the outlet port. The means may include a through slot located at the top of each of said second chambers. The filtration device allows air therein to be purged downstream into a receiving blood bag without the manipulation of the height of the filtration device or the receiving blood bag.

21 Claims, 38 Drawing Sheets

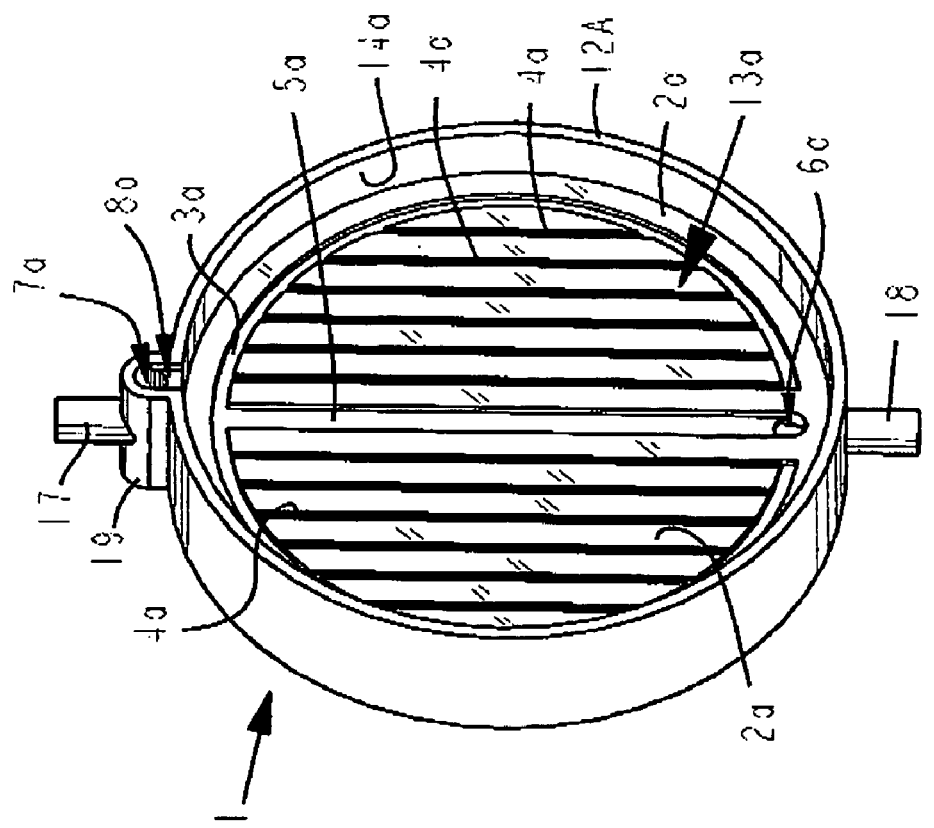
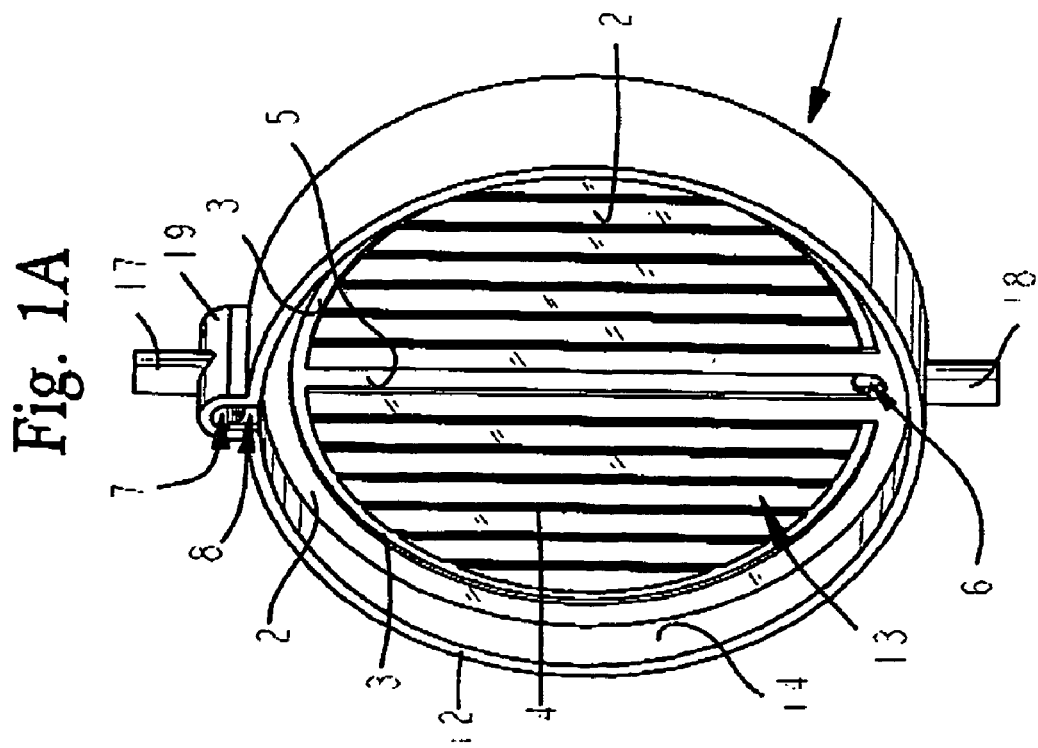

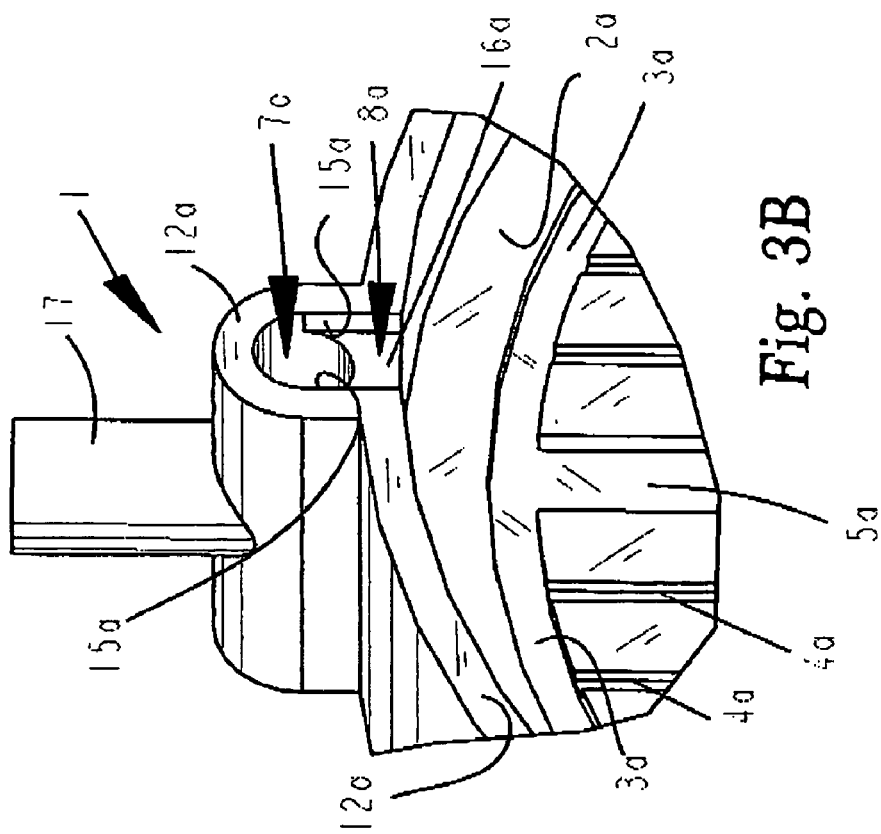
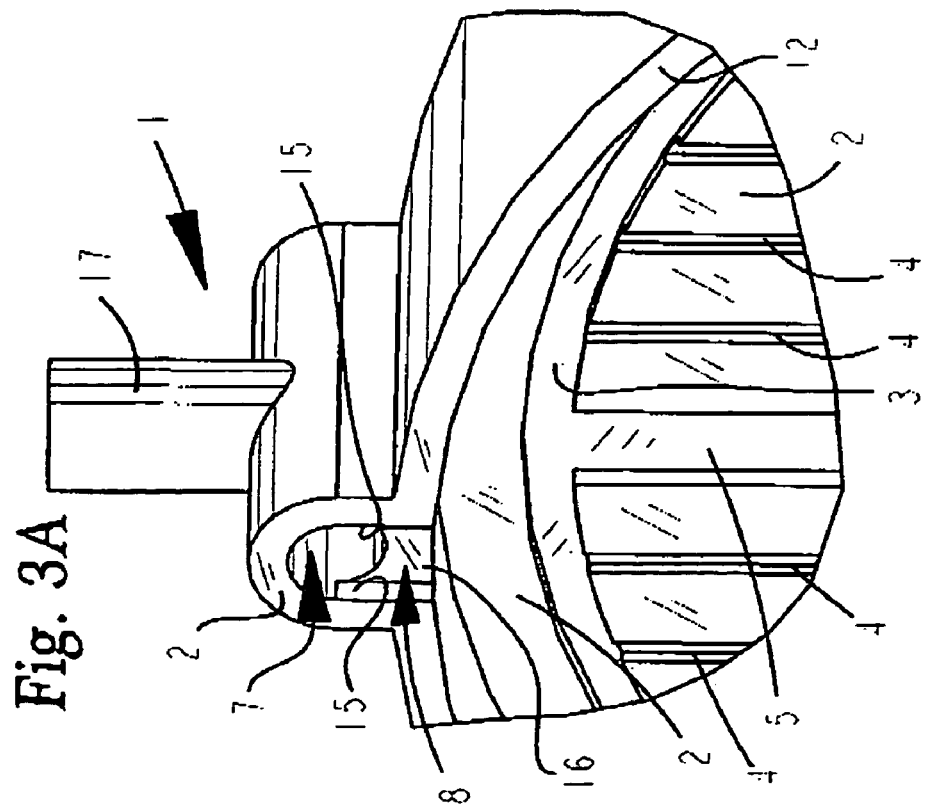

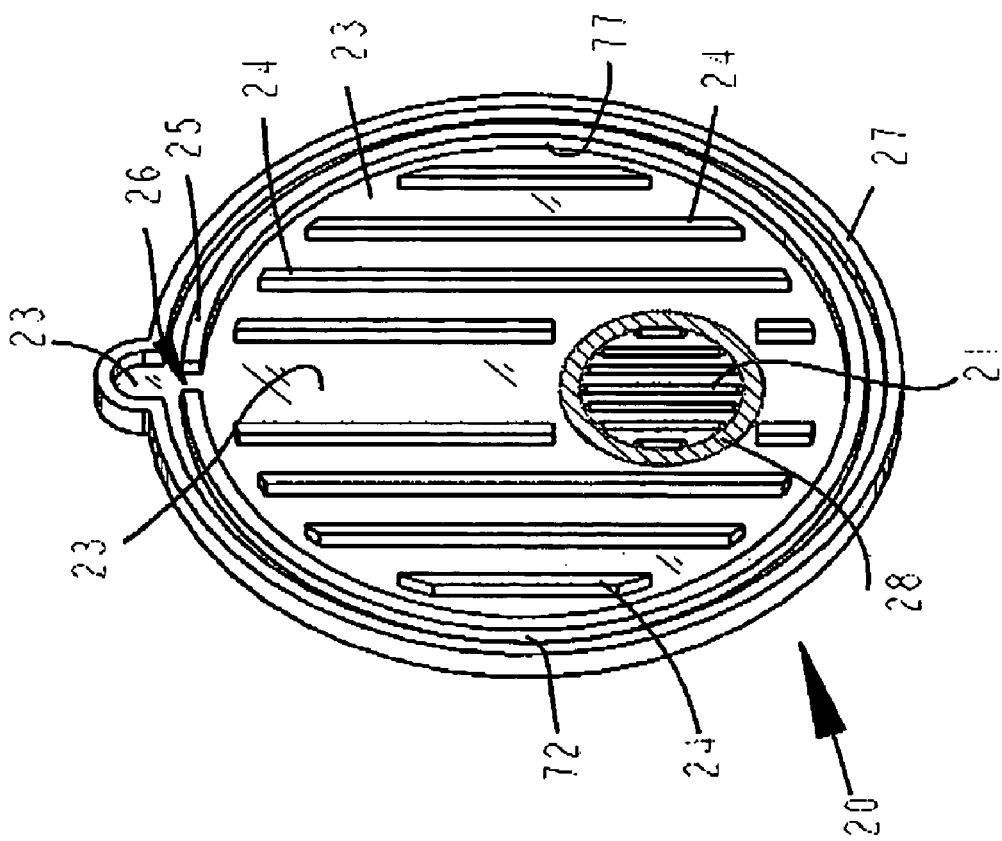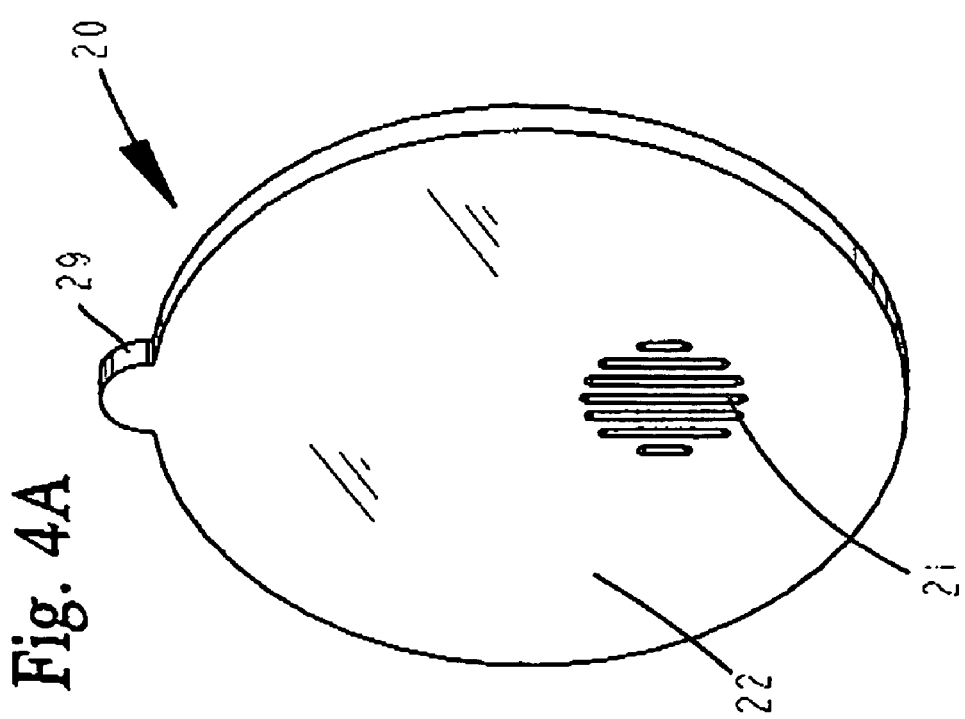

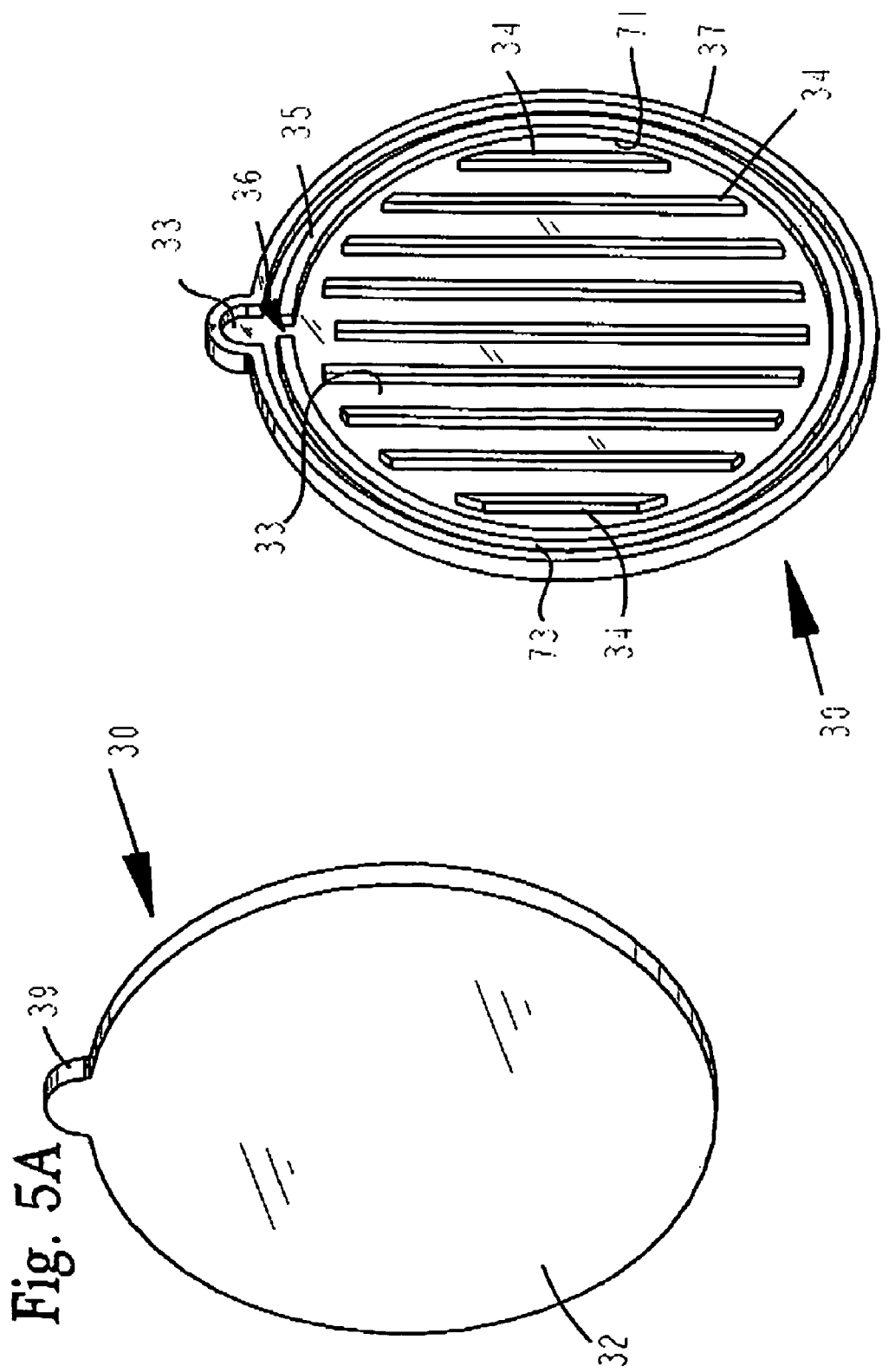

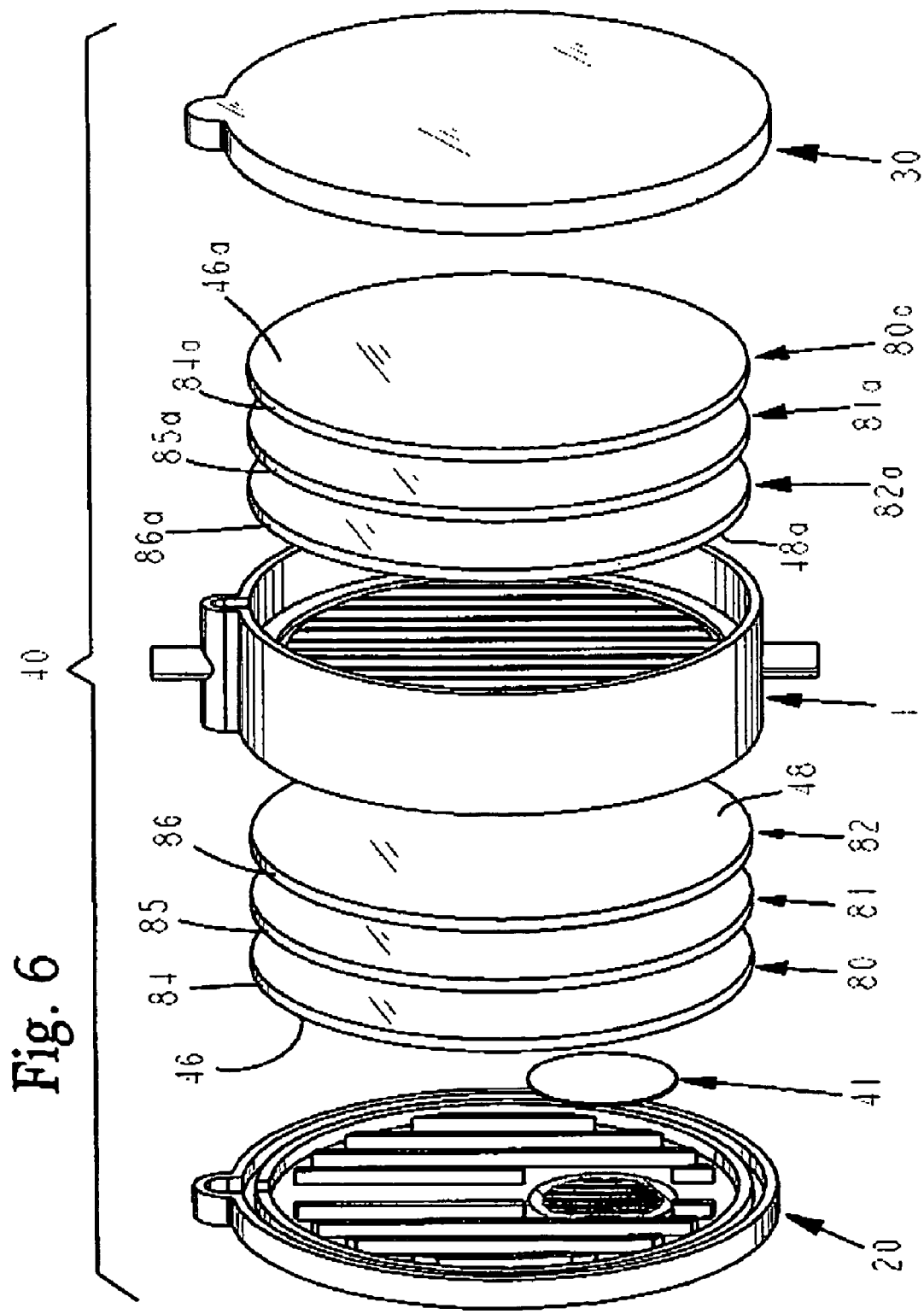

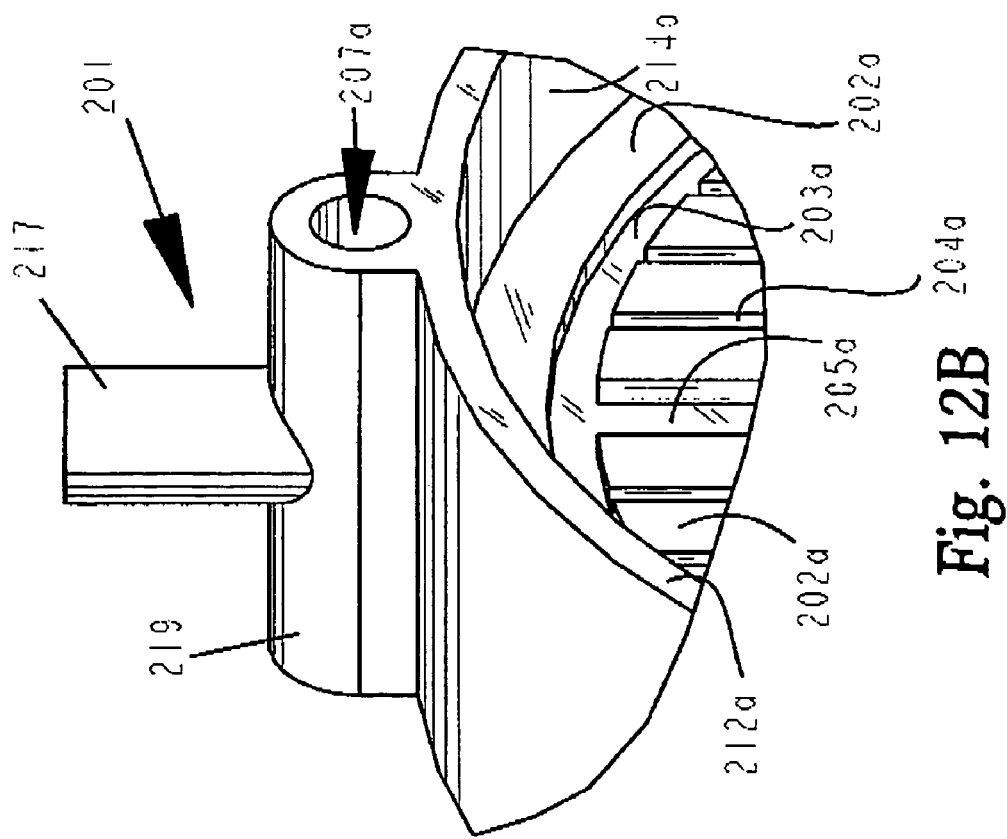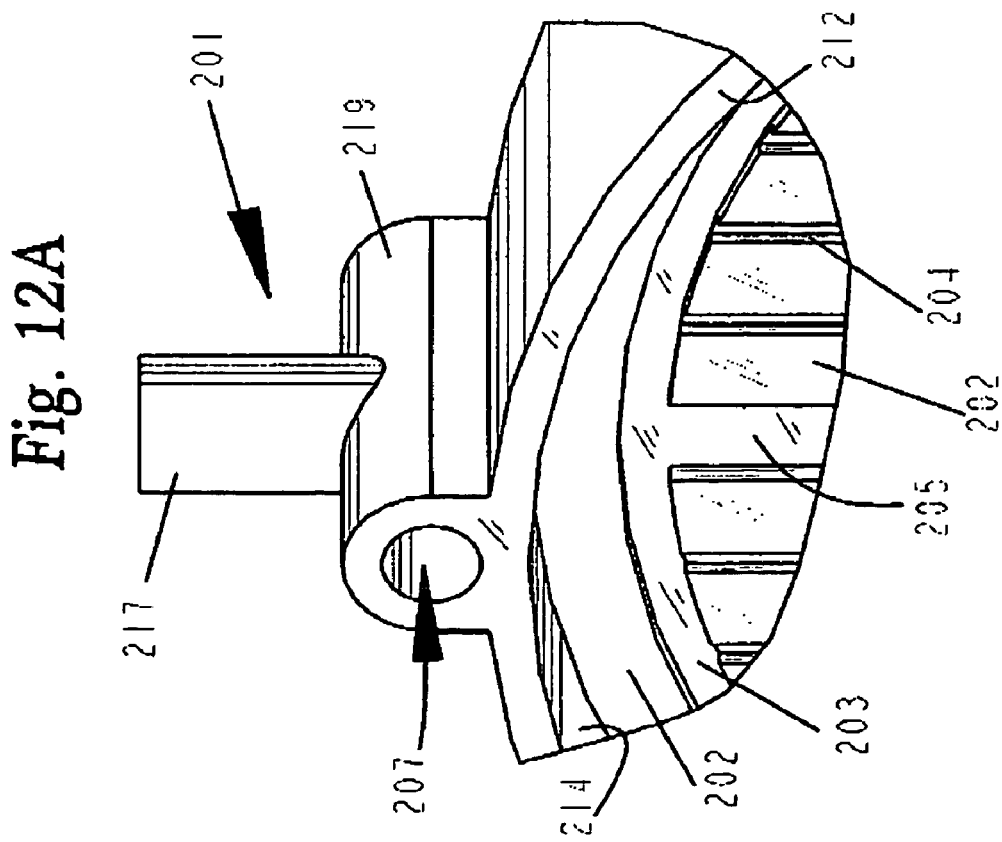

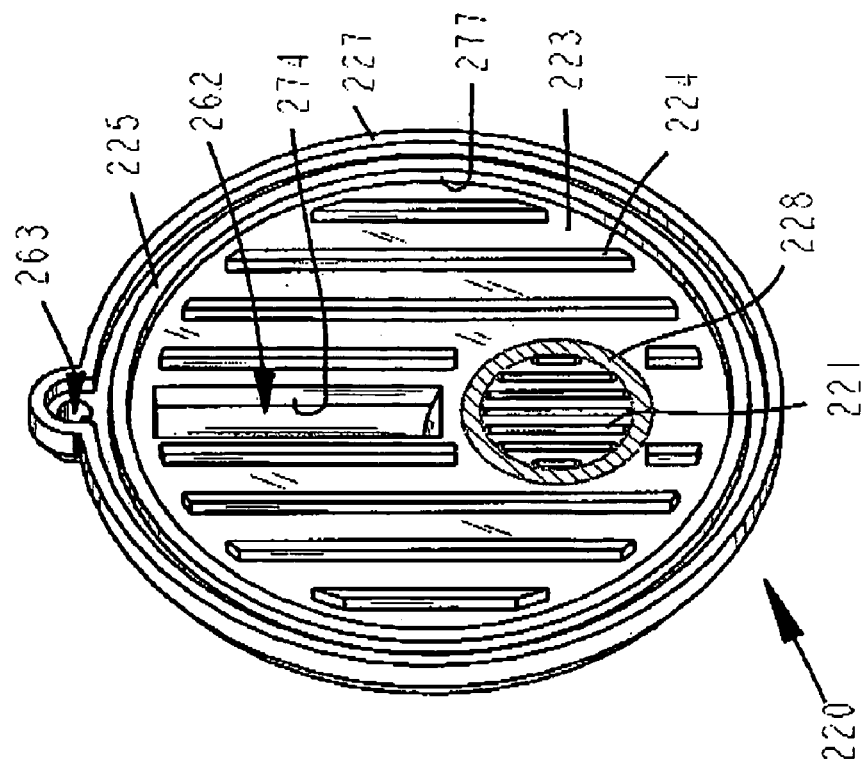
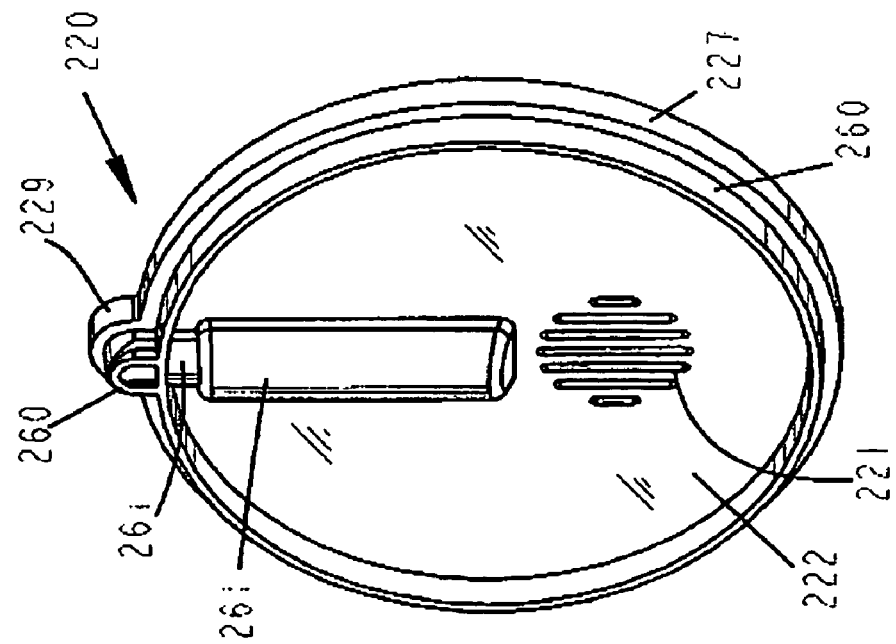

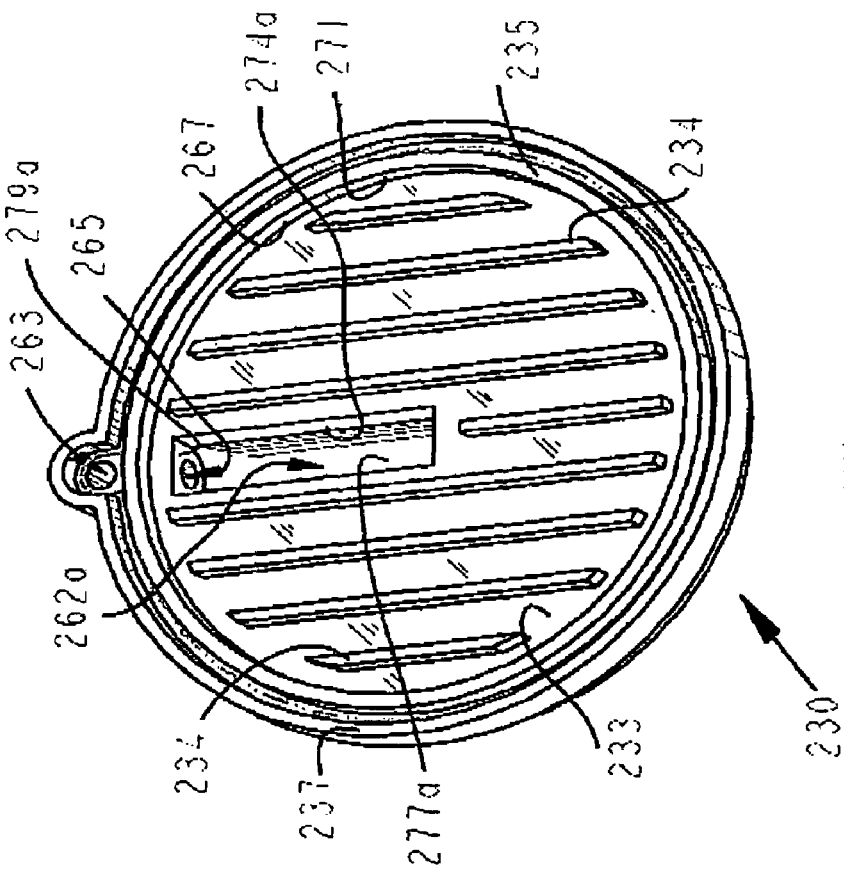
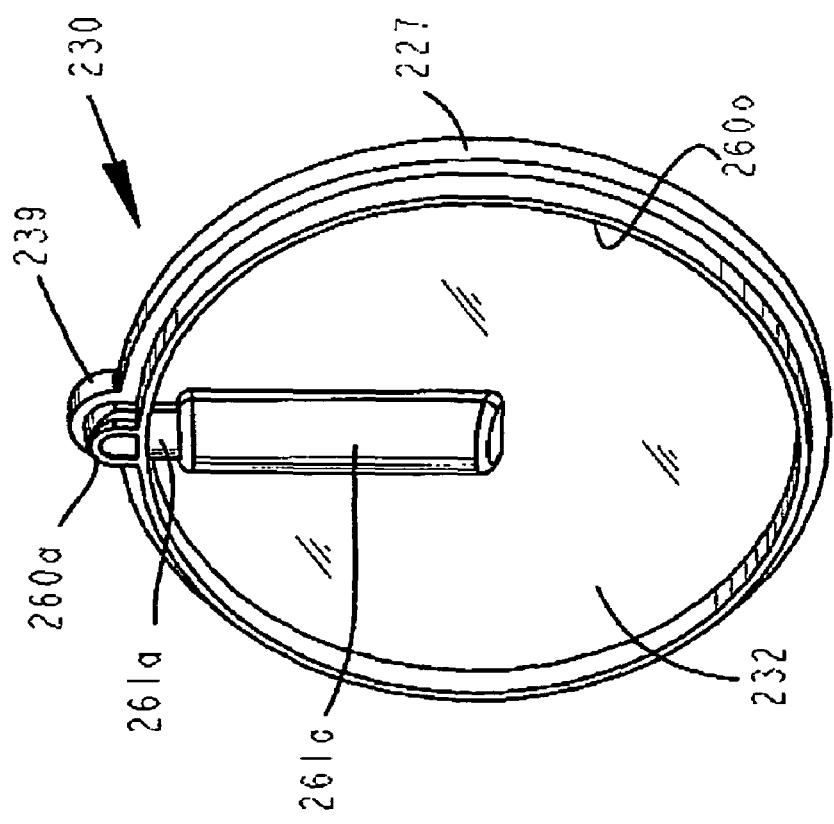

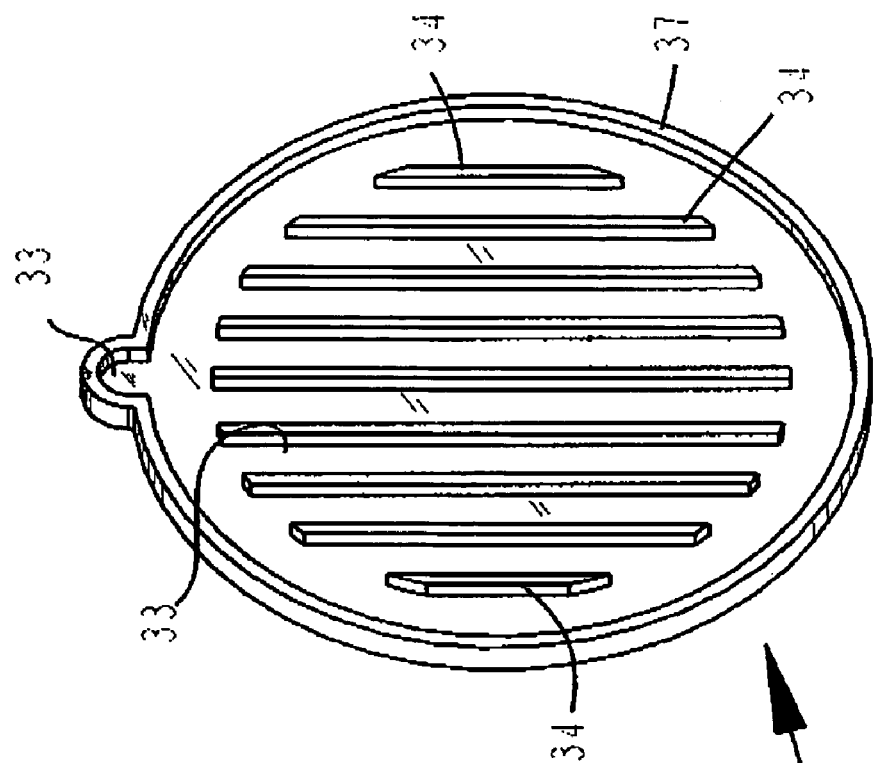
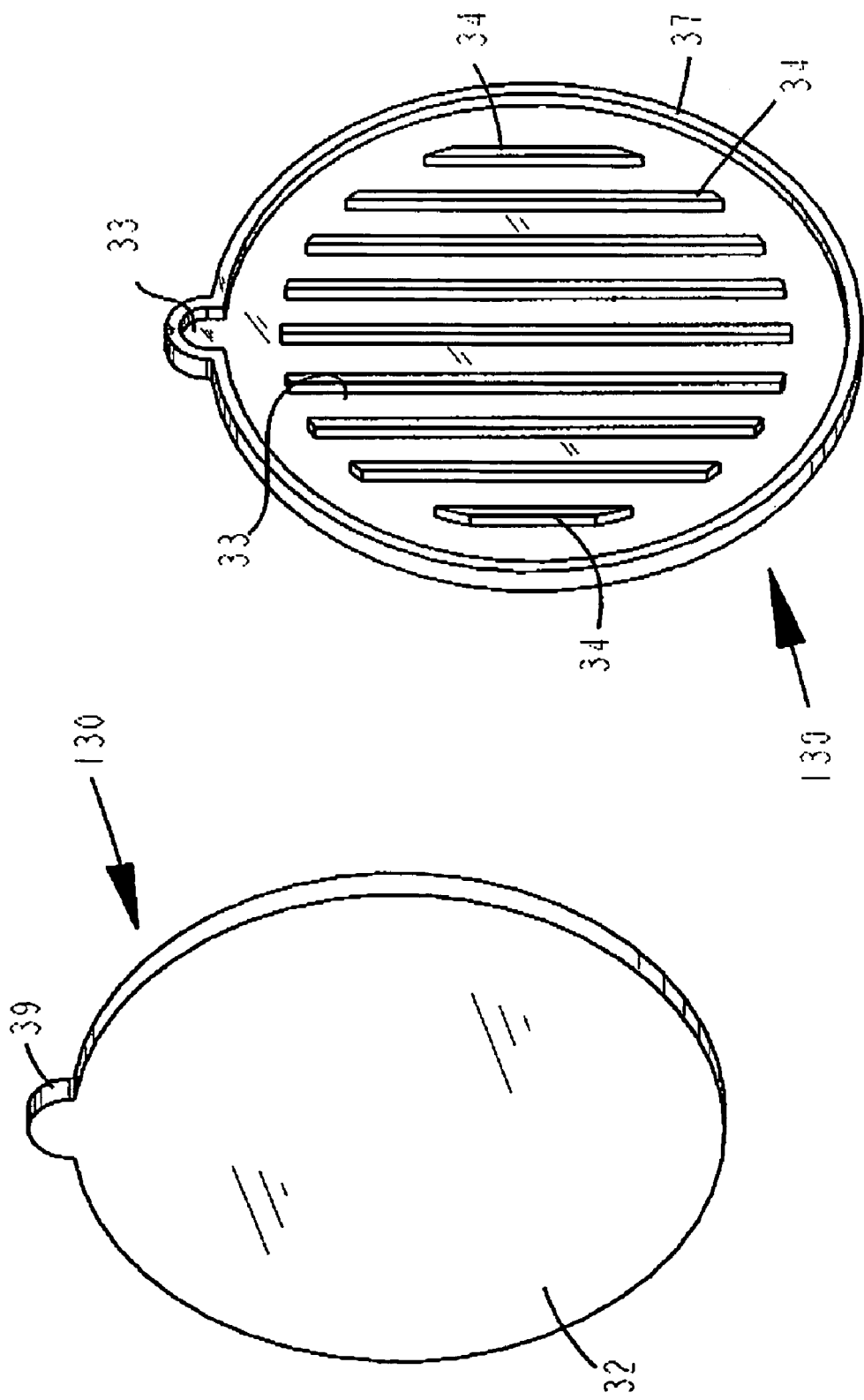

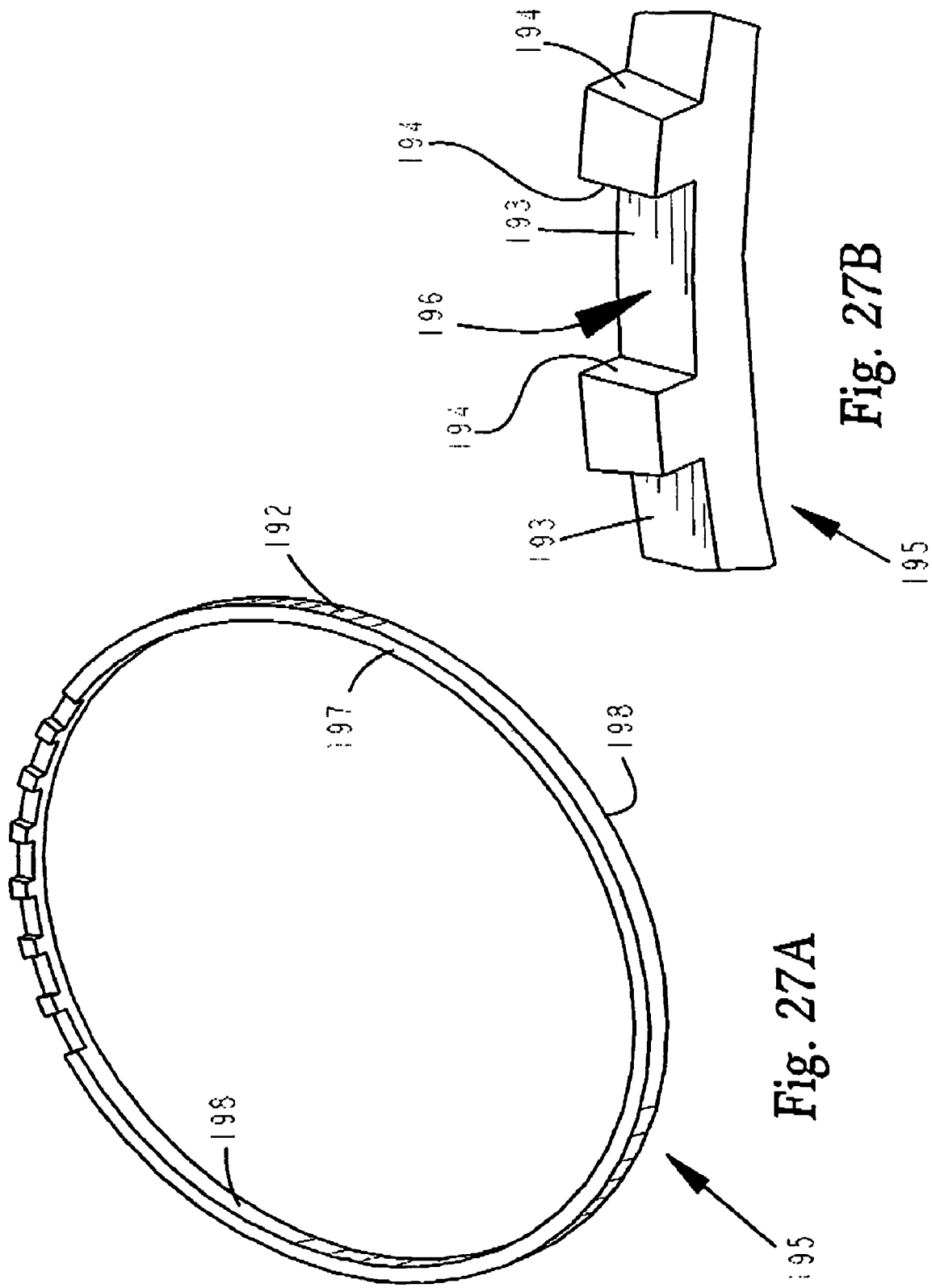

*Fig. 43*
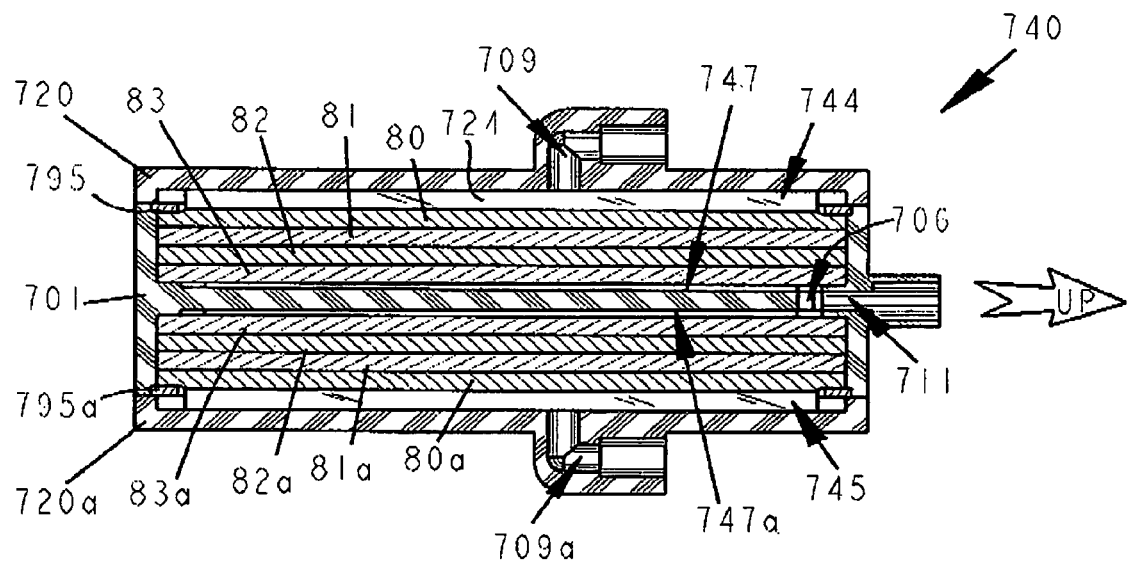
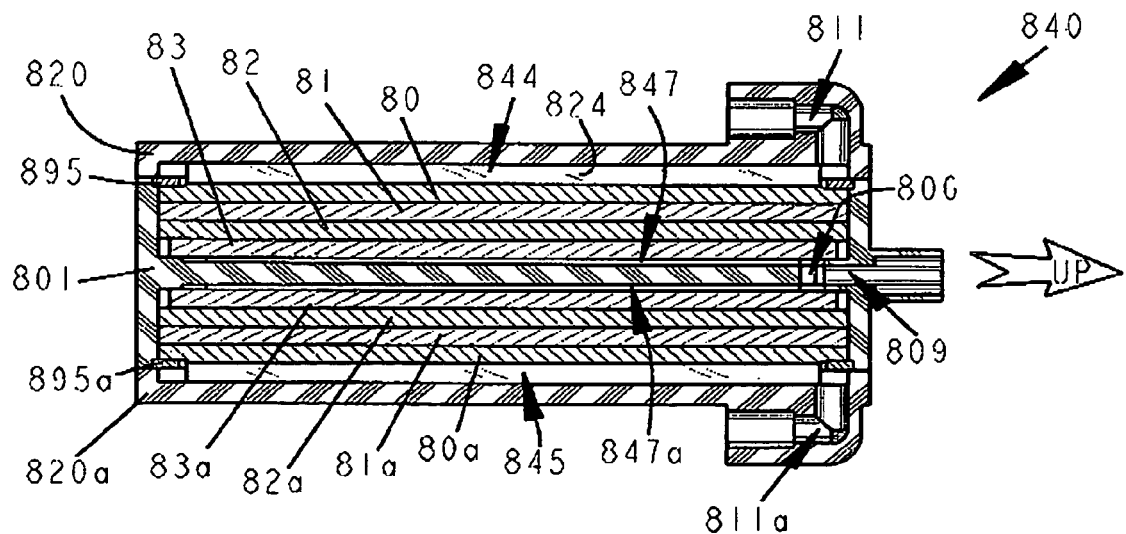
*Fig. 44*

HIGH CAPACITY GRAVITY FEED FILTER FOR FILTERING BLOOD AND BLOOD PRODUCTS

This application is a Continuation In Part of application Ser. No. 09/818,108, filed on Mar. 27, 2001, now U.S. Pat. No. 6,660,171 issued on Dec. 9, 2003, in which applicant claimed priority of Provisional Application No. 60/192,733 filed on Mar. 27, 2000.

BACKGROUND OF THE INVENTION

This invention relates to the filtration field, and more particularly, to an improved gravity feed filtration device for filtering blood and blood products.

There are commercially available gravity filtration devices for filtering blood and blood products. The currently available gravity feed blood filters are capable of filtering a single unit of blood. Furthermore, certain types of blood or blood products foul the currently available devices before a single unit of blood can be filtered.

It is therefore an object of the present invention to provide a gravity feed filtration device capable of filtering any type of blood or blood product, including the removal of leukocytes from blood or blood products and capable of filtering at least two units of blood or blood product.

SUMMARY OF THE INVENTION

The foregoing problems of the prior art are solved, and the objects of the present invention are achieved, by use of a filtration apparatus constructed in accordance with the principles of the present invention.

In accordance with the present invention, the filtration apparatus for the gravity filtration of blood or blood products is divided into two independent filtration chambers. The apparatus contains a common inlet port that is in fluid flow communication with inlet ports of the two independent filtration chambers, and a common outlet port that is in fluid flow communication with outlet ports of the two independent filtration chambers. The apparatus may also contain a means to automatically drain the upstream portion of both of the filtration chambers once the filtration process is complete.

BRIEF DESCRIPTION OF THE DRAWINGS

These and other objects, features and advantages of the invention will be evident from the following detailed description when read in conjunction with the accompanying drawings in which:

FIG. 1A is a front isometric view of the body of the filtration apparatus depicted in FIG. 6;

FIG. 1B is a back isometric view of the body of the filtration apparatus depicted in FIG. 6;

FIG. 3A is a partial front isometric view of the top portion of the body depicted in FIG. 1a;

FIG. 3B is a partial back isometric view of the top portion of the body depicted in FIG. 1b;

FIG. 4A is a front isometric view of the front cover of the filtration apparatus depicted in FIG. 6;

FIG. 4B is a back isometric view of the front cover of the filtration apparatus depicted in FIG. 6;

FIG. 5A is a front isometric view of the back cover of the filtration apparatus depicted in FIG. 6;

FIG. 5B is a back isometric view of the back cover of the filtration apparatus depicted in FIG. 6;

FIG. 6 is an exploded isometric view of the components that comprise the first embodiment of the filtration apparatus, constructed in accordance with the principles of the present invention, usable for the gravity filtration of blood and blood products;

FIG. 12A is a partial front isometric view of the top portion of the body depicted in FIG. 10A;

FIG. 12B is a partial back isometric view of the top portion of the body depicted in FIG. 10B;

FIG. 13A is a front isometric view of the front cover of the filtration apparatus depicted in FIG. 17;

FIG. 13B is a back isometric view of the front cover of the filtration apparatus depicted in FIG. 17;

FIG. 15A is a front isometric view of the back cover of the filtration apparatus depicted in FIG. 17;

FIG. 15B is a back isometric view of the back cover of the filtration apparatus depicted in FIG. 17;

FIG. 24A is a front isometric view of the back cover of the filtration apparatus depicted in FIG. 25;

FIG. 24B is a back isometric view of the back cover of the filtration apparatus depicted in FIG. 25;

FIG. 27A is an isometric view of a filter compression ring of the filtration apparatus depicted in FIG. 25;

FIG. 27B is a partial isometric view of the top portion of the filter compression ring depicted in FIG. 27A;

FIG. 43 is a cross-sectional view of the tenth embodiment of the filtration apparatus, constructed in accordance with the principles of the present invention, usable for the filtration of blood and blood products;

FIG. 44 is a cross-sectional view of the eleventh embodiment of the filtration apparatus, constructed in accordance with the principles of the present invention, usable for the filtration of blood and blood products;

DETAILED DESCRIPTION OF THE PREFERRED EMBODIMENTS

Figure 2:
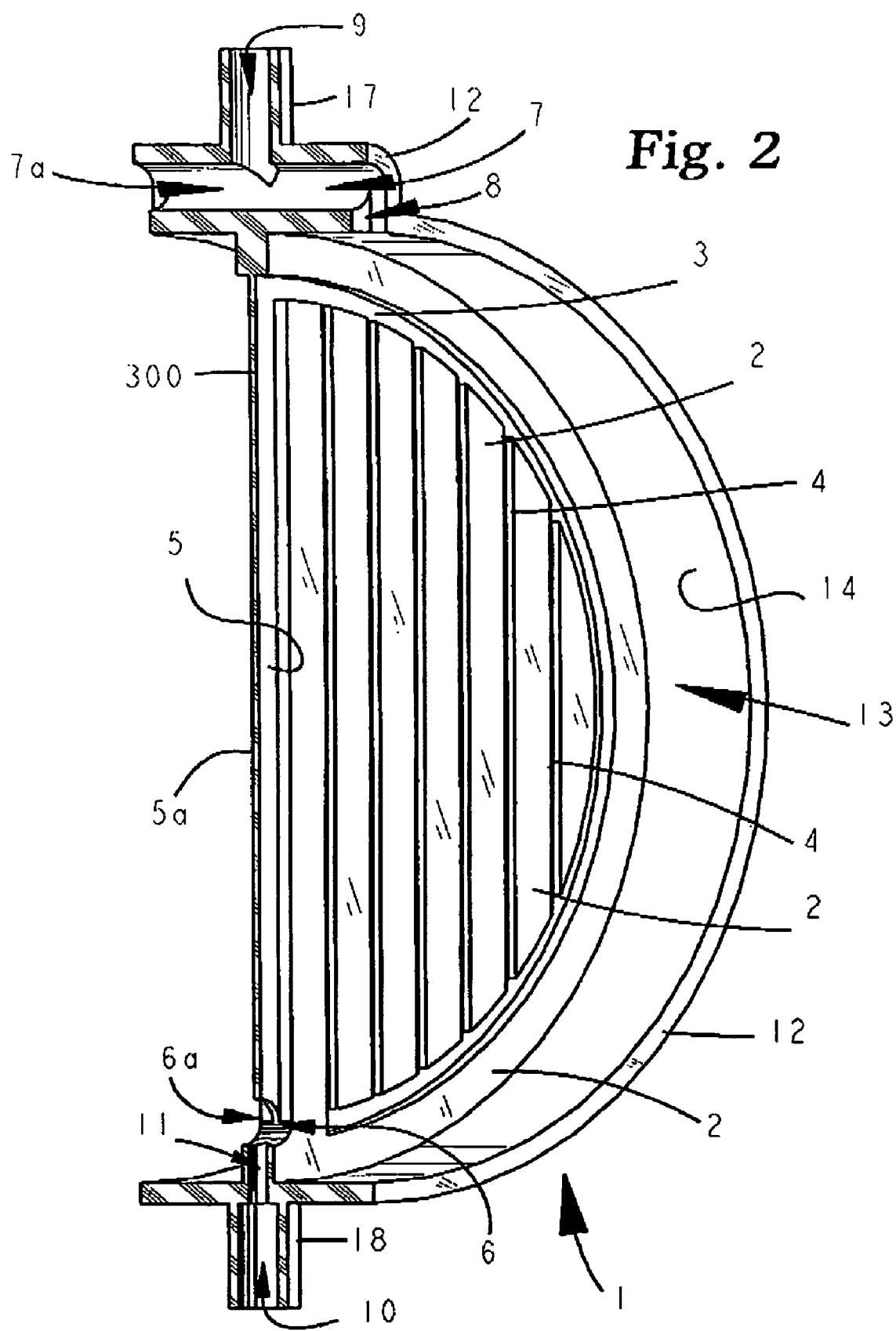
FIG. 2 is an isometric view, having portions thereof removed, of the body of the filtration apparatus depicted in FIG. 6.

Although various embodiments of the filtration device constructed in accordance with the present invention are disclosed herein, each embodiment enables the filtration device to filter more than one unit of blood.

One embodiment of the filtration device constructed in accordance with the principles of the present invention, is shown in FIG. 1A through FIG. 8. Referring to FIG. 6 this embodiment includes the following major components: front cover 20, body 1, back cover 30, filter elements 80, 81, 82, 80a, 81a, and 82a, and hydrophobic vent filter element 41.

FIG. 1A, FIG. 2, and FIG. 3A show the front part of body 1. The front part of body 1 contains a first filter well 13, defined by front flat surface 2 of partition wall 300 and cylindrical surface 14. The front face of partition wall 300 contains side vertical channels 4, circular channel 3, and center vertical channel 5. Preferably circular channel 3 is wider and deeper than side vertical channels 4, and center vertical channel 5 is wider than circular channel 3, and the same depth as circular channel 3. The upper and lower ends of side vertical channels 4 are in fluid flow relation with circular channel 3, and circular channel 3 is in fluid flow relation with center vertical channel 5. Center vertical channel 5 is in fluid flow relation with front outlet port 6. The upper central part of body 1 contains inlet tube socket 17, and cross protrusion 19. Inlet tube socket 17 contains inlet port 9, and cross protrusion 19 contains a cross port, with the front half of the cross port labeled front cross port 7, and the back half of the cross port labeled back cross port 7a. The outer end of cross port 7 contains front inlet channel 8, bounded by side walls 15 and wall 16. The lower central part of body 1 contains outlet tube socket 18. Outlet tube socket 18 contains outlet port 10. Front outlet port 6 is in fluid flow relation with outlet port 10 through link port 11.

FIG. 1B, and FIG. 3B show the back part of body 1. The back part of body 1 contains a second filter well 13a, defined by back flat surface 2a of partition wall 300 and cylindrical surface 14a. The back face of partition wall 300 contains side vertical channels 4a, circular channel 3a, and center vertical channel 5a. Preferably circular channel 3a is wider and deeper than side vertical channels 4a, and center vertical channel 5a is wider than circular channel 3a, and the same depth as circular channel 3a. The upper and lower ends of side vertical channels 4a are in fluid flow relation with circular channel 3a, and circular channel 3a is in fluid flow relation with center vertical channel 5a. Center vertical channel 5a is in fluid flow relation with back outlet port 6a. The upper central part of body 1 contains inlet tube socket 17, and cross protrusion 19. Inlet tube socket 17 contains inlet port 9, and cross protrusion 19 contains a cross port, with the front half of the cross port labeled front cross port 7, and the back half of the cross port labeled back cross port 7a. The outer end of cross port 7a contains back inlet channel 8a, bounded by side walls 15a and wall 16a. The lower central part of body 1 contains outlet tube socket 18. Outlet tube socket 18 contains outlet port 10. Back outlet port 6a is in fluid flow relation with outlet port 10 through link port 11. Front outlet port 6 may be a through hole as shown with the front half labeled front outlet port 6, and the back half labeled back outlet port 6a. As shown in FIGS. 1A through 3B the back part of body 1 is a mirror image of the front part of body 1. Body 1 is preferably made from an injection moldable medical grade plastic such acrylic, polycarbonate, polysulfone, polypropylene, polyethylene, but is not limited to these materials.

Figure 7:
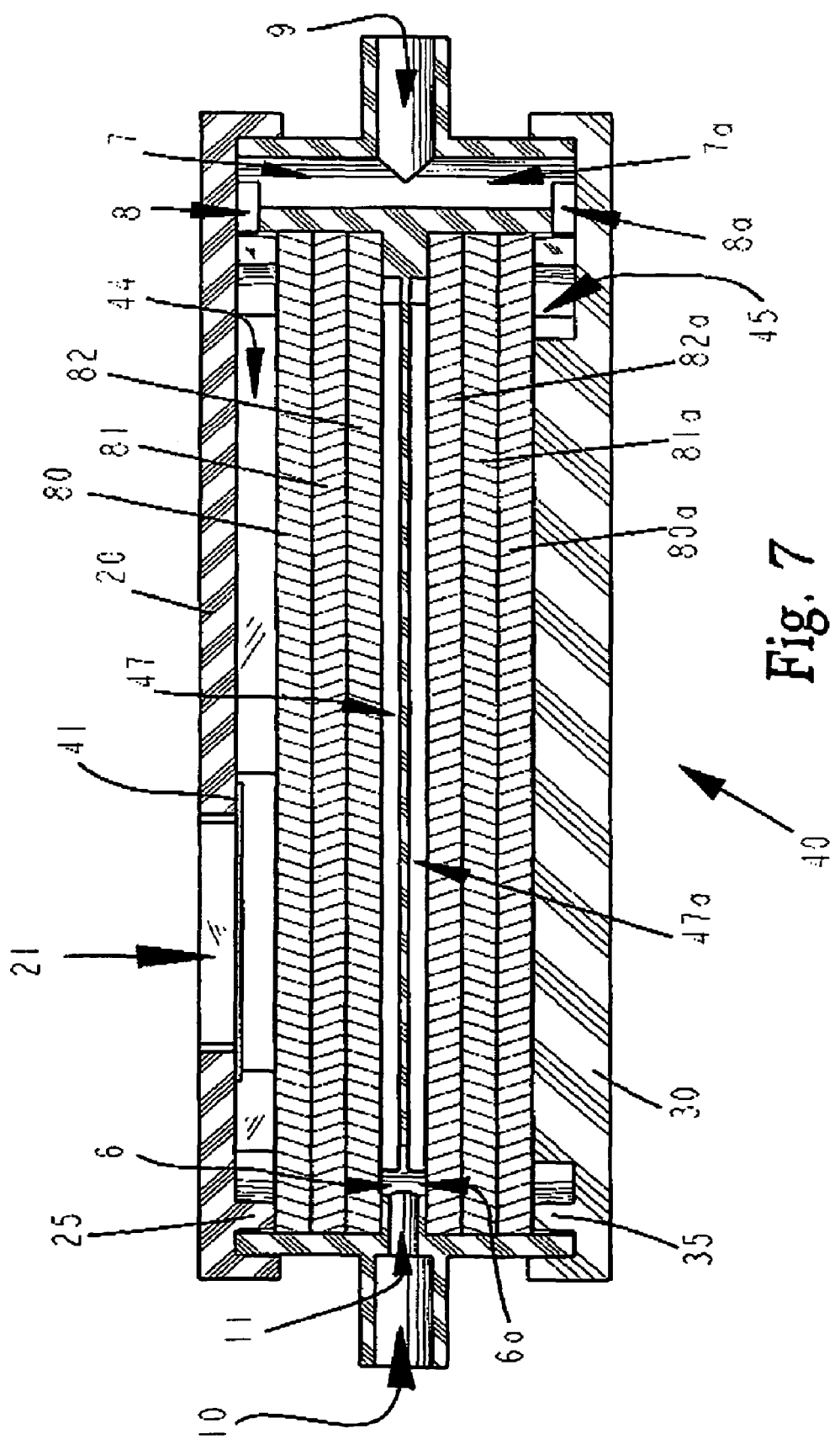
FIG. 7 is a cross-sectional view of the filtration apparatus depicted in FIG. 6.
Figure 21:
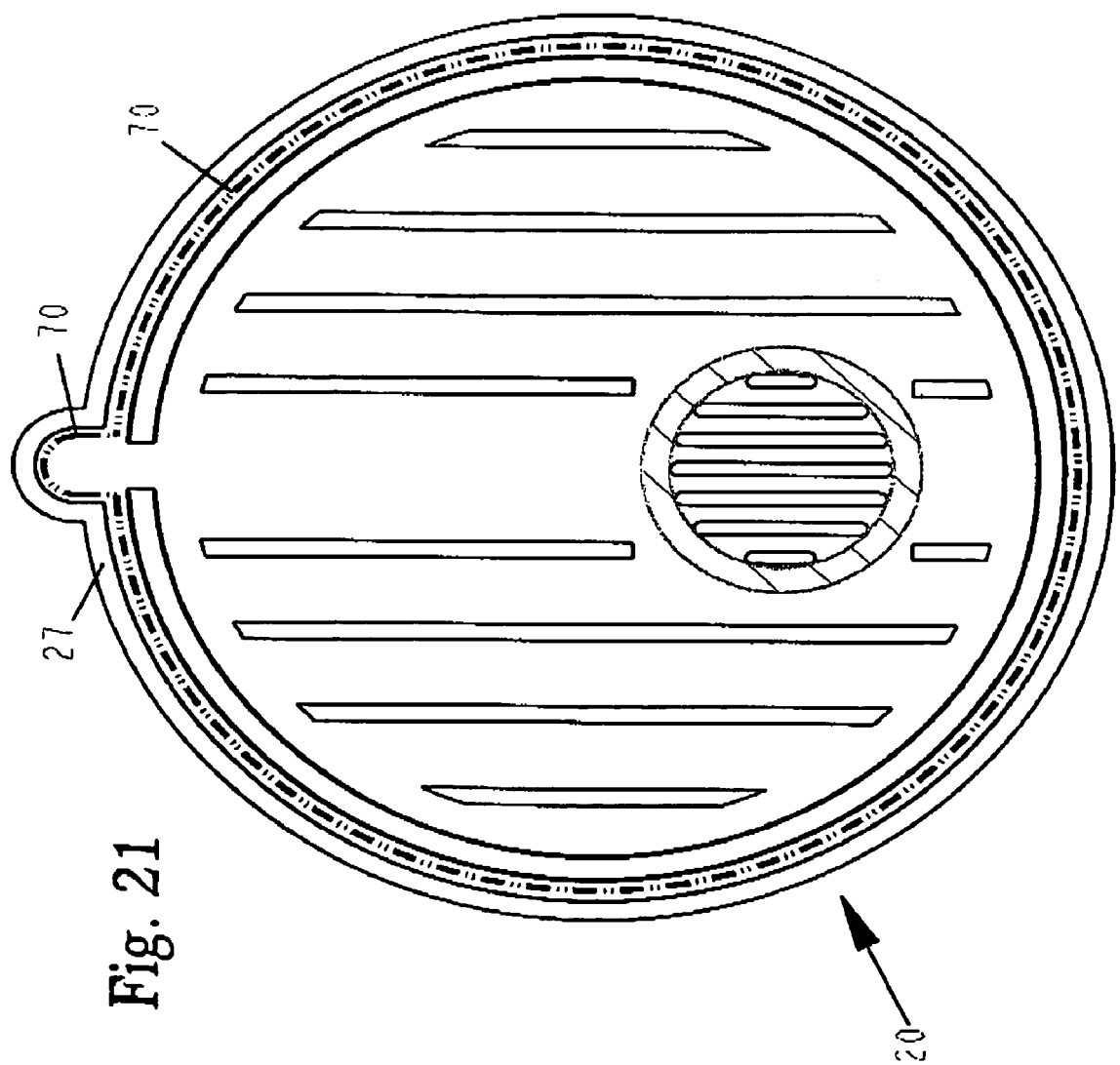
FIG. 21 is a back view of the front cover of the filtration apparatus depicted in FIG. 6.

FIG. 4A, FIG. 4B, and FIG. 21 show front cover 20. Front cover 20 is round in shape to match the shape of body 1, (if body 1 was square, then front cover 20 would also be square) and contains boss 29 at its upper end. The interior of front cover 20 contains flat surface 23. Vertical filter support ribs 24 protrude from flat surface 23. The vertical filter support ribs 24 could be replaced with ribs oriented in a direction other than vertical, or with a pattern of round pins, or with a pattern or rectangular pins, or with a pattern of concentric rings with gaps in the rings, or with any other filter support means that does not contain a closed loop. Outer rib 27 also protrudes from flat surface 23 and follows the outer periphery of front cover 20. Although it is not necessary for front cover 20 to contain outer rib 27, outer rib 27 acts as an alignment rib during assembly, and as a flash trap to contain flash when front cover 20 is assembled to body 1. Front cover 20 also contains round filter support rib 25. Round filter support rib 25 contains gap 26 located at the upper end of front cover 20, below boss 29. Front cover 20 also contains through slots 21, and vent filter bonding area 28. Although filter bonding area 28 is shown round for bonding a round vent filter, the vent filter could be square or any other shape, and then the filter bonding area 28 would conform to the shape of the vent filter. Through slots 21 are shown as vertical slots, but could be replaced by a pattern of round holes, or a pattern of square holes, or any other pattern of through holes that provide adequate filter support, and also provide air flow communication between the face of the vent filter that is bonded to flat surface 23, and to the outside atmosphere of front cover 20. FIG. 7 shows vent filter element 41 bonded to front cover 20. The outside of front cover 20 contains flat surface 22. Referring to FIG. 21, centerline 70 shows the center of the seal between front cover 20 and body 1. The seal could be an ultrasonic weld, a glue bond, a heat bond, a solvent bond, or any other type of leak tight bond. Front cover 20 is preferably made from an injection moldable medical grade plastic such acrylic, polycarbonate, polysulfone, polypropylene, polyethylene, but is not limited to these materials.

FIG. 5A, FIG. 5B, and FIG. 21 show back cover 30. Back cover 30 is round in shape to match the shape of body 1, (if body 1 was square, then back cover 30 would also be square) and contains boss 39 at its upper end. The interior of back cover 30 contains flat surface 33. Vertical filter support ribs 34 protrude from flat surface 33. The vertical filter support ribs 34 could be replaced with ribs oriented in a direction other than vertical, or with a pattern of round pins, or with a pattern of rectangular pins, or with a pattern of concentric rings with gaps in the rings, or with any other filter support means that does not contain a closed loop. Outer rib 37 also protrudes from flat surface 33 and follows the outer periphery of back cover 30. Although it is not necessary for back cover 30 to contain outer rib 37, outer rib 37 acts as an alignment rib during assembly, and as a flash trap to contain flash when back cover 30 is assembled to body 1. Back cover 30 also contains round filter support rib 35. Round filter support rib 35 contains gap 36 located at the upper end of back cover 30, below boss 39. The outside of back cover 30 contains flat surface 32. Back cover 30 is identical to front cover 20 with the exception that back cover 30 does not contain a vent filter. Referring to FIG. 21, centerline 70 shows the center of the seal between back cover 30 and body 1. Back cover 30 is preferably made from an injection moldable medical grade plastic such acrylic, polycarbonate, polysulfone, polypropylene, polyethylene, but is not limited to these materials.

Figure 8:
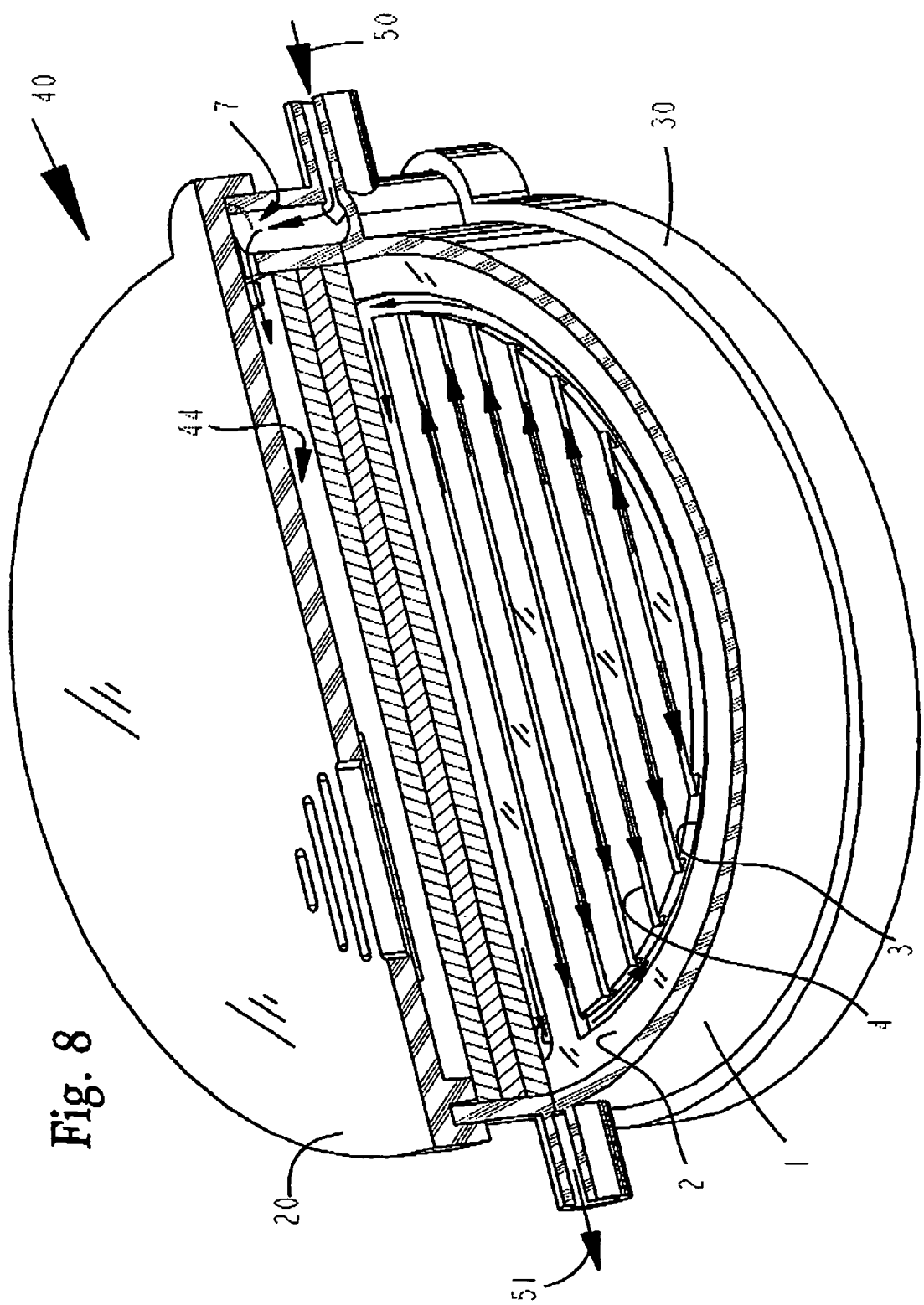
FIG. 8 is an isometric view of the filtration apparatus depicted in FIG. 6, having portions thereof removed.

FIG. 6 shows an exploded view of the components that comprise filter device 40. The components are body 1, front cover 20, back cover 30, vent filter element 41, and filter elements 80, 81, and 82, and filter elements 80a, 81a, and 82a. FIG. 7 and FIG. 8 show filter device 40 in the assembled state. Referring to FIG. 1A, FIG. 1B, FIG. 2, FIG. 4B, FIG. 5B, FIG. 6, FIG. 7, FIG. 8, and FIG. 21, the components that comprise filter device 40 are assembled as follows. The outer periphery of vent filter element 41 is sealed to front cover 20 at filter bonding area 28. The seal is preferably a heat seal but could be an ultrasonic seal, a glue bond, a solvent bond, or any other type of bond that will produce a leak tight seal capable of maintaining sterility. Filter element 41 is a hydrophobic filter with a pore size of 0.2µ or smaller to maintain sterility. Filter elements 80, 81, and 82 are placed into first filter well 13. Front cover 20 is then bonded to body 1 so that edge 12 of body 1 is bonded to front cover 20 along centerline 70 shown in FIG. 21. The seal between front cover 20 and body 1 forms a single closed loop that encloses the outer periphery of first filter well 13 and the outer periphery of front inlet channel 8, thereby creating a closed first chamber 44 in first filter well 13, and a closed front inlet channel 8 that extends from front cross port 7 to first chamber 44 of first filter well 13, thereby creating a flow path from inlet port 9, through front cross port 7, through front inlet channel 8, into first chamber 44 of first filter well 13. Outer rib 27 of front cover 20 aligns front cover 20 to body 1 during the assembly procedure and also acts as a flash trap. The bond between front cover 20 and body 1 is preferably an ultrasonic seal but could be a glue bond, a heat bond, a solvent bond or any other type of bond that creates a leak tight seal. Filter elements 80, 81, and 82 are sealed to body 1 with a compression seal between the outer edges 84, 85, and 86 of filter elements 80, 81, and 82 respectively, and cylindrical surface 14 of body 1 in the filter device 40 shown. However, filter elements 80, 81, and 82 could be sealed to body 1 with a glue seal, a heat seal, a compression seal, or any other type of seal that eliminates bypass around filter elements 80, 81, and 82. Filter device 40 is shown with 3 filter elements 80, 81, and 82 in first filter well 13. However any number of filter elements greater than or equal to one could be used. The number of filter elements used is determined by the filter type and the fluid being filtered. The same number of filter elements that were placed into first filter well 13 of body 1 are now placed into second filter well 13a of body 1, and are designated as filter elements 80a, 81a, and 82a. These filter elements are sealed to body 1 using the same method that was used to seal filter elements 80, 81, and 82 to first filter well 13. Back cover 30 is then bonded to body 1 so that edge 12a of body 1 is bonded to back cover 30 along the same path as centerline 70 shown in FIG. 21. The seal between back cover 30 and body 1 forms a single closed loop that encloses the outer periphery of second filter well 13a and the outer periphery of back inlet channel 8a, thereby creating a closed first chamber 45 in second filter well 13a, and a closed back inlet channel 8a that extends from back cross port 7a to first chamber 45 of second filter well 13a, thereby creating a flow path from inlet port 9, through back cross port 7a, through back inlet channel 8a, into first chamber 45 of second filter well 13a. Outer rib 37 of back cover 30 aligns back cover 30 to body 1 during the assembly procedure and also acts as a flash trap. The bond between back cover 30 and body 1 is preferably an ultrasonic seal but could be a glue bond, a heat bond, a solvent bond or any other type of bond that creates a leak tight seal.

Referring to FIG. 4B, FIG. 6, FIG. 7, and FIG. 8, the assembled filter device 40 contains first chamber 44 of first filter well 13 bounded by flat surface 23 of front cover 20, inner surface 77 of round rib 25 of front cover 20, and the upstream surface 46 of the first filter element 80 in first filter well 13 of body 1. Referring to FIG. 5B, FIG. 6, and FIG. 7, the assembled filter device 40 also contains first chamber 45 of second filter well 13a bounded by flat surface 33 of back cover 30, inner surface 71 of round rib 35 of back cover 30, and the upstream surface 46a of the first filter element 80a in second filter well 13a of body 1. Referring to FIG. 3A, FIG. 4B and FIG. 7, in the assembled filter device 40, front inlet channel 8 becomes a closed channel bounded by side walls 15 and wall 16 of body 1, and by flat surface 23 of front cover 20. Referring to FIG. 7, front inlet channel 8 places first chamber 44 in fluid flow communication, and in air flow communication with front cross port 7. Referring to FIG. 3B, FIG. 5B, and FIG. 7, in the assembled filter device 40, back inlet channel 8a becomes a closed channel bounded by side walls 15a and wall 16a of body 1, and by flat surface 33 of back cover 30. Referring to FIG. 7, back inlet channel 8a places first chamber 45 in fluid flow communication, and in air flow communication with back cross port 7a.

Referring to FIG. 1a, FIG. 2, FIG. 6 and FIG. 7, the assembled filter device 40 contains second chamber 47 of first filter well 13 bounded by the downstream surface 48 of the last filter element 82 in first filter well 13 of body 1, and by center vertical channel 5, circular channel 3, and side vertical channels 4. Second chamber 47 of first filter well 13 contains front outlet port 6. Referring to FIG. 1b, FIG. 6 and FIG. 7, the assembled filter device 40 contains second chamber 47a of second filter well 13a bounded by the downstream surface 48a of the last filter element 82a in second filter well 13a of body 1, and by center vertical channel 5a, circular channel 3a, and side vertical channels 4a. Second chamber 47a of second filter well 13a contains back outlet port 6a.

Figure 9:
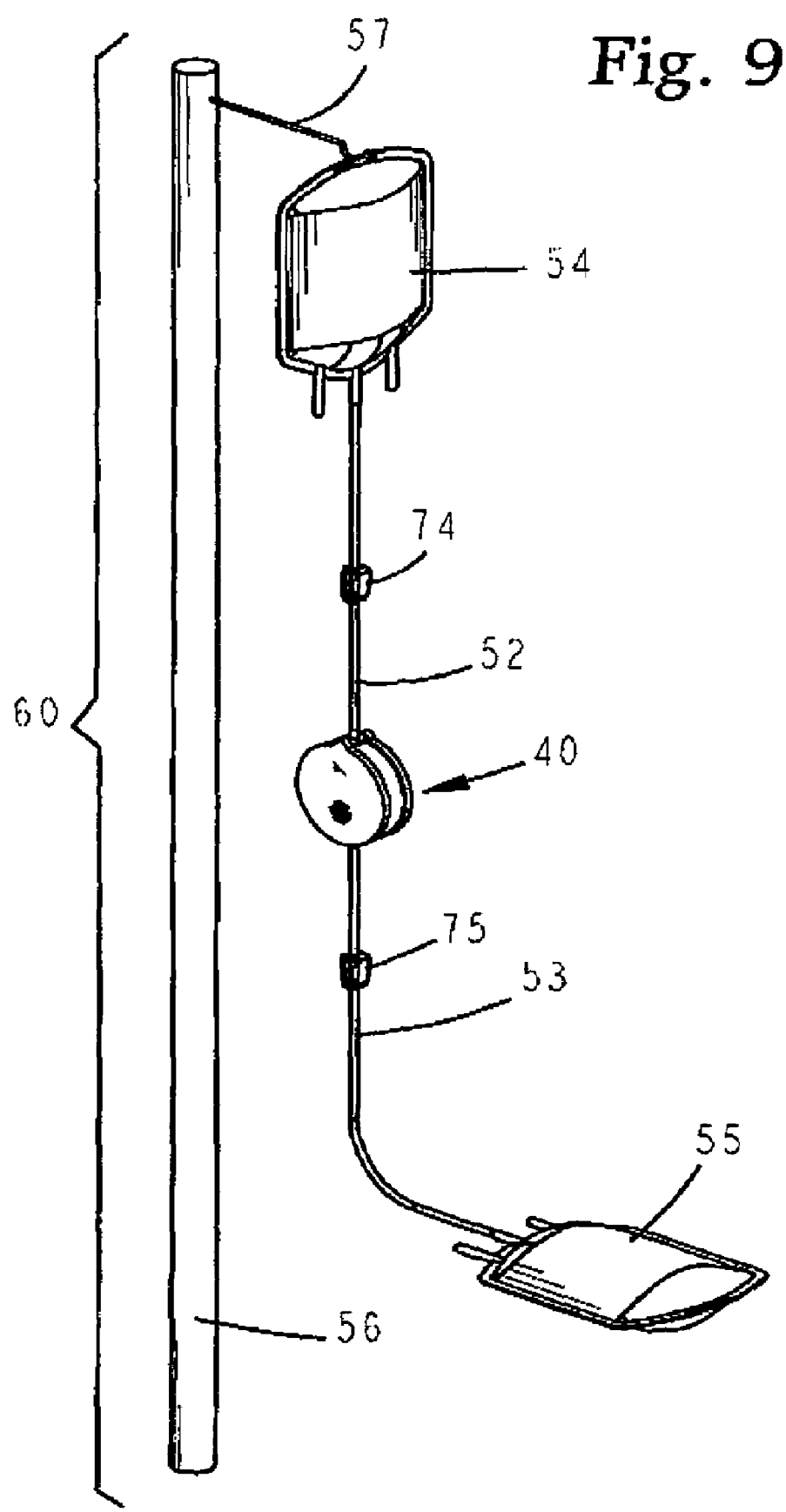
FIG. 9 is an isometric view of a blood filtration assembly containing the filtration apparatus depicted in FIG. 6.
Figure 10:
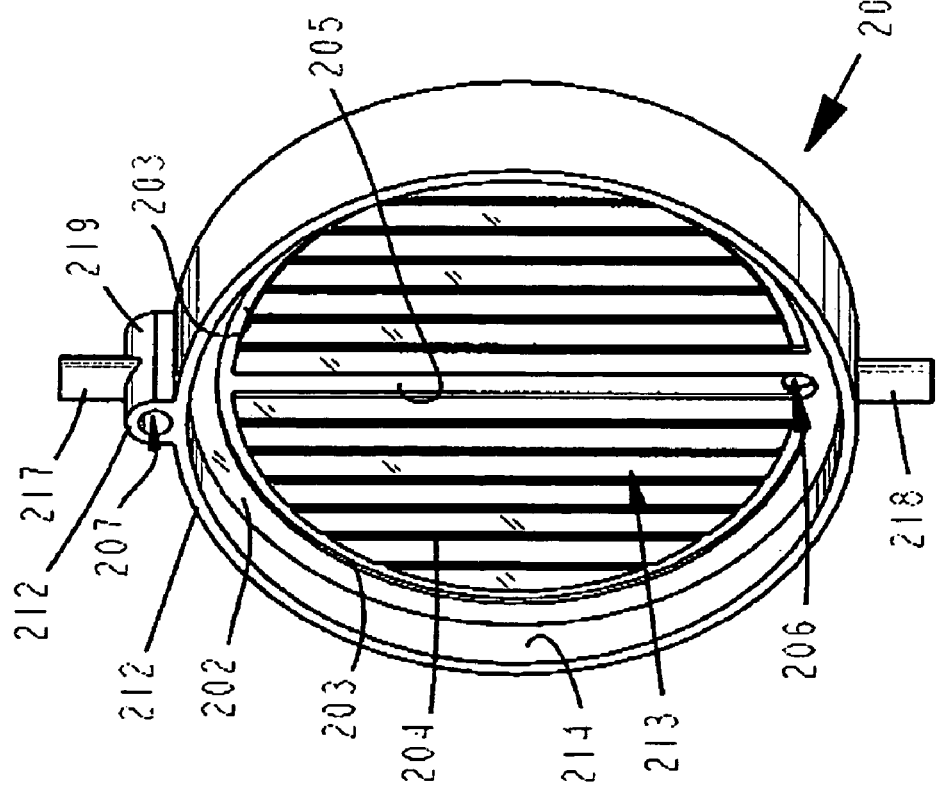
FIG. 10A is a front isometric view of the body of the filtration apparatus depicted in FIG. 17.
FIG. 10B is a back isometric view of the body of the filtration apparatus depicted in FIG. 17.

Referring to FIG. 9 one end of a length of outlet tubing 53 is bonded to outlet tube socket 18 of body 1, with the other end of said outlet tubing bonded to an empty blood bag 55. Another length of inlet tubing 52 is bonded to inlet tube socket 17 of body 1. The end user will preferably purchase the assembly of filter device 40, inlet tubing 52, outlet tubing 53, and receiving blood bag 55, assembled and sterile. The assembly will also contain an inlet tubing clamp 74 on inlet tubing 52, and an outlet tubing clamp 75 on outlet tubing 53.

In FIG. 9 the filter device 40 is in an operational assembly with inlet tubing 52, outlet tubing 53, feed blood bag 54, receiving blood bag 55, inlet tube clamp 76, and outlet tube clamp 75. Preferably, the user will purchase the assembly of FIG. 9 sterilized without feed blood bag 54 with the inlet end of inlet tubing 52 sealed to maintain system sterility. For performing filtration the user will first close inlet tube clamp 74 close to the inlet end of inlet tubing 52. Next the user will make sure that outlet tube clamp 75 is open. Inlet tubing 52 is now bonded by the user to a pigtail on feed blood bag 54 using a sterile docking device as is well known in the art.

Once the sterile docking connection is made the user will hang feed blood bag 54 from hook 57 on blood bag pole 56. Receiving blood bag 55 should be placed on a surface such as a table top or the like. The complete assembly 60 ready for filtration is illustrated in FIG. 9.

Referring to FIG. 1A, FIG. 4B, FIG. 5B, FIG. 7, FIG. 8 and FIG. 9 the filtration is performed as follows. The user opens inlet tube clamp 74. Gravity now forces blood to flow from feed blood bag 54, through inlet tubing 52, through inlet port 9 of body 1. After passing through inlet port 9, a portion of the blood passes through front cross port 7, while the remainder of the blood passes through back cross port 7a. The portion of the blood that passes through front cross port 7, then passes through front inlet channel 8, through gap 26 of front cover 20, into first chamber 44. The portion of the blood that passes through back cross port 7a, then passes through back inlet channel 8a, through gap 36 of back cover 30, into first chamber 45. A portion of the air that was in inlet tubing 52 and inlet port 9 before blood flow started will be pushed ahead of the blood, through front cross port 7, through front inlet channel 8, through gap 26 of front cover 20, into first chamber 44. The remainder of the air that was in inlet tubing 52 and inlet port 9 before blood flow started will be pushed ahead of the blood, through back cross port 7a, through back inlet channel 8a, through gap 36 of back cover 30, into first chamber 45. Because the usable surface area of hydrophobic filter 41 is much smaller than the usable surface area of filter elements 80, 81, and 82; and because the pressure drop across sterilizing grade hydrophobic filter 41 is much greater per unit volume of air flow per unit surface area of filter material than the combined pressure drop across filter elements 80, 81, and 82 per unit volume of air flow per unit surface area of filter material, only a very small portion of the air that was in inlet tubing 52, inlet port 9, front cross port 7, and front inlet channel 8 before blood flow started, will pass through hydrophobic filter 41, and then through slots 21 of front cover 20 to atmosphere.

As first chamber 44 fills from the bottom up most of the air in first chamber 44 will be forced through filter elements 80, 81, and 82, for the same reasons described in the previous paragraph. This initial air will flow into vertical channels 4, circular channel 3, and center vertical channel 5, and then flow through front outlet port 6, through link port 11, through outlet port 10, into outlet tubing 53, into receiving blood bag 55. Filter elements 80, 81, and 82 will also wet from the bottom up. The air that is initially in filter elements 80, 81, and 82 will be displaced by blood and flow into vertical channels 4, circular channel 3, and center vertical channel 5, and then flow through front outlet port 6, through link port 11, through outlet port 10, into outlet tubing 53, into receiving blood bag 55. Because the volume of first chamber 44 is small, and the flow rate of blood entering first chamber 44 is much greater than the initial flow rate of blood through filter elements 80, 81, and 82, first chamber 44 will fill in a very small fraction of the time that it takes to wet filter elements 80, 81, and 82. The pressure head at the bottom of first chamber 44 will be larger than the pressure head at the top of first chamber 44, because of the height difference between the top and bottom of first chamber 44. Therefore liquid will start to come through filter element 82 from the bottom up. As liquid starts to come through filter element 82 from the bottom up vertical channels 4, circular channel 3, and center vertical channel 5, of body 1 will fill from the bottom up. Because the total volume of these channels in is small (to minimize holdup) the channels may fill with blood (from the bottom up) before the upper part of filter element 82 has wet with blood. Once a sufficient quantity of blood flows from center vertical channel 5 of body 1, into front outlet port 6 of body 1, through link port 11 of body 1, through outlet port 10 of body 1, into outlet tubing 53, and flows down outlet tubing 53 toward receiving blood bag 55, the pressure in front outlet port 6 will become negative. Because center vertical channel 5 is in fluid flow relationship with front outlet port 6, the pressure inside the tube created by center vertical channel 5 and downstream surface 48 of filter element 82 will also be negative. Likewise since circular channel 3 is in fluid flow relationship with center vertical channel 5 the pressure inside the tube created by circular channel 3 and downstream surface 48 of filter element 82 will also be negative. Since the tube segments made up of vertical channels 4 and downstream surface 48 of filter element 82 are in fluid flow relationship with the tube created by circular channel 3 and downstream surface 48 of filter element 82, any air or liquid that flows from filter element 82 into vertical channels 4 after the pressure in the front outlet port becomes negative, will be sucked into circular channel 3, and then flow from circular channel 3 into center vertical channel 5, through front outlet port 6, through link port 11, through outlet port 10, into outlet tubing 53, and into receiving blood bag 55. This assures that filter elements 80, 81, and 82 will completely wet, and that all of the air that was in first chamber 44, filter elements 80, 81, and 82, vertical channels 4, circular channel 3, center circular channel 5, front outlet port 6, link port 11, outlet port 10, and the interior of outlet tubing 53 will be forced into receiving blood bag 55. Although vertical channels 4 are shown in the vertical orientation, they could be orientated at any angle from zero degrees to ninety degrees from vertical, as long as they are in fluid flow relationship with circular channel 3. Other channel designs such as the spiral channel filter underdrain disclosed in U.S. Ser. No. 08/524,049, and entitled "an In-Line Liquid Filtration Device Usable for Blood, Blood Products and the Like", could also be used in place of the design illustrated in FIG. 1A. It is however, imperative that all channels be either directly or indirectly in fluid flow relationship with front outlet port 6.

The portion of blood from feed blood bag 54 which flows through back cross port 7a, through back inlet channel 8a, through gap 36, into first chamber 45, will fill first chamber 45 from the bottom forcing all of the air in first chamber 45 through filter elements 80a, 81a, and 82a. This initial air will flow into vertical channels 4a, circular channel 3a, and center vertical channel 5a, and then flow through back outlet port 6a, through link port 11, through outlet port 10, into outlet tubing 53, into receiving blood bag 55. Filter elements 80a, 81a, and 82a will also wet from the bottom up. The air that is initially in filter elements 80a, 81a, and 82a will be displaced by blood and flow into vertical channels 4a, circular channel 3a, and center vertical channel 5a, and then flow through outlet port 6a, through link port 11, through outlet port 10, into outlet tubing 53, into receiving blood bag 55. Because the volume of first chamber 45 is small, and the flow rate of blood entering first chamber 45 is much greater than the initial flow rate of blood through filter elements 80a, 81a, and 82a, first chamber 45 will fill in a very small fraction of the time that it takes to wet filter elements 80a, 81a, and 82a. The pressure head at the bottom of first chamber 45 will be larger than the pressure head at the top of first chamber 45, because of the height difference between the top and bottom of first chamber 45. Therefore liquid will start to come through filter element 82a from the bottom up.

As liquid starts to come through filter element 82a from the bottom up vertical channels 4a, circular channel 3a, and center vertical channel 5a, of body 1 will fill from the bottom up. Because the total volume of these channels in is small (to minimize holdup) the channels may fill with blood (from the bottom up) before the upper part of filter element 82a has wet with blood. Once a sufficient quantity of blood flows from center vertical channel 5a of body 1, into back outlet port 6a of body 1, through link port 11 of body 1, through outlet port 10 of body 1, into outlet tubing 53, and flows down outlet tubing 53 toward receiving blood bag 55, the pressure in back outlet port 6a will become negative. Because center vertical channel 5a is in fluid flow relationship with back outlet port 6a, the pressure inside the tube created by center vertical channel 5a and the downstream surface 48a of filter element 82a will also be negative. Likewise since circular channel 3a is in fluid flow relationship with center vertical channel 5a the pressure inside the tube created by circular channel 3a and the downstream surface 48a of filter element 82a will also be negative. Since the tube segments made up of vertical channels 4a and the downstream surface 48a of filter element 82a are in fluid flow relationship with the tube created by circular channel 3a and the downstream surface 48a of filter element 82a, any air or liquid that flows from filter element 82a into vertical channels 4a after the pressure in the front outlet port becomes negative, will be sucked into circular channel 3a, and then flow from circular channel 3a into center vertical channel 5a, through back outlet port 6a, through link port 11, through outlet port 10, into outlet tubing 53, and into receiving blood bag 55. This assures that filter elements 80a, 81a, and 82a will completely wet, and that all of the air that was in first chamber 45, filter elements 80a, 81a, and 82a, vertical channels 4a, circular channel 3a, center circular channel 5a, back outlet port 6a, link port 11, outlet port 10, and the interior of outlet tubing 53 will be forced into receiving blood bag 55. Although vertical channels 4a are shown in the vertical orientation, they could be orientated at any angle from zero degrees to ninety degrees from vertical, as long as they are in fluid flow relationship with circular channel 3a. Other channel designs such as the spiral channel filter underdrain disclosed in U.S. Ser. No. 08/524,049, and entitled "an In-Line Liquid Filtration Device Usable for Blood, Blood Products and the Like", could also be used in place of the design illustrated in FIG. 1B. It is however, imperative that all channels be either directly or indirectly in fluid flow relationship with back outlet port 6a.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in front outlet port 6, and the pressure head in back outlet port 6a will be negative, as will be the pressure head in vertical channels 4, circular channel 3, center vertical channel 5, vertical channels 4a, circular channel 3a, and center vertical channel 5a, all of body 1. Once blood flow has stopped the pressure drop across filter elements 80, 81, and 82, will fall to zero. The pressure drop across filter elements 80a, 81a, and 82a, will also fall to zero. Hence the pressure in first chamber 44 and first chamber 45 will become negative. Once the pressure in first chamber 44 falls below atmospheric pressure air will begin to flow from atmosphere through slots 21, through sterilizing grade hydrophobic filter 41, into first chamber 44. The sterile air that enters first chamber 44 will bubble up to the top of first chamber 44, thus causing first chamber 44 to drain from the top down. Because of the negative pressure in first chamber 45, some of the air that bubbles to the top of first chamber 44 will pass through gap 26, through front inlet channel 8, through front cross port 7, through back cross port 7a, through gap 36, through back inlet channel 8a, into first chamber 45, causing first chamber 45 to drain from the top down, and causing the blood in front inlet channel 8 to drain into first chamber 44, and causing the blood in back inlet channel 8a to drain into first chamber 45, and causing the blood in front cross port 7 and back cross port 7a to drain into both first chamber 44 and first chamber 45. Because the air entering first chamber 44 bubbles to the top of first chamber 44, thus draining first chamber 44 from the top down, vent filter element 41 can be located anywhere on flat surface 23 of front cover 20. Filter elements 80, 81, 82, 80a, 81a, and 82a will be plugged sufficiently at this point, therefore very little if any blood will be sucked from these filter elements by the negative pressure in front outlet port 6, and by the negative pressure in back outlet port 6a. Hence blood flow will stop after first chamber 44 and first chamber 45 have drained and blood will remain in filter elements 80, 81, 82, 80a, 81a, and 82a, and in vertical channels 4, circular channel 3, center vertical channel 5, vertical channels 4a, circular channel 3a, and center vertical channel 5a, and in front outlet port 6, back outlet port 6a, link port 11, outlet port 10 all of body 1, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 40 can now be discarded in a safe manner. Outlet tubing 53 will have segments marked on them. The user can now seal the tubing at the segment marks. The blood that is left in outlet tubing 53 will be used for cross matching and for quality control purposes.

Referring to FIG. 2, with front outlet port 6 and back outlet port 6a at the very bottom of center vertical channels 5 and 5a respectively, the length of link port 11 is minimized, thereby minimizing the diameter of the pin (a minimum diameter is needed to prevent breakage of the pin) in the injection mold, thereby minimizing the wall thickness of partition wall 300 of body 1, thereby reducing the cost of body 1.

A second embodiment of the filtration device constructed in accordance with the principles of the present invention, could be constructed by replacing the back cover 30 of the first embodiment with a second front cover 20. The second embodiment would work the same as the first embodiment, with the exception that after the feed blood bag is empty, air would enter first chamber 45 from the vent filter on the front cover 20 that replaces the back cover 30.

The first and second embodiments of the present invention contain the following shortcoming if it is desired to seal filter elements 80, 81, and 82 into first filter well 13 of body 1 by compressing the outer periphery of said filter elements between round filter support rib 25 of front cover 20 and front flat surface 2 of body 1. Referring to FIG. 2, FIG. 4B and FIG. 7, the peripheral compression seal contains a break at gap 26 of round filter support rib 25 of front cover 20. Therefore a small portion of unfiltered blood will flow into the gap between outer wall 72 of round filter support rib 25 of front cover 20 and cylindrical surface 14 of body 1. Likewise, referring to FIG. 1B, FIG. 5B, and FIG. 7, if it is desired to seal filter elements 80a, 81a, and 82a into second filter well 13a of body 1 by compressing the outer periphery of said filter elements between round filter support rib 35 and back flat surface 2a of body 1, said compression seal contains a break at gap 36 of round filter support rib 35 of back cover 30. Therefore a small portion of unfiltered blood will flow into the gap between outer wall 73 of round filter support rib 35 of back cover 30 and cylindrical surface 14a of body 1. The third embodiment constructed in accordance with the principles of the present invention overcomes these shortcomings.

Figure 25:
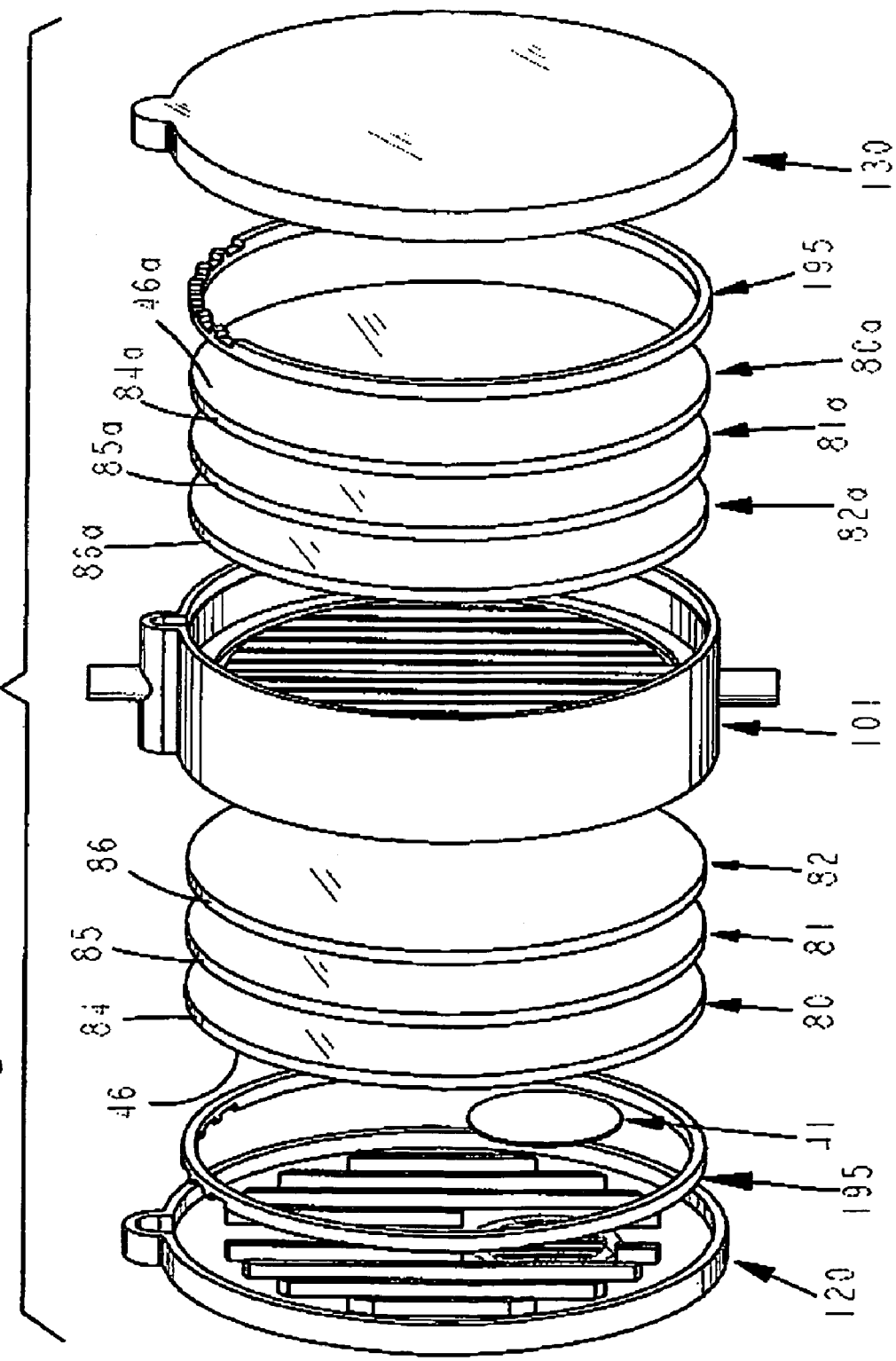
FIG. 25 is an exploded isometric view of the components that comprise the third embodiment of the filtration apparatus, constructed in accordance with the principles of the present invention, usable for the gravity filtration of blood and blood products.

FIG. 25 shows an exploded view of the components that comprise the third embodiment of the present invention. Referring to FIG. 25, body 101 replaces body 1 of the first and second embodiments of the present invention. Likewise, front cover 120 replaces front cover 20, and back cover 130 replaces back cover 30 of the first and second embodiments of the present invention. The third embodiment also contains two filter compression rings 195.

Figure 22:
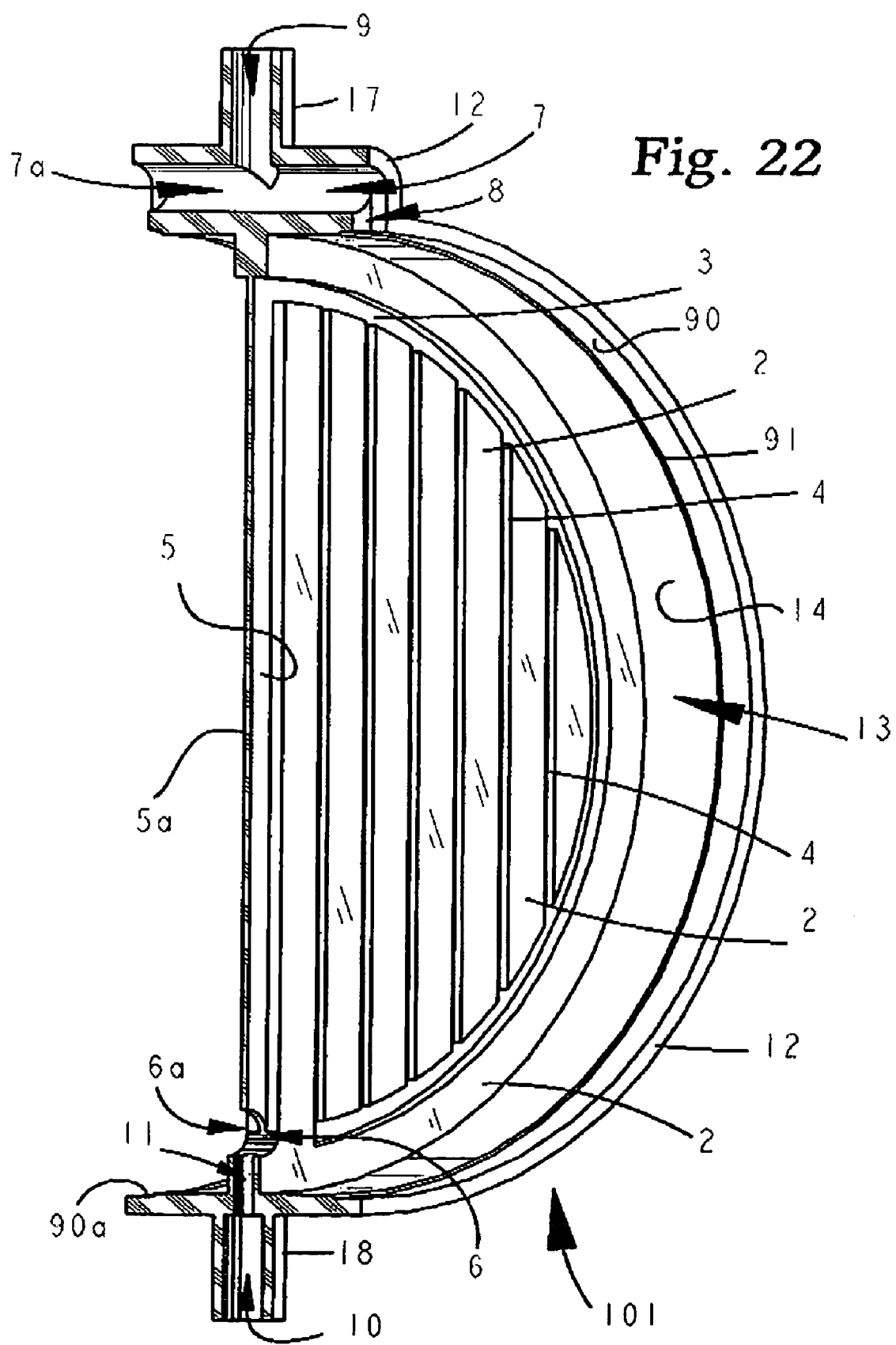
FIG. 22 is an isometric view, having portions thereof removed, of the body of the filtration apparatus depicted in FIG. 25.
Figure 23A:
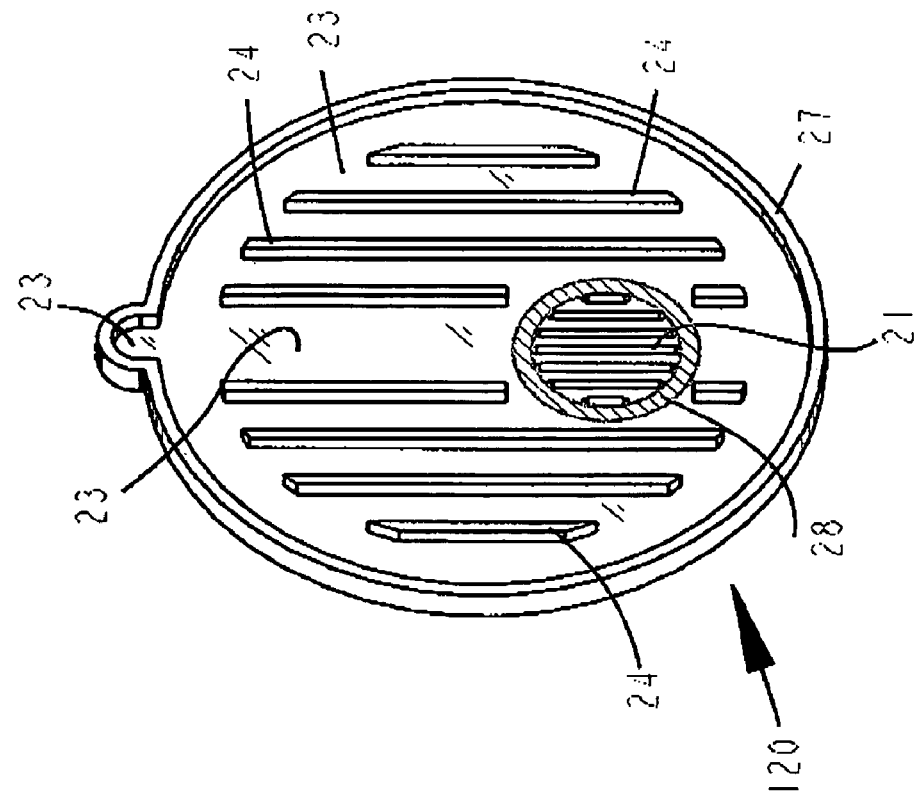
FIG. 23A is a front isometric view of the front cover of the filtration apparatus depicted in FIG. 25.
Figure 23B:
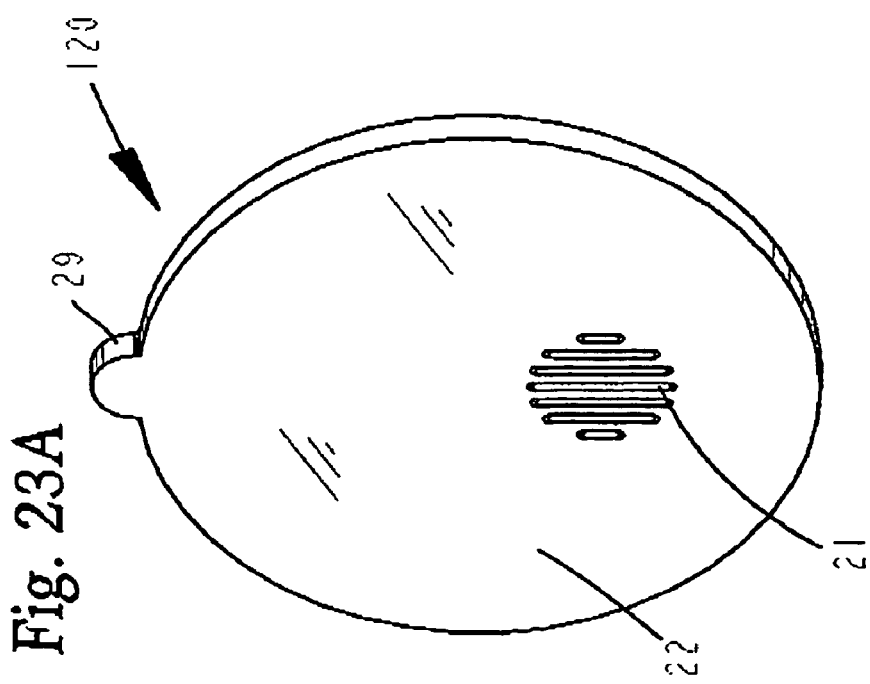
FIG. 23B is a back isometric view of the front cover of the filtration apparatus depicted in FIG. 25.
Figure 26:
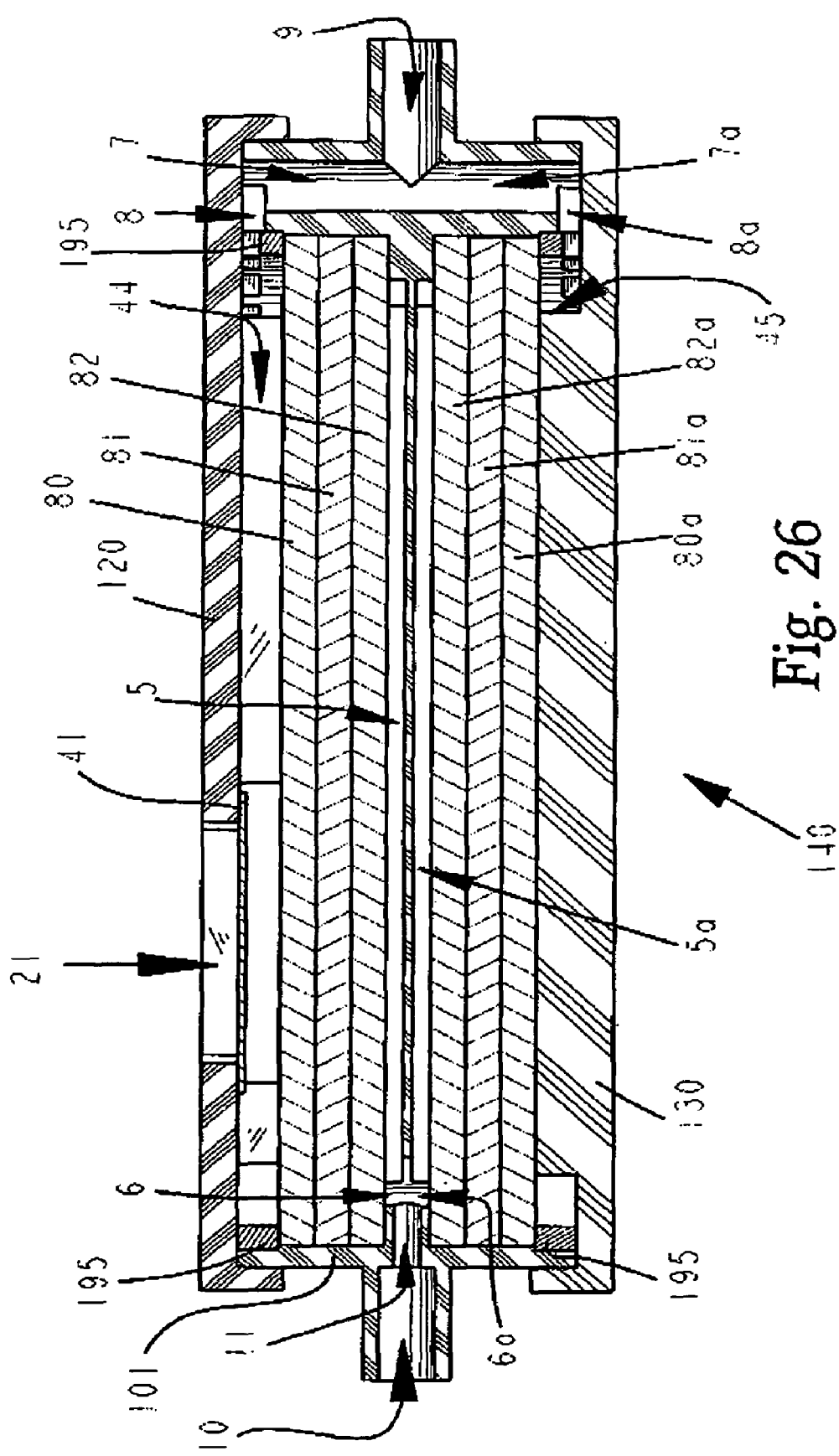
FIG. 26 is a cross-sectional view of the filtration apparatus depicted in FIG. 25.

Referring to FIG. 22, body 101 is the same as body 1 shown in FIG. 1a, FIG. 1B, and FIG. 2, with the exception that the front part of body 101 contains a counterbore in cylindrical surface 14, bounded by surface 90 and surface 91. The back part of body 101 shown in FIG. 25 also contains a corresponding counterbore. Referring to FIG. 23A and FIG. 23B, front cover 120 is identical to front cover 20 shown in FIG. 4A and FIG. 4B, with the exception that front cover 120 does not contain round filter support rib 25. Referring to FIG. 24A and FIG. 24B, back cover 130 is identical to back cover 30 shown in FIG. 5A and FIG. 5B, with the exception that back cover 130 does not contain round filter support rib 35. FIGS. 27A and 27B show filter compression ring 195. Filter compression ring 195 is a hollow cylinder, and contains one or more notches 196 in face 197. Each notch 196 is formed by two side walls 194 and an end wall 193. FIG. 25 and FIG. 26 show filter compression rings 195 properly oriented. When properly oriented notches 196 provide a liquid and gas flow path between front inlet channel 8 and first chamber 44, and provide a liquid and gas flow path between back inlet channel 8a and first chamber 45, as shown in FIG. 26. Only one notch 196 is necessary in compression ring 195 if compression ring 195 is properly aligned to front inlet channel 8, and back inlet channel 8a. Providing more than one notch 196 in filter compression ring 195 as shown in FIG. 27A, allows for some misalignment of filter compression ring 195 with respect to front inlet channel 8, and back inlet channel 8a, provided that the space between notches 196 is less than the width of front inlet channel 8 and back inlet channel 8a. If filter compression ring 195 contains more than one notch 196, said notches should be restricted to the top portion of filter compression ring 195 as shown in FIG. 25 and FIG. 27A, so that any blood that enters the notches during the filtration process can drain once filtration has stopped.

Referring to FIG. 22, FIG. 25, and FIG. 27a filter compression ring 195 should be sized so that outer wall 192 of filter compression ring 195 press fits into surface 90 of body 101, and so that outer wall 192 of filter compression ring 195 press fits into surface 90a of body 101, so that no gap will exist between outer wall 192 of filter compression ring 195 and surface 90 or surface 90a of body 101. Filter compression ring 195 is preferably made from an injection moldable plastic, and is preferably made of a softer plastic than body 101 to facilitate pressing filter compression ring 195 into body 101. Alternately filter compression ring 195 can be made of the same material as body 101, and sealed to body 101 with a sonic weld, a glue bond, a solvent bond or a heat bond, or any other type of suitable bond.

Filter device 140 shown in FIG. 26 functions the same as filter device 40 shown in FIG. 7. However the shortcomings of the first and second embodiments of the present invention as described above are overcome by the filter device shown in FIG. 26, because the filter compression rings provide a 360° compression seal around the outer periphery of filter elements 80, 81, and 82, and around the outer periphery of filter elements 80a, 81a, and 82a, and because the filter compression rings are press fitted into body 101, unfiltered blood can not flow between the outer wall 192 of the filter compression rings and body 101.

Referring to FIG. 22, with front outlet port 6 and back outlet port 6a at the very bottom of center vertical channels 5 and 5a respectively, the length of link port 11 is minimized, thereby minimizing the diameter of the pin (a minimum diameter is needed to prevent breakage of the pin) in the injection mold, thereby minimizing the wall thickness of the center section of body 101, thereby reducing the cost of body 101.

A fourth embodiment of the filtration device constructed in accordance with the principles of the present invention, could be constructed by replacing the back cover 130 of the third embodiment with a second front cover 120. The fourth embodiment would work the same as the third embodiment, with the exception that after the feed blood bag is empty, air would enter first chamber 45 from the vent filter on the front cover 120 that replaces the back cover 130.

Figure 16:
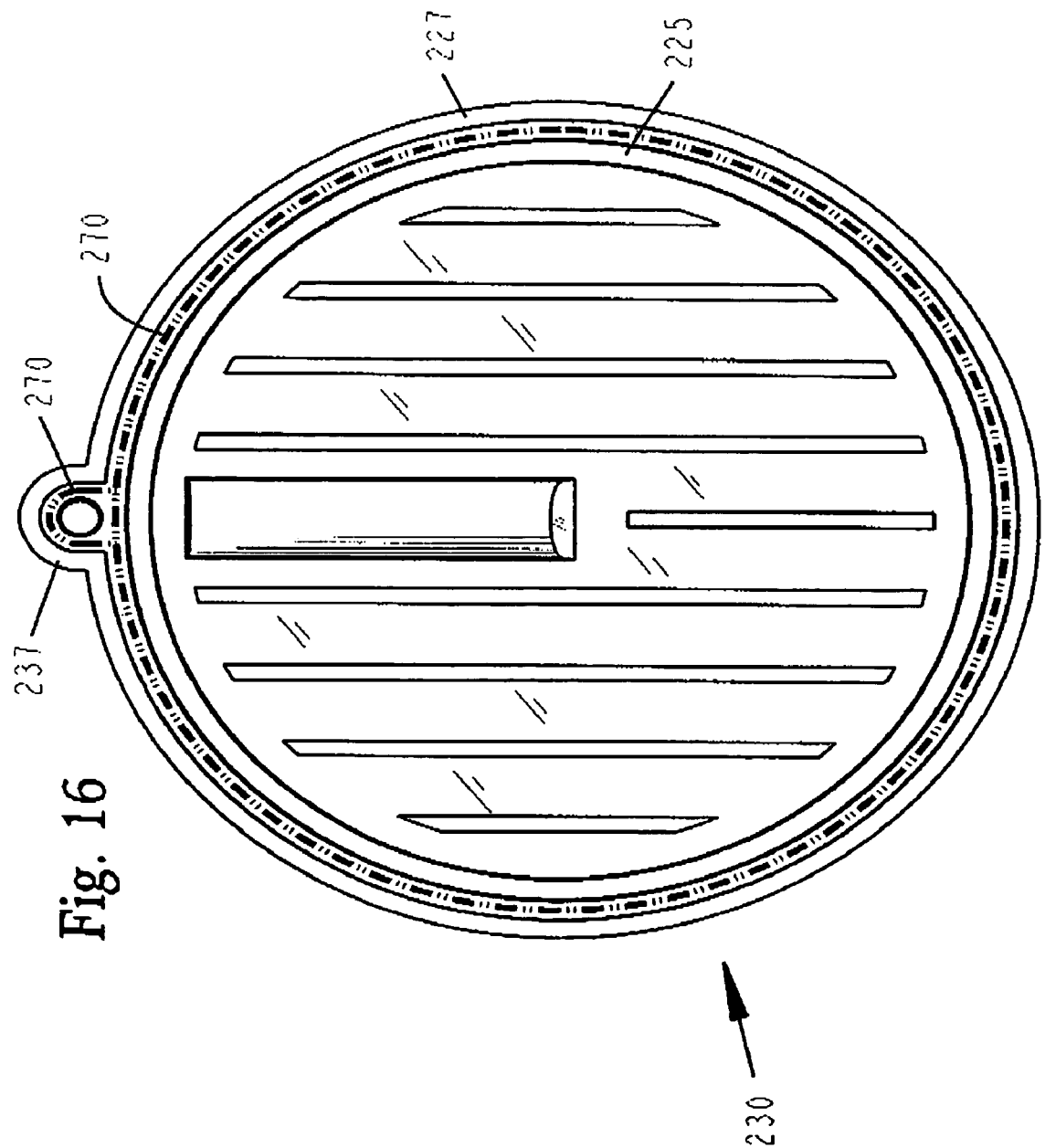
FIG. 16 is a back view of the back cover of the filtration apparatus depicted in FIG. 17.
Figure 17:
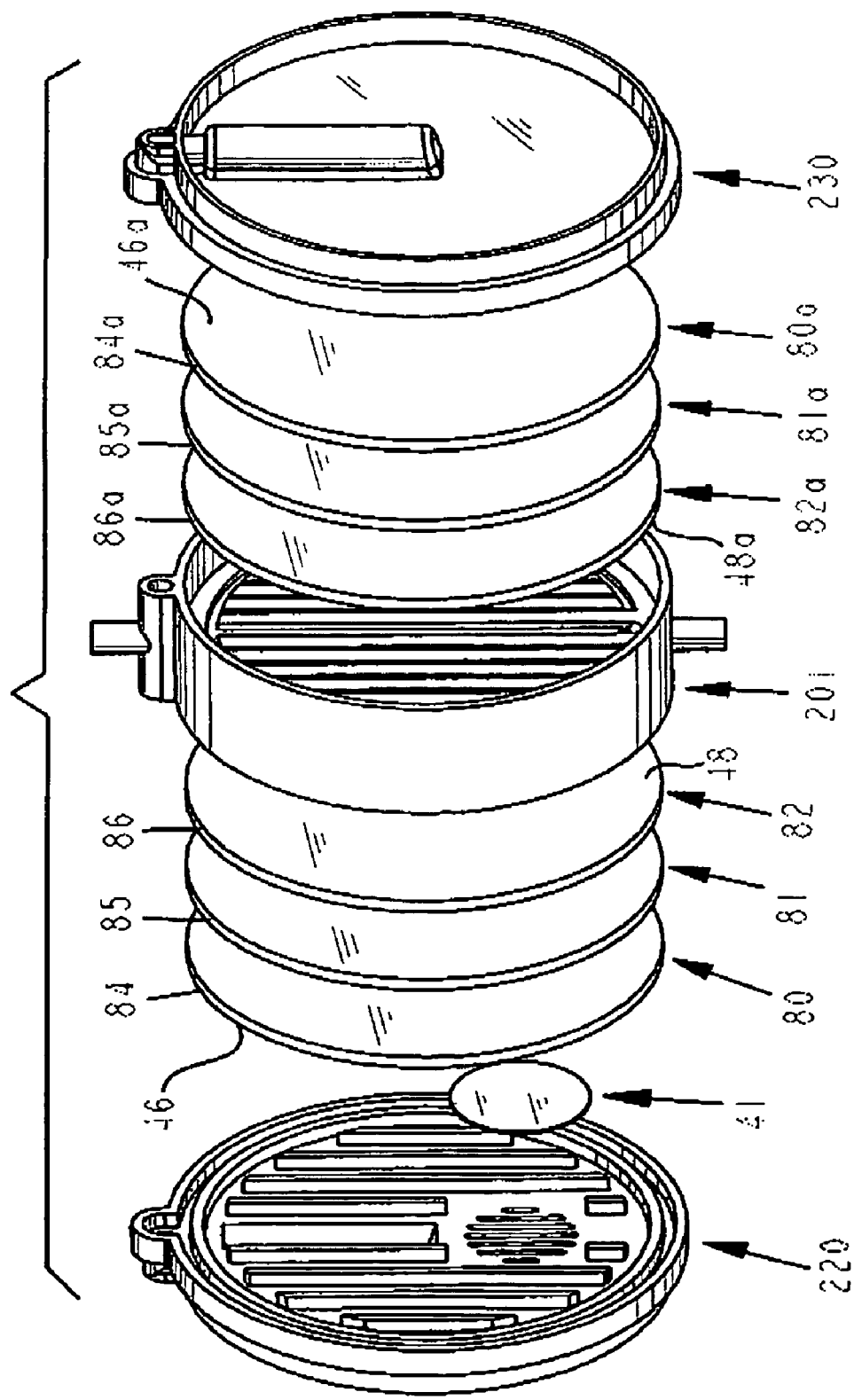
FIG. 17 is an exploded isometric view of the of the components that comprise the fifth embodiment of the filtration apparatus, constructed in accordance with the principles of the present invention, usable for the gravity filtration of blood and blood products.

A fifth embodiment of the filtration device constructed in accordance with the principles of the present invention, is shown in FIG. 10A through FIG. 20. Referring to FIG. 17 this embodiment includes the following major components: front cover 220, body 201, back cover 230, filter elements 80, 81, 82, 80a, 81a, and 82a, and hydrophobic vent filter element 41.

Figure 11:
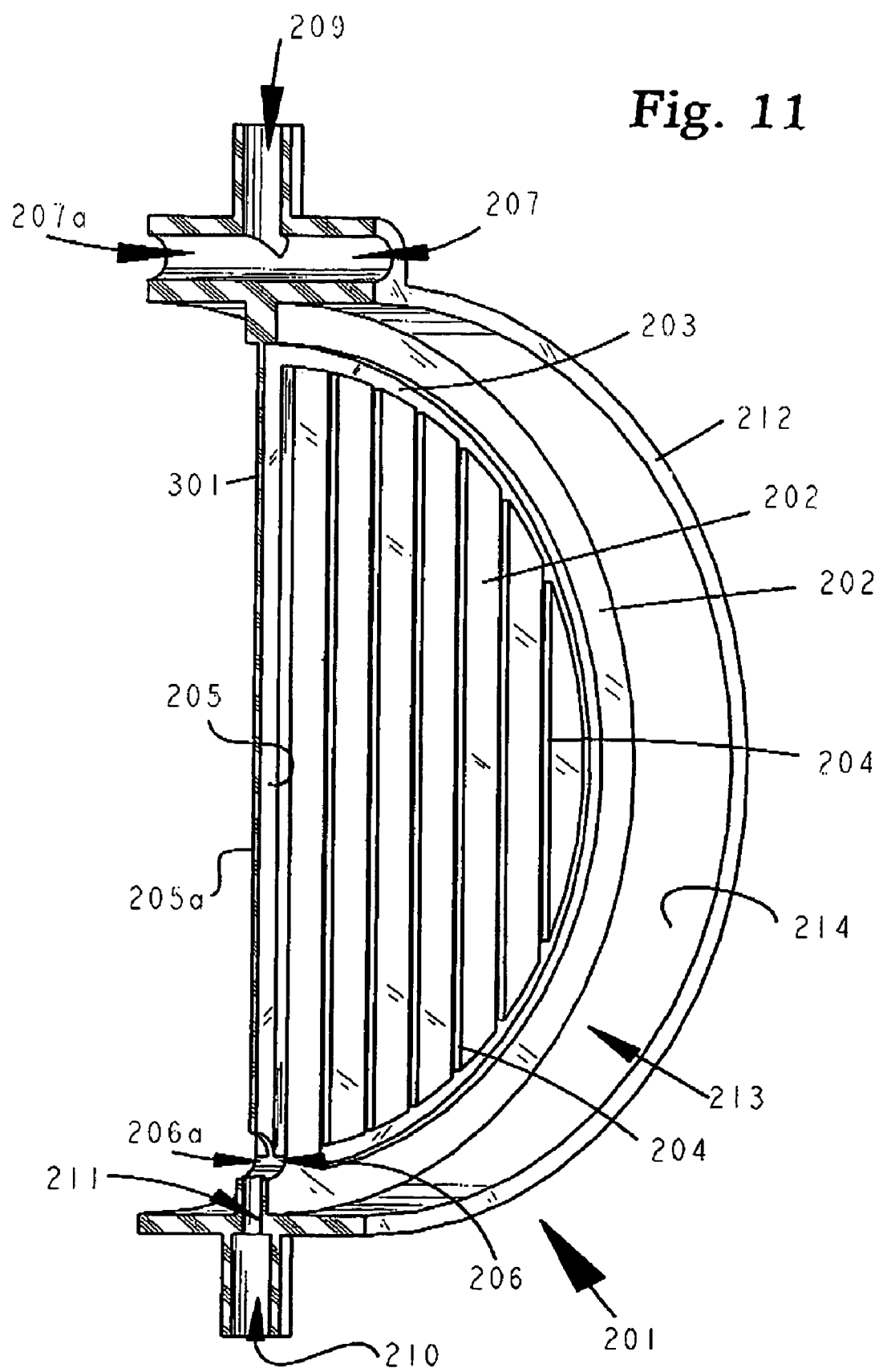
FIG. 11 is a front isometric view having portions thereof removed of the body of the filtration apparatus depicted in FIG. 17.

FIG. 10A, FIG. 11, and FIG. 12A show the front part of body 201. The front part of body 201 contains a first filter well 213, defined by flat surface 202 of partition wall 301 and cylindrical surface 214. The front part of body 201 also contains side vertical channels 204, circular channel 203, and center vertical channel 205. Preferably circular channel 203 is wider and deeper than side vertical channels 204, and center vertical channel 205 is wider than circular channel 203, and the same depth as circular channel 203. The upper and lower ends of side vertical channels 204 are in fluid flow relation with circular channel 203, and circular channel 203 is in fluid flow relation with center vertical channel 205. Center vertical channel 205 is in fluid flow relation with front outlet port 206. The upper central part of body 201 contains inlet tube socket 217, and cross protrusion 219. Inlet tube socket 217 contains inlet port 209, and cross protrusion 219 contains a cross port, with the front half of the cross port labeled front cross port 207, and the back half of the cross port labeled back cross port 207a. The lower central part of body 201 contains outlet tube socket 218. Outlet tube socket 218 contains outlet port 210. Front outlet port 206 is in fluid flow relation with outlet port 210 through link port 211.

FIG. 10B, and FIG. 12B show the back part of body 201. The back part of body 201 contains a second filter well 213a, defined by flat surface 202a of partition wall 301 and cylindrical surface 214a. The back part of body 201 also contains side vertical channels 204a, circular channel 203a, and center vertical channel 205a. Preferably circular channel 203a is wider and deeper than side vertical channels 204a, and center vertical channel 205a is wider than circular channel 203a, and the same depth as circular channel 203a. The upper and lower ends of side vertical channels 204a are in fluid flow relation with circular channel 203a, and circular channel 203a is in fluid flow relation with center vertical channel 205a. Center vertical channel 205a is in fluid flow relation with back outlet port 206a. The upper central part of body 201 contains inlet tube socket 217, and cross protrusion 219. Inlet tube socket 217 contains inlet port 209, and cross protrusion 219 contains a cross port, with the front half of the cross port labeled front cross port 207, and the back half of the cross port labeled back cross port 207a. The lower central part of body 201 contains outlet tube socket 218. Outlet tube socket 218 contains outlet port 210. Back outlet port 206a is in fluid flow relation with outlet port 210 through link port 211. Front outlet port 206 is a through hole with the front half labeled front outlet port 206, and the back half labeled back outlet port 206a. As shown in FIG. 10A, FIG. 10B, FIG. 12A and FIG. 12B the back part of body 201 is a mirror image of the front part of body 201. Body 201 is preferably made from an injection moldable medical grade plastic such acrylic, polycarbonate, polysulfone, polypropylene, polyethylene, but is not limited to these materials.

Figure 14:
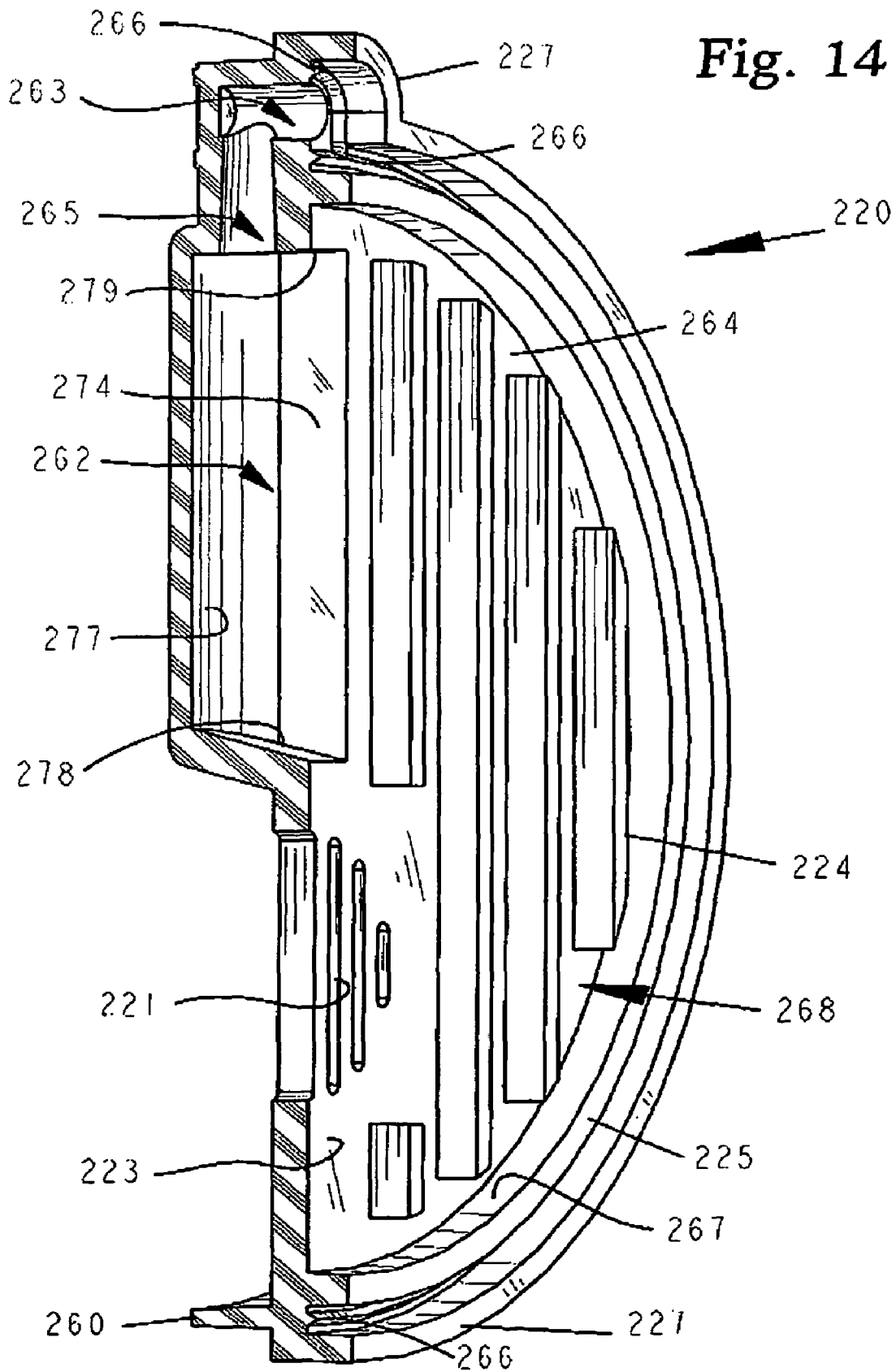
FIG. 14 is a front isometric view having portions thereof removed of the front cover of the filtration apparatus depicted in FIG. 17.
Figure 18:
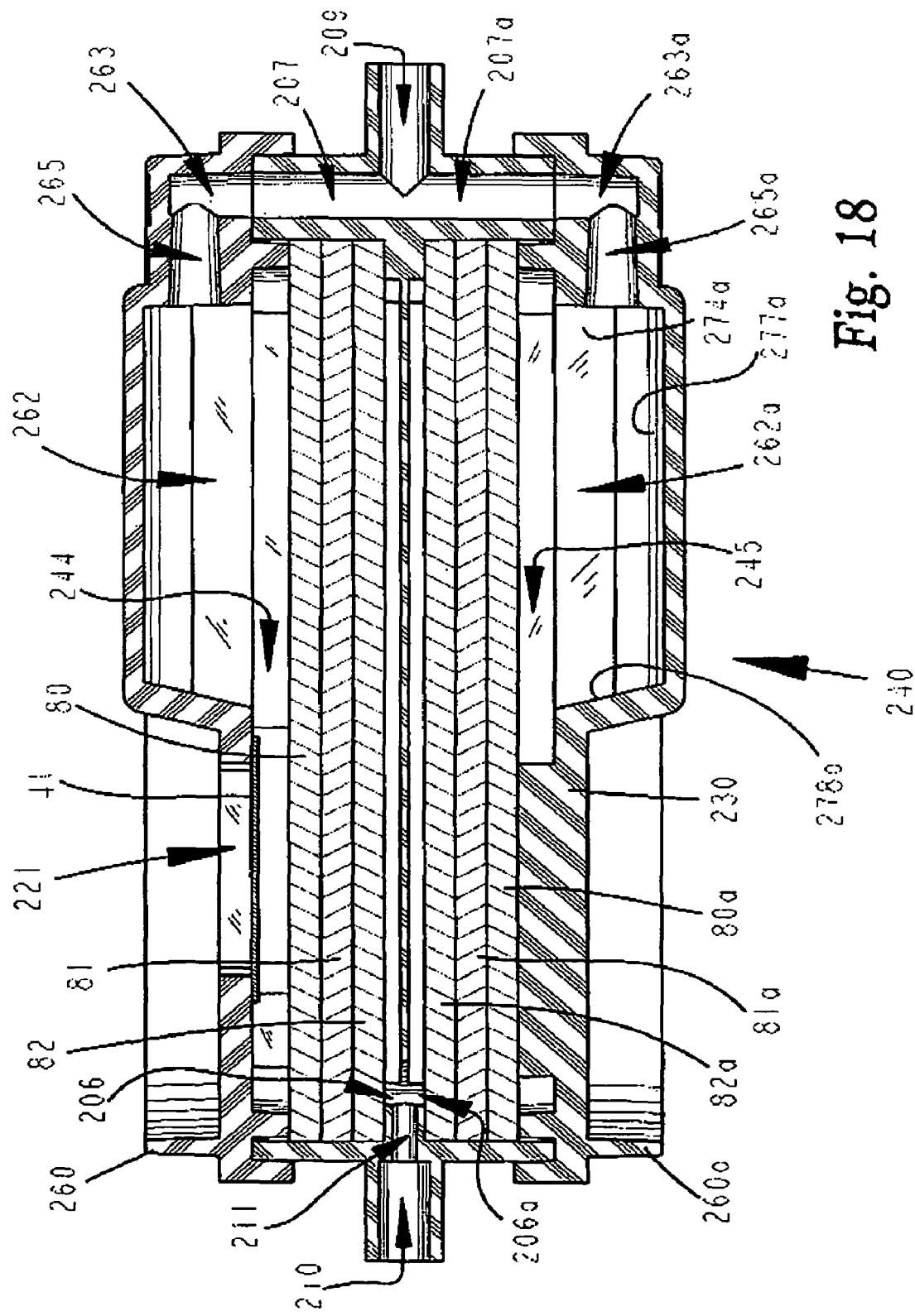
FIG. 18 is a cross-sectional view of the filtration apparatus depicted in FIG. 17.

FIG. 13A, FIG. 13B, and FIG. 14 show front cover 220. Front cover 220 is round in shape to match the shape of body 201, (if body 201 was square, then front cover 220 would also be square) and contains boss 229 at its upper end. The interior of front cover 220 contains flat surface 223. Vertical filter support ribs 224 protrude from flat surface 223. The vertical filter support ribs 224 could be replaced with ribs oriented in a direction other than vertical, or with a pattern of round pins, or with a pattern or rectangular pins, or with a pattern of concentric rings with gaps in the rings, or with any other filter support means that does not contain a closed loop. Outer rib 227 also protrudes from flat surface 223 and follows the outer periphery of front cover 220. Although it is not necessary for front cover 220 to contain outer rib 227, outer rib 227 acts as an alignment rib during assembly, and as a flash trap to contain flash when front cover 220 is assembled to body 201. Front cover 220 also contains round filter support rib 225. Round filter support rib 225 does not contain a gap, as round filter support rib 25 of front cover 20 of the first embodiment does. Front cover 220 also contains through slots 221, and vent filter bonding area 228. Although filter bonding area 228 is shown round for bonding a round vent filter, the vent filter could be square or any other shape, and then the filter bonding area 228 would conform to the shape of the vent filter. Through slots 221 are shown as vertical slots, they could be replaced by a pattern of round holes, or a pattern of square holes, or any other pattern of through holes that provide adequate filter support, and also provide air flow communication between the face of the vent filter that is bonded to flat surface 223, and to the outside atmosphere of front cover 220. Referring to FIG. 13B, FIG. 14, and FIG. 18, front cover 220 contains chamber 262 bounded by side walls 274, top wall 277, end wall 278, and end wall 279. Front cover 220 also contains port 263 and port 265. Port 263 is in fluid flow and air flow communication with chamber 262 through port 265. Referring to FIG. 14, front cover 220 contains energy director 266 if it is desired to bond front cover 220 to body 201 using an energy director ultrasonic weld. FIG. 18 shows vent filter element 41 bonded to front cover 220. Referring to FIG. 16, centerline 270 shows the center of the seal between front cover 220 and body 201. The seal could be an ultrasonic weld, a glue bond, a heat bond, a solvent bond, or any other type of leak tight bond. Referring to FIG. 13A, the outside of front cover 220 contains flat surface 222. Front cover 220 also contains weld rib 260 which protrudes above flat surface 222. The centerline of weld rib 260 is a mirror image of centerline 270, the center of the seal between front cover 220 and body 201. The outside of front cover 220 also contains protrusion 261, the outer wall of chamber 262 and port 265. Weld rib 260 is used to transmit sonic energy from a flat ultrasonic horn to energy director 266 (shown in FIG. 14) of front cover 220 during the process of welding front cover 220 to body 201, when an ultrasonic weld is used. Front cover 220 is preferably made from an injection moldable medical grade plastic such acrylic, polycarbonate, polysulfone, polypropylene, polyethylene, but is not limited to these materials. Front cover 220 is preferably made from the same material that body 201 is made of.

FIG. 15A, and FIG. 15B, show back cover 230. Back cover 230 is round in shape to match the shape of body 201, (if body 201 was square, then back cover 230 would also be square) and contains boss 239 at its upper end. The interior of back cover 230 contains flat surface 233. Vertical filter support ribs 234 protrude from flat surface 233. The vertical filter support ribs 234 could be replaced with ribs oriented in a direction other than vertical, or with a pattern of round pins, or with a pattern or rectangular pins, or with a pattern of concentric rings with gaps in the rings, or with any other filter support means that does not contain a closed loop. Outer rib 237 also protrudes from flat surface 233 and follows the outer periphery of back cover 230. Although it is not necessary for back cover 230 to contain outer rib 237, outer rib 237 acts as an alignment rib during assembly, and as a flash trap to contain flash when back cover 230 is assembled to body 201. Back cover 230 also contains round filter support rib 235. Round filter support rib 235 does not contains a gap, as round filter support rib of back cover 30 of the first embodiment does. Referring to FIG. 15A, FIG. 15B, and FIG. 18, back cover 230 contains chamber 262*a* bounded by side walls 274*a*, top wall 277*a*, end wall 278*a*, and end wall 279*a*. Back cover 230 also contains port 263*a* and port 265*a*. Port 263*a* is in fluid flow and air flow communication with chamber 262*a* through port 265*a*. Back cover 230 also contains an energy director 266*a* (not shown, like energy director 266 of front cover 220) if it is desired to bond back cover 230 to body 201 using an energy director ultrasonic weld. Back cover 230 seals to body 201 along a center line like centerline 270 shown in FIG. 16 for front cover 220. The seal could be an ultrasonic weld, a glue bond, a heat bond, a solvent bond, or any other type of leak tight bond. Referring to FIG. 15A, the outside of back cover 230 contains flat surface 232. Back cover 230 also contains weld rib 260*a* which protrudes above flat surface 232. The centerline of weld rib 260*a* is a mirror image of centerline 270, the center of the seal between back cover 230 and body 201. The outside of back cover 230 also contains protrusion 261*a*, the outer wall of chamber 262*a* and port 265*a*. Weld rib 260*a* is used to transmit sonic energy from a flat ultrasonic horn to energy director 266*a* of back cover 230 during the process of welding back cover 230 to body 201, when an ultrasonic weld is used. Back cover 230 is preferably made from an injection moldable medical grade plastic such acrylic, polycarbonate, polysulfone, polypropylene, polyethylene, but is not limited to these materials. Back cover 230 is preferably made from the same material that body 201 is made of. Back cover 230 is identical to front cover 220 with the exception that back cover 230 does not contain a vent filter.

Figure 19:
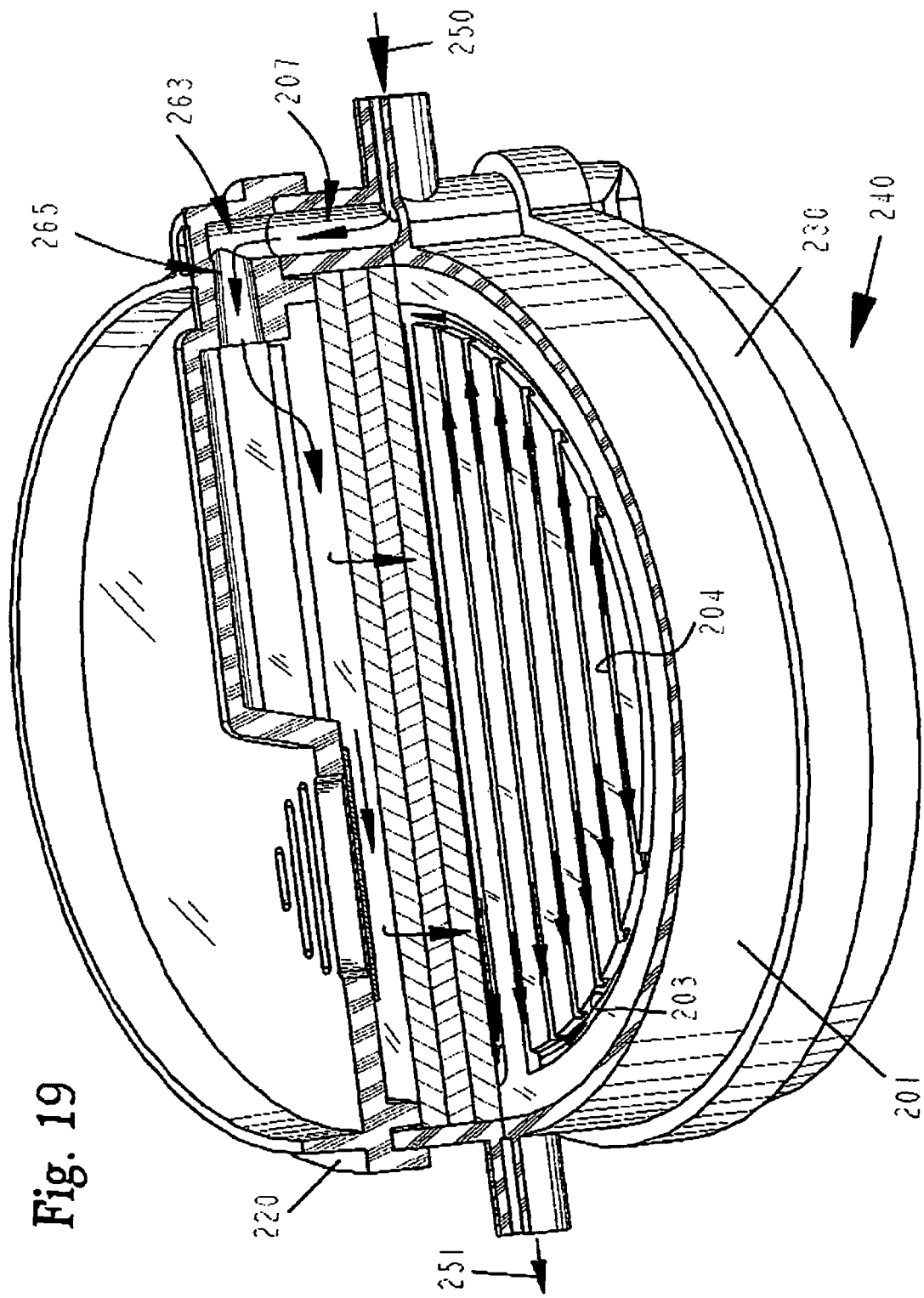
FIG. 19 is an isometric view of the filtration apparatus depicted in FIG. 17, having portions thereof removed.

FIG. 17 shows an exploded view of the components that comprise filter device 240. The components are body 201, front cover 220, back cover 230, vent filter element 41, and filter elements 80, 81, and 82, and filter elements 80*a*, 81*a*, and 82*a*. FIG. 18 and FIG. 19 show filter device 240 in the assembled state. Referring to FIG. 10A, FIG. 10B, FIG. 11, FIG. 13B, FIG. 14 FIG. 15B, FIG. 16, FIG. 17, FIG. 18, and FIG. 19, the components that comprise filter device 240 are assembled as follows. The outer periphery of vent filter element 41 is sealed to front cover 220 at filter bonding area 228. The seal is preferably a heat seal but could be an ultrasonic seal, a glue bond, a solvent bond, or any other type of bond that will produce a leak tight seal capable of maintaining sterility. Filter element 41 is a hydrophobic filter with a pore size of $0.2\mu$ or smaller to maintain sterility. Filter elements 80, 81, and 82 are placed into first filter well 213. Front cover 220 is then bonded to body 201 so that edge 212 of body 201 is bonded to front cover 220 along centerline 270 shown in FIG. 16. The seal between front cover 220 and body 201 forms a double closed loop. The first closed loop encloses the outer periphery of first filter well 213 of body 201, thereby creating a closed first chamber 244 in first filter well 213. The second closed loop encloses the outer periphery of front cross port 207, and the outer periphery of port 263, thereby creating a flow path from inlet port 209, through front cross port 207, through port 263, through port 265, into chamber 262, into first chamber 244 of first filter well 213. If first chamber 244 is made deeper chamber 262 may be eliminated, and the flow path would flow from inlet port 209, through front cross port 207, through port 263, through port 265, into first chamber 244. Outer rib 227 of front cover 220 aligns front cover 220 to body 201 during the assembly procedure and also acts as a flash trap. The bond between front cover 220 and body 201 is preferably an ultrasonic seal but could be a glue bond, a heat bond, a solvent bond or any other type of bond that creates a leak tight seal. Filter elements 80, 81, and 82 are sealed to body 201 with a compression seal between the outer edges 84, 85, and 86 of filter elements 80, 81, and 82 respectively, and cylindrical surface 214 of body 201 in the filter device 240 shown. This seal could be augmented or replaced by a compression seal created by compressing the outer periphery of filter elements 80, 81, and 82 between round filter support rib 225 of front cover 220 and flat surface 202 of body 201. Filter elements 80, 81, and 82 also could be sealed to body 201 with a glue seal, a heat seal, or any other type of seal that eliminates bypass around filter elements 80, 81, and 82. Filter device 240 is shown with 3 filter elements 80, 81, and 82 in first filter well 213. However any number of filter elements greater than or equal to one could be used. The number of filter elements used is determined by the filter type and the fluid being filtered. The same number of filter elements that were placed into first filter well 213 of body 201 are now placed into second filter well 213*a* of body 201, and are designated as filter elements 80*a*, 81*a*, and 82*a*. These filter elements are sealed to body 201 using the same method that was used to seal filter elements 80, 81, and 82 to first filter well 213. Back cover 230 is then bonded to body 201 so that edge 212*a* of body 201 is bonded to back cover 230 along the same path as centerline 270 shown in FIG. 16. The seal between back cover 230 and body 201 forms a double closed loop. The first closed loop encloses the outer periphery of second filter well 213*a* of body 201, thereby creating a closed first chamber 245 in second filter well 213*a*. The second closed loop encloses the outer periphery of back cross port 207*a*, and the outer periphery of port 263*a*, thereby creating a flow path from inlet port 209, through back cross port 207*a*, through port 263*a*, through port 265*a*, into chamber 262*a*, into first chamber 245 of second filter well 213*a*. If first chamber 245 is made deeper chamber 262*a* may be eliminated, and the flow path would flow from inlet port 209, through back cross port 207*a*, through port 263*a*, through port 265*a*, into first chamber 245. Outer rib 237 of back cover 230 aligns back cover 230 to body 201 during the assembly procedure and also acts as a flash trap. The bond between back cover 230 and body 201 is preferably an ultrasonic seal but could be a glue bond, a heat bond, a solvent bond or any other type of bond that creates a leak tight seal.

Referring to FIG. 13B, FIG. 17, FIG. 18, and FIG. 19, the assembled filter device 240 contains first chamber 244 bounded by flat surface 223 of front cover 220, inner surface 277 of round filter support rib 225 of front cover 220, and the upstream surface 46 of the first filter element 80 in first filter well 213 of body 201. Referring to FIG. 15B, FIG. 17, and FIG. 18, the assembled filter device 240 also contains first chamber 245 bounded by flat surface 233 of back cover 230, inner surface 271 of round rib 235 of back cover 230, and the upstream surface 46a of the first filter element 80a in second filter well 213a of body 201. Referring to FIG. 18, in the assembled filter device 240, front cross port 207 of body 201 is in fluid flow communication and air flow communication with first chamber 244 through port 263, port 265, and chamber 262 of front cover 220. Referring to FIG. 18, in the assembled filter device 240, back cross port 207a of body 201 is in fluid flow communication and air flow communication with first chamber 245 through port 263a, port 265a, and chamber 262a of back cover 220.

Referring to FIG. 10a, FIG. 14, FIG. 17 and FIG. 18, the assembled filter device 240 contains second chamber 247 of first filter well 213 bounded by the downstream surface 48 of the last filter element 82 in first filter well 213 of body 201, and by center vertical channel 205, circular channel 203, and side vertical channels 204. Second chamber 247 of first filter well 213 contains front outlet port 206. Referring to FIG. 10b, FIG. 17 and FIG. 18, the assembled filter device 240 contains second chamber 247a of second filter well 213a bounded by the downstream surface 48a of the last filter element 82a in second filter well 213a of body 201, and by center vertical channel 205a, circular channel 203a, and side vertical channels 204a. Second chamber 247a of second filter well 213a contains back outlet port 206a.

Figure 20:
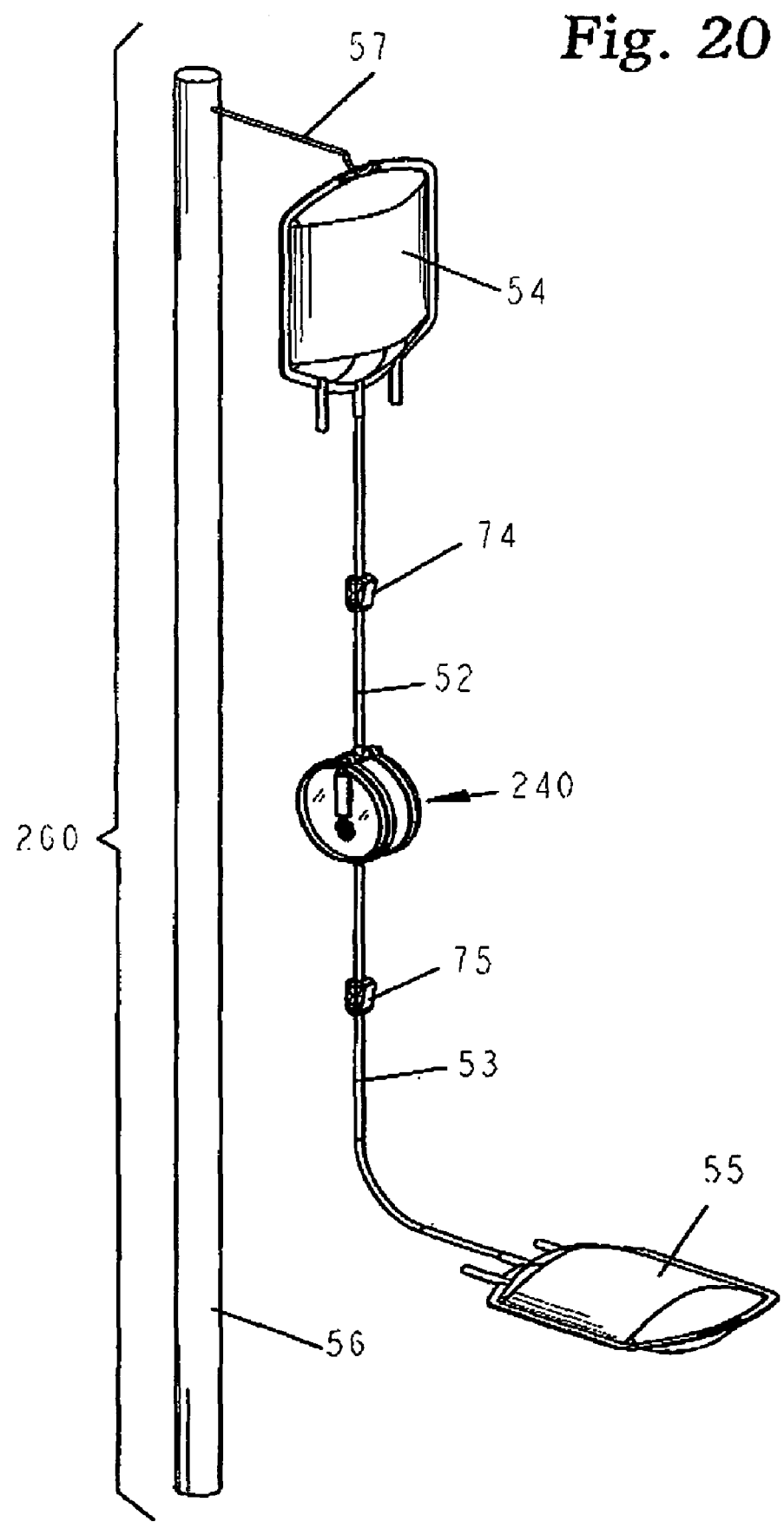
FIG. 20 is an isometric view of a blood filtration assembly containing the filtration apparatus depicted in FIG. 17.

Referring to FIG. 20 one end of a length of outlet tubing 53 is bonded to outlet tube socket 218 of body 201, with the other end of said outlet tubing bonded to an empty blood bag 55. Another length of inlet tubing 52 is bonded to inlet tube socket 217 of body 201. The end user will purchase the assembly of filter device 240, inlet tubing 52, outlet tubing 53, and receiving blood bag 55, assembled and sterile. The assembly will also contain an inlet tubing clamp 74 on inlet tubing 52, and an outlet tubing clamp 75 on outlet tubing 53.

In FIG. 20 the filter device 240 is in an operational assembly with inlet tubing 52, outlet tubing 53, feed blood bag 54, receiving blood bag 55, inlet tube clamp 74, and outlet tube clamp 75. Preferably, the user will purchase the assembly of FIG. 20 sterilized without feed blood bag 54 with the inlet end of inlet tubing 52 sealed to maintain system sterility. For performing filtration the user will first close inlet tube clamp 74 close to the inlet end of inlet tubing 52. Next the user will make sure that outlet tube clamp 75 is open. Inlet tubing 52 is now bonded by the user to a pigtail on feed blood bag 54 using a sterile docking device as is well known in the art.

Once the sterile docking connection is made the user will hang feed blood bag 54 from hook 57 on blood bag pole 56. Receiving blood bag 55 should be placed on a surface such as a table top or the like. The complete assembly 260 ready for filtration is illustrated in FIG. 20.

Referring to FIG. 10A, FIG. 10B, FIG. 18, FIG. 19 and FIG. 20 the filtration is performed as follows. The user opens inlet tube clamp 74. Gravity now forces blood to flow from feed blood bag 54, through inlet tubing 52, through inlet port 209 of body 201. After passing through inlet port 209, a portion of the blood passes through front cross port 207, while the remainder of the blood passes through back cross port 207a. The portion of the blood that passes through front cross port 207, then passes through port 263, through port 265, into chamber 262, and then into first chamber 244. The portion of the blood that passes through back cross port 207a, then passes through port 263a, through port 265a, into chamber 262a, and then into first chamber 245. A portion of the air that was in inlet tubing 52 and inlet port 209 before blood flow started will be pushed ahead of the blood, through front cross port 207, through port 263, through port 265, into chamber 262, and then into first chamber 244. The remainder of the air that was in inlet tubing 52 and inlet port 9 before blood flow started will be pushed ahead of the blood, through back cross port 207a, through port 263a, thorough port 265a, into chamber 262a, and then into first chamber 245. Because the usable surface area of hydrophobic filter 41 is much smaller than the usable surface area of filter elements 80, 81, and 82; and because the pressure drop across sterilizing grade hydrophobic filter 41 is much greater per unit volume of air flow per unit surface area of filter material than the combined pressure drop across filter elements 80, 81, and 82 per unit volume of air flow per unit surface area of filter material, only a very small portion of the air that was in inlet tubing 52, inlet port 9, front cross port 207, port 263, and port 265 before blood flow started, will pass through hydrophobic filter 41, and then through slots 221 of front cover 220 to atmosphere.

As first chamber 244 fills from the bottom up most of the air in first chamber 244 and in chamber 262 will be forced through filter elements 80, 81, and 82, for the same reasons described in the previous paragraph. This initial air will flow into vertical channels 204, circular channel 203, and center vertical channel 205, and then flow through front outlet port 206, through link port 211, through outlet port 210, into outlet tubing 53, into receiving blood bag 55. Filter elements 80, 81, and 82 will also wet from the bottom up. The air that is initially in filter elements 80, 81, and 82 will be displaced by blood and flow into vertical channels 204, circular channel 203, and center vertical channel 205, and then flow through front outlet port 206, through link port 211, through outlet port 210, into outlet tubing 53, into receiving blood bag 55. Because the combined volume of first chamber 244 and chamber 262 is small, and the flow rate of blood entering first chamber 244 is much greater than the initial flow rate of blood through filter elements 80, 81, and 82, first chamber 244 will fill in a small fraction of the time that it takes to wet filter elements 80, 81, and 82. The pressure head at the bottom of first chamber 244 will be larger than the pressure head at the top of chamber 244, because of the height difference between the top and bottom of first chamber 244. Therefore liquid will start to come through filter element 82 from the bottom up. As liquid starts to come through filter element 82 from the bottom up vertical channels 204, circular channel 203, and center vertical channel 205, of body 201 will fill from the bottom up. Because the total volume of these channels in is small (to minimize holdup) the channels may fill with blood (from the bottom up) before the upper part of filter element 82 has wet with blood. Once a sufficient quantity of blood flows from center vertical channel 205 of body 201, into front outlet port 206 of body 201, through link port 211 of body 201, into outlet tubing 53, and flows down outlet tubing 53 toward receiving blood bag 55, the pressure in front outlet port 206 will become negative. Because center vertical channel 205 is in fluid flow relationship with front outlet port 206, the pressure inside the tube created by center vertical channel 205 and downstream surface 48 of filter element 82 will also be negative. Likewise since circular channel 203 is in fluid flow relationship with center vertical channel 205 the pressure inside the tube created by circular channel 203 and downstream surface 48 of filter element 82 will also be negative. Since the tube segments made up of vertical channels 204 and downstream surface 48 of filter element 82 are in fluid flow relationship with the tube created by circular channel 203 and downstream surface 48 of filter element 82, any air or liquid that flows from filter element 82 into vertical channels 204 after the pressure in the front outlet port becomes negative, will be sucked into circular channel 203, and then flow from circular channel 203 into center vertical channel 205, through front outlet port 206, through link port 211, through outlet port 210, into outlet tubing 53, and into receiving blood bag 55. This assures that filter elements 80, 81, and 82 will completely wet, and that all of the air that was in first chamber 244 and chamber 262, filter elements 80, 81, and 82, vertical channels 204, circular channel 203, center circular channel 205, front outlet port 206, link port 211, outlet port 210, and the interior of outlet tubing 53 will be forced into receiving blood bag 55. Although vertical channels 204 are shown in the vertical orientation, they could be orientated at any angle from zero degrees to ninety degrees from vertical, as long as they are in fluid flow relationship with circular channel 3. Other channel designs such as the spiral channel filter underdrain disclosed in U.S. Ser. No. 08/524,049, and entitled "an In-Line Liquid Filtration Device Usable for Blood, Blood Products and the Like", could also be used in place of the design illustrated in FIG. 10A. It is however, imperative that all channels be either directly or indirectly in fluid flow relationship with front outlet port 206.

The portion of blood from feed blood bag 54 which flows through back cross port 7a, through port 263a, through port 265a, into chamber 262a, into first chamber 245, will fill first chamber 245 from the bottom up forcing all of the air in first chamber 45 and chamber 262a through filter elements 80a, 81a, and 82a. This initial air will flow into vertical channels 204a, circular channel 203a, and center vertical channel 205a, and then flow through back outlet port 206a, through link port 211, through outlet port 210, into outlet tubing 53, into receiving blood bag 55. Filter elements 80a, 81a, and 82a will also wet from the bottom up. The air that is initially in filter elements 80a, 81a, and 82a will be displaced by blood and flow into vertical channels 204a, circular channel 203a, and center vertical channel 205a, and then flow through outlet port 206a, through link port 211, through outlet port 210, into outlet tubing 53, into receiving blood bag 55. Because the combined volume of first chamber 245 and chamber 262a is small, and the flow rate of blood entering chamber 262a and first chamber 245 is much greater than the initial flow rate of blood through filter elements 80a, 81a, and 82a, first chamber 245 and chamber 262a will fill in a small fraction of the time that it takes to wet filter elements 80a, 81a, and 82a. The pressure head at the bottom of first chamber 245 will be larger than the pressure head at the top of first chamber 245, because of the height difference between the top and bottom of first chamber 245. Therefore liquid will start to come through filter element 82a from the bottom up. As liquid starts to come through filter element 82a from the bottom up vertical channels 204a, circular channel 203a, and center vertical channel 205a, of body 201 will fill from the bottom up. Because the total volume of these channels in is small (to minimize holdup) the channels may fill with blood (from the bottom up) before the upper part of filter element 82a has wet with blood. Once a sufficient quantity of blood flows from center vertical channel 205a of body 201, into back outlet port 206a of body 201, through link port 211 of body 201, into outlet tubing 53, and flows down outlet tubing 53 toward receiving blood bag 55, the pressure in back outlet port 206a will become negative. Because center vertical channel 205a is in fluid flow relationship with back outlet port 206a, the pressure inside the tube created by center vertical channel 205a and the downstream surface 48a of filter element 82a will also be negative. Likewise since circular channel 203a is in fluid flow relationship with center vertical channel 205a the pressure inside the tube created by circular channel 203a and the downstream surface 48a of filter element 82a will also be negative. Since the tube segments made up of vertical channels 204a and the downstream surface 48a of filter element 82a are in fluid flow relationship with the tube created by circular channel 203a and the downstream surface 48a of filter element 82a, any air or liquid that flows from filter element 82a into vertical channels 204a after the pressure in the back outlet port becomes negative will be sucked into circular channel 203a, and then flow from circular channel 203a into center vertical channel 205a, through back outlet port 206a, through link port 211, through outlet port 210, into outlet tubing 53, and into receiving blood bag 55. This assures that filter elements 80a, 81a, and 82a will completely wet, and that all of the air that was in chamber 245, chamber 262a, filter elements 80a, 81a, and 82a, vertical channels 204a, circular channel 203a, center vertical channel 205a, back outlet port 206a, link port 211, outlet port 210, and the interior of outlet tubing 53 will be forced into receiving blood bag 55. Although vertical channels 204a are shown in the vertical orientation, they could be orientated at any angle from zero degrees to ninety degrees from vertical, as long as they are in fluid flow relationship with circular channel 203a. Other channel designs such as the spiral channel filter underdrain disclosed in U.S. Ser. No. 08/524,049, and entitled "an In-Line Liquid Filtration Device Usable for Blood, Blood Products and the Like", could also be used in place of the design illustrated in FIG. 10B. It is however, imperative that all channels be either directly or indirectly in fluid flow relationship with back outlet port 206a.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in front outlet port 206, and the pressure head in back outlet port 206a will be negative, as will be the pressure head in vertical channels 204, circular channel 203, center vertical channel 205, vertical channels 204a, circular channel 203a, and center vertical channel 205a, all of body 201. Once blood flow has stopped the pressure drop across filter elements 80, 81, and 82, will fall to zero. The pressure drop across filter elements 80a, 81a, and 82a, will also fall to zero. Hence the pressure in first chamber 244 and chamber 262, and the pressure in first chamber 245 and chamber 262a will become negative. Once the pressure in chamber 244 and chamber 262 falls below atmospheric pressure air will begin to flow from atmosphere through slots 221, through sterilizing grade hydrophobic filter 41, into first chamber 244. The sterile air that enters first chamber 244 will bubble up to the top of first chamber 244 and chamber 262, thus causing first chamber 244 and chamber 262 to drain from the top down. Because of the negative pressure in first chamber 245, some of the air that bubbles to the top of first chamber 244 will pass through port 265, through port 263, through front cross port 207, through back cross port 207a, through port 263a, through port 265a, into chamber 262a and first chamber 245, causing chamber 262a and first chamber 245 to drain from the top down, and causing the blood in port 263 and port 265 to drain into chamber 262, and causing the blood in port 263a and port 265a to drain into chamber 262a, and causing the blood in front cross port 207 and back cross port 207a to drain into both chamber 262 and chamber 262a. Because the air entering first chamber 244 bubbles to the top of first chamber 244 and to the top of chamber 262, thus draining first chamber 244 and chamber 262 from the top down, vent filter element 41 can be located anywhere on flat surface 223 of front cover 220. Filter elements 80, 81, 82, 80a, 81a, and 82a will be plugged sufficiently at this point, therefore very little if any blood will be sucked from these filter elements by the negative pressure in front outlet port 206, and by the negative pressure in back outlet port 206a. Hence blood flow will stop after first chamber 244 and chamber 262, and after first chamber 245 and chamber 262a have drained and blood will remain in filter elements 80, 81, 82, 80a, 81a, and 82a, and in vertical channels 204, circular channel 203, center vertical channel 205, vertical channels 204a, circular channel 203a, and center vertical channel 205a, and in front outlet port 206, back outlet port 206a, link port 211, outlet port 210, all of body 201, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 240 can now be discarded in a safe manner. Outlet tubing 53 will have segments marked on it. The user can now seal the tubing at the segment marks. The blood that is left in outlet tubing 53 will be used for cross matching and for quality control purposes.

Referring to FIG. 10A, FIG. 10B, FIG. 13B, FIG. 15B, and FIG. 18, front cover 220 and back cover 230 of filter device 240 provide a 360° continuous filter compression seal via round filter support rib 225 and round filter support rib 235 respectively. Because unfiltered blood enters chamber 262 and first chamber 244 on the inside of round filter support rib 225, unfiltered blood is prevented from entering the gap between the outside of round filter support rib 225 of front cover 220 and cylindrical surface 214 of body 201. Likewise, unfiltered blood enters chamber 262a and first chamber 245 on the inside of round filter support rib 235, thus unfiltered blood is prevented from entering the gap between the outside of round filter support rib 235 of back cover 230 and cylindrical surface 214a of body 201. Hence the fifth embodiment of the present invention overcomes the shortcomings of the first two embodiments of the present invention, with the added benefit that the two filter compression rings of the third embodiment are not required in the fifth embodiment.

Referring to FIG. 11, with front outlet port 206 and back outlet port 206a at the very bottom of center vertical channels 205 and 205a respectively, the length of link port 211 is minimized, thereby minimizing the diameter of the pin (a minimum diameter is needed to prevent breakage of the pin) in the injection mold, thereby minimizing the wall thickness of partition wall 301 of body 201, thereby reducing the cost of body 201.

A sixth embodiment of the filtration device constructed in accordance with the principles of the present invention, could be constructed by replacing the back cover 230 of the fifth embodiment with a second front cover 220. The sixth embodiment would work the same as the fifth embodiment, with the exception that after the feed blood bag is empty, air would enter first chamber 245 and chamber 262a from the vent filter on the front cover 220 that replaces the back cover 230.

Figure 28A:
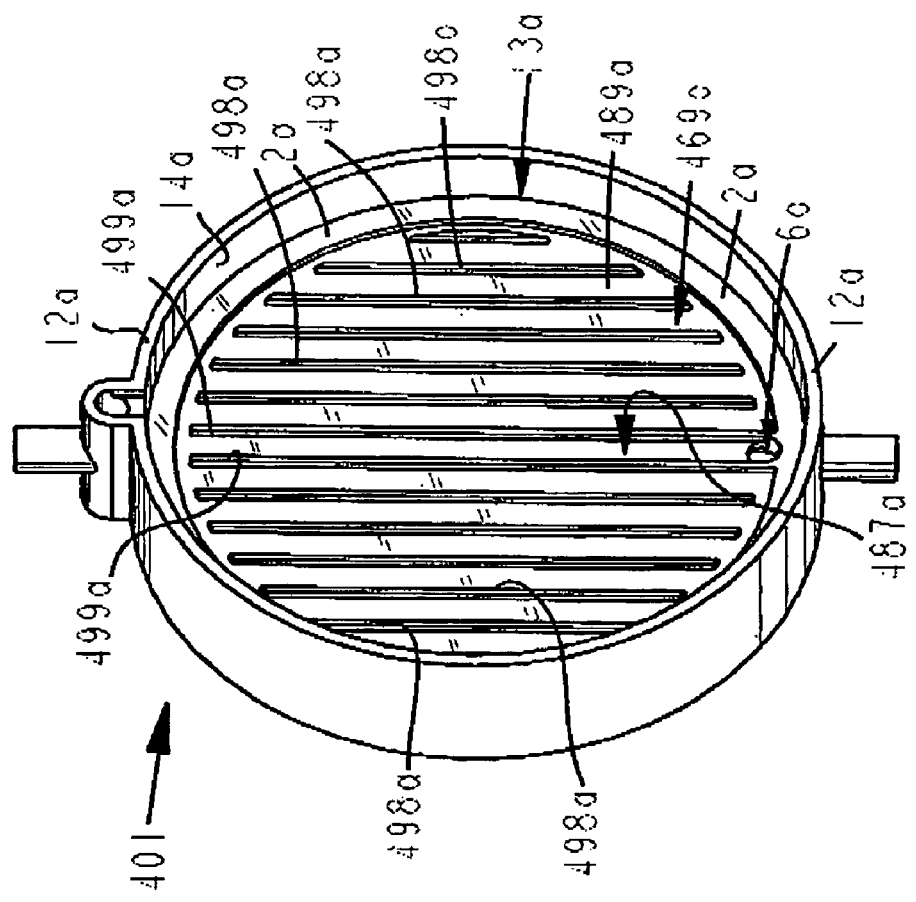
FIG. 28A is a front isometric view of the body of the filtration apparatus depicted in FIG. 30.
Figure 28B:
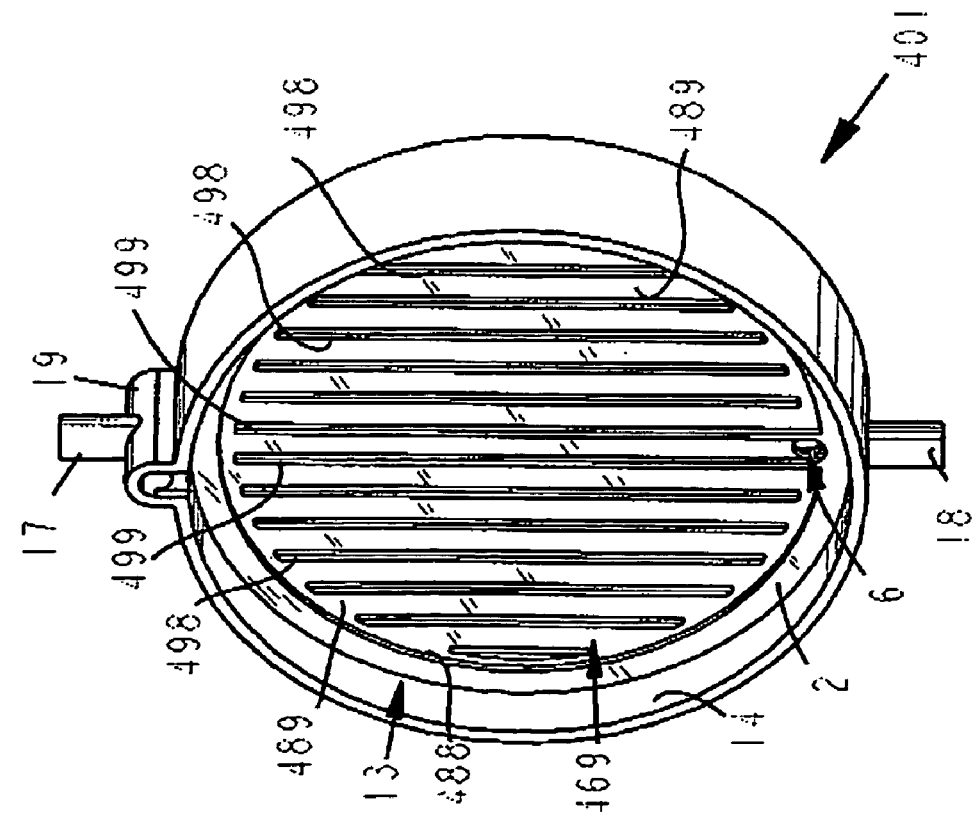
FIG. 28B is a back isometric view of the body of the filtration apparatus depicted in FIG. 30.
Figure 29:
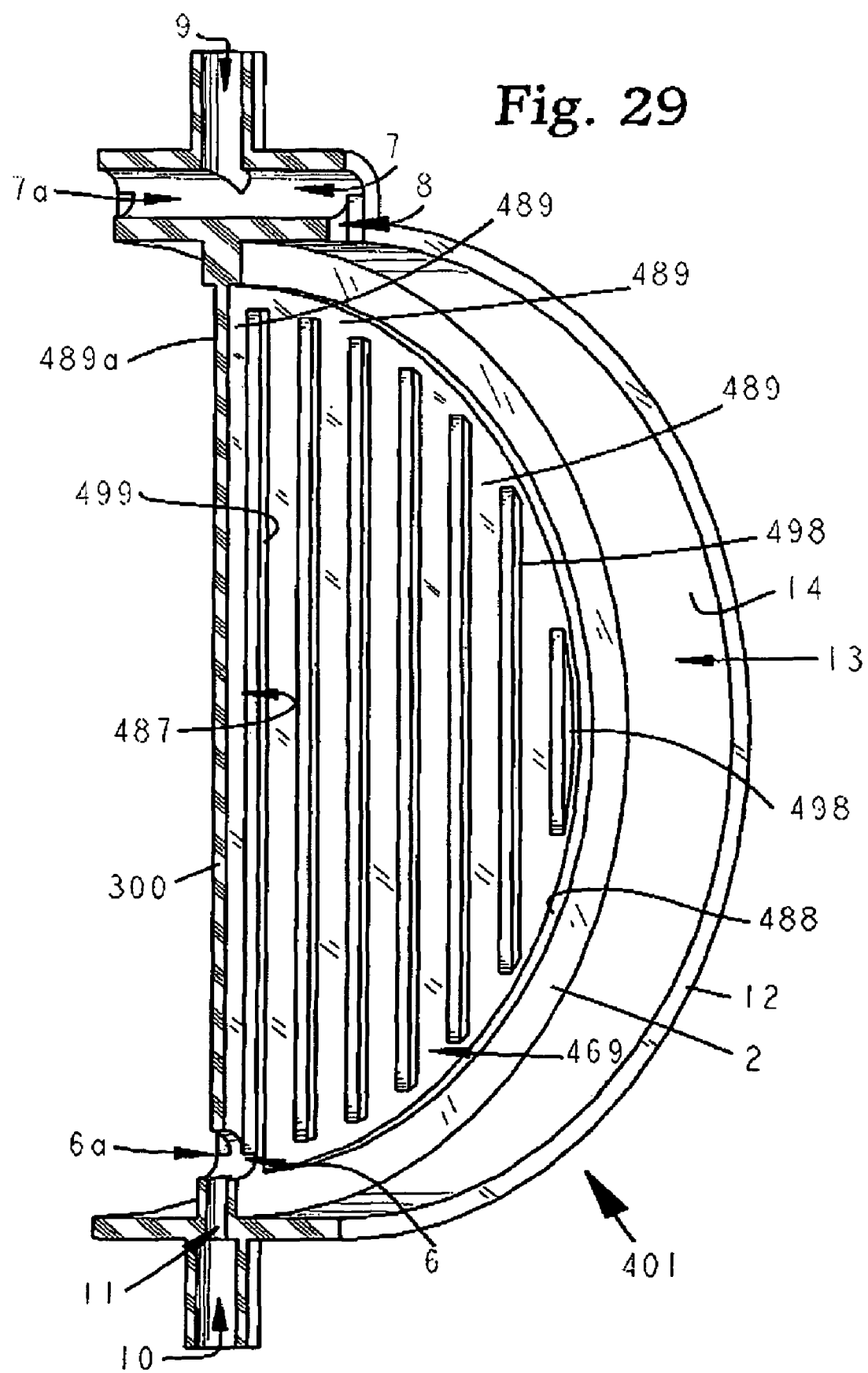
FIG. 29 is an isometric view, having portions thereof removed, of the body of the filtration apparatus depicted in FIG. 30.
Figure 30:
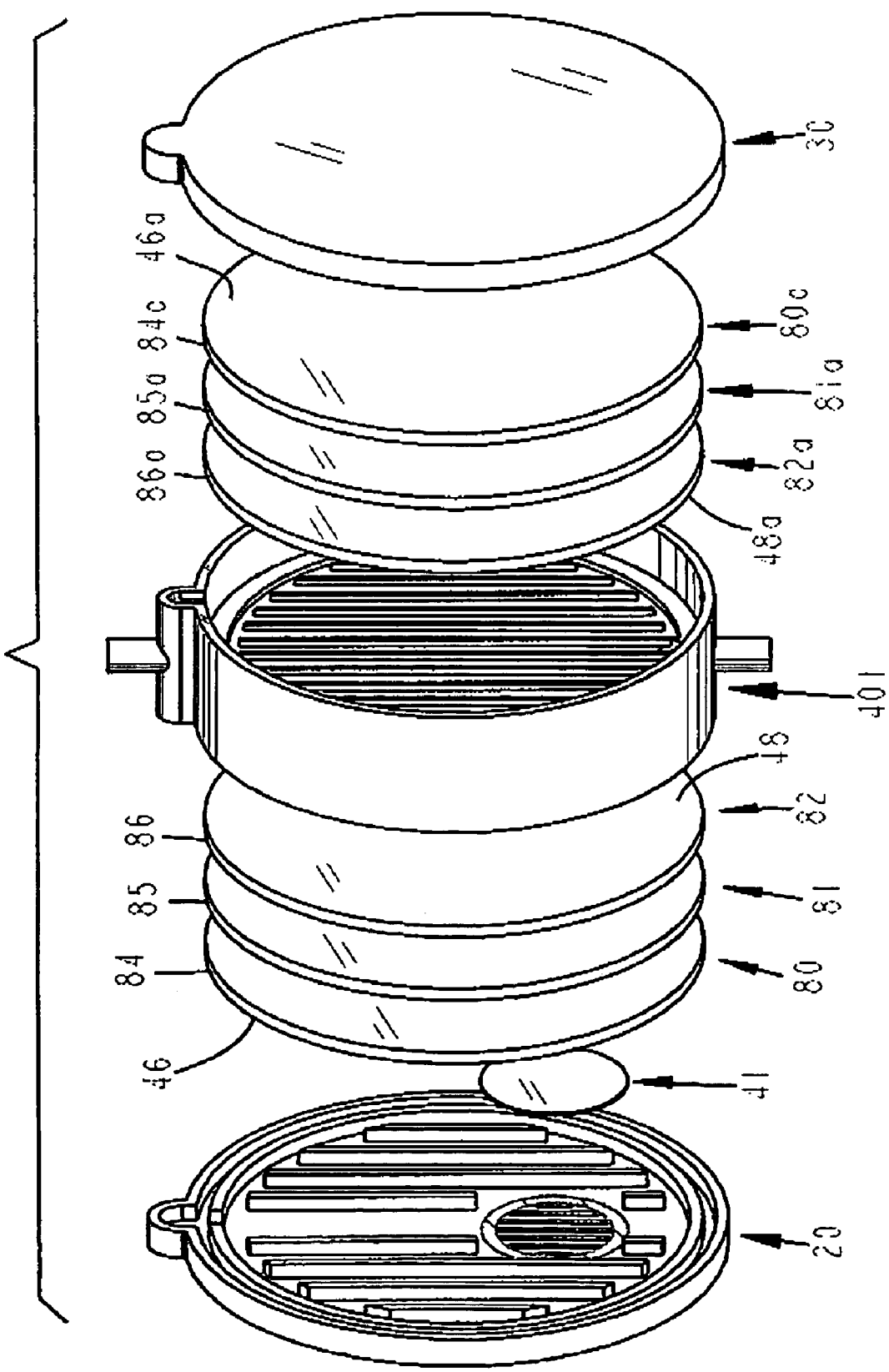
FIG. 30 is an exploded isometric view of the of the components that comprise the seventh embodiment of the filtration apparatus, constructed in accordance with the principles of the present invention, usable for the gravity filtration of blood and blood products.

A seventh embodiment of the filtration device constructed in accordance with the principles of the present invention, is shown in FIG. 28a, FIG. 28b, FIG. 29, FIG. 30, and FIG. 31. FIG. 30 shows an exploded view of the components that comprise filter device 440. Filter device 440 includes the following major components: front cover 20, body 401, back cover 30, filter elements 80, 81, 82, 80a, 81a, and 82a, and hydrophobic vent filter element 41. The only difference between filter device 40 of the first embodiment, shown in FIG. 6, and filter device 440 of the seventh embodiment, shown in FIG. 30, is that body 1 of the first embodiment is replaced with body 401 in the seventh embodiment.

Referring to FIG. 1A, FIG. 1B, FIG. 2, FIG. 28a, FIG. 28b, and FIG. 29, body 401 is identical to body 1 with the following exceptions. Side vertical channels 4, circular channel 3, and center vertical channel 5 of front flat surface 2 of partition wall 300 of body 1 are eliminated from body 401. Referring to FIG. 28a and FIG. 29, the front part of body 401 replaces these components with well 469, defined by flat surface 489 of partition wall 300, and side wall 488 of partition wall 300. Vertical filter support ribs 498 protrude from flat surface 489 of partition wall 300. A gap must exist between the top of vertical filter support ribs 498 and side wall 488. The gap should small enough to provide the proper support for filter elements 80, 81, and 82, but large enough to allow liquid or gas to flow through the gap to the top of vertical channel 487. The top face of filter support ribs 498 should lie in the same plane as flat surface 2 of partition wall 300. Vertical filter support ribs 498 could be replaced with a pattern of round pins, or with a pattern or rectangular pins, or with any other filter support means that will allow air to bubble to the top of well 469. Body 401 contains two vertical filter support ribs 499 that are attached to side wall 488 at the bottom of side wall 488. A gap must exist between the top of vertical support ribs 499 and side wall 488. Vertical channel 487 is bounded by the side walls of vertical filter support ribs 499 adjacent to channel 487, and by flat surface 489. The bottom of vertical channel 487 is in fluid flow communication with outlet port 10 via link port 11 and front outlet port 6. The top of vertical channel 487 is open. Referring to FIG. 28b, the back face of partition wall 300 of body 401 is a mirror image of the front face of partition wall 300 of body 401 just described.

The components that comprise filter device 440 are assembled in the same manner as those of filter device 40 as described above for the first embodiment.

Figure 31:
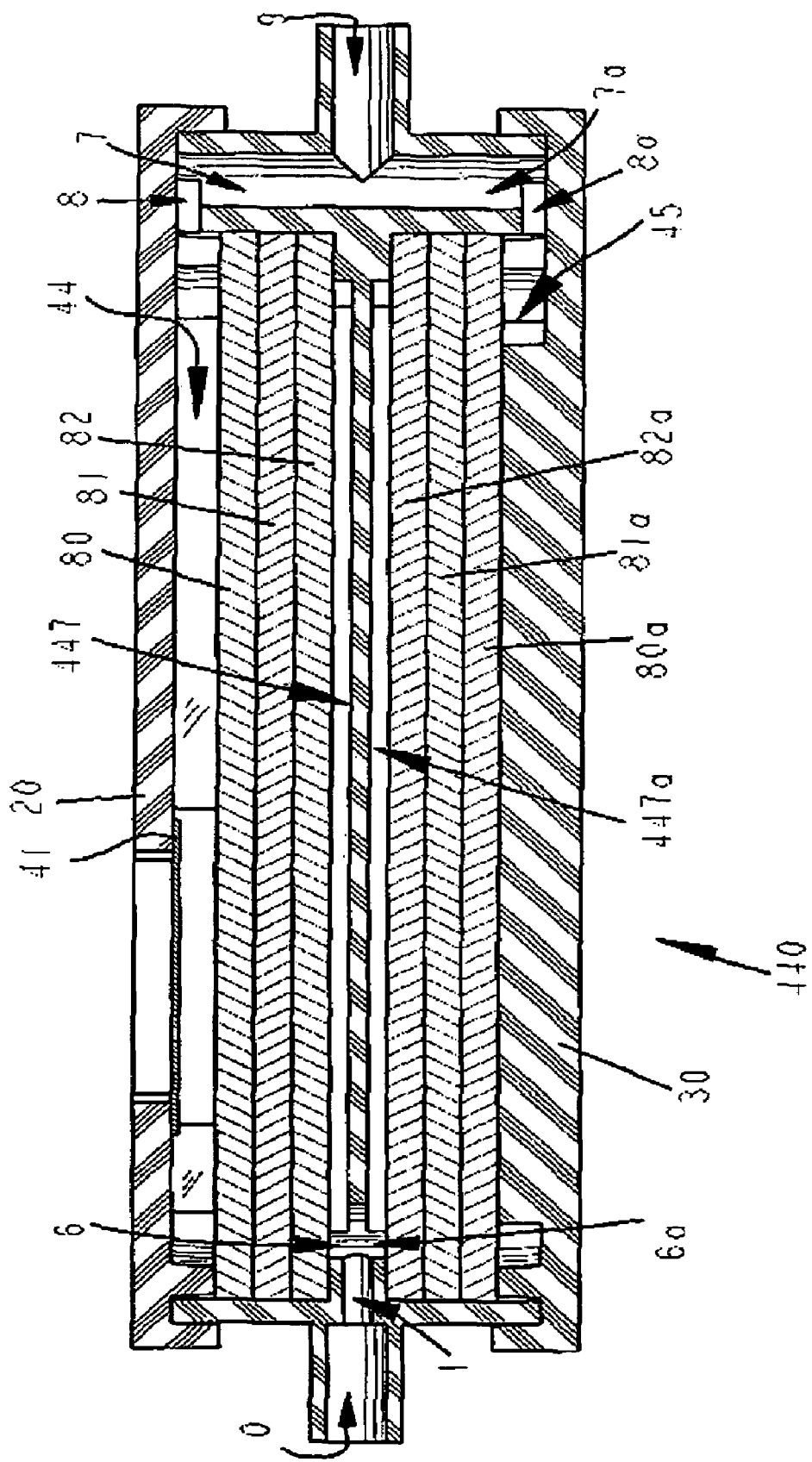
FIG. 31 is a cross-sectional view of the filtration apparatus depicted in FIG. 30.

Referring to FIG. 4B, FIG. 30, and FIG. 31, the assembled filter device 440 contains first chamber 44 of first filter well 13 bounded by flat surface 23 of front cover 20, inner surface 77 of round rib 25 of front cover 20, and the upstream surface 46 of the first filter element 80 in first filter well 13 of body 401. Referring to FIG. 5B, FIG. 30, and FIG. 31, the assembled filter device 440 also contains first chamber 45 of second filter well 13a bounded by flat surface 33 of back cover 30, inner surface 71 of round rib 35 of back cover 30, and the upstream surface 46a of the first filter element 80a in second filter well 13a of body 401. Referring to FIG. 3A and FIG. 31, in the assembled filter device 440, front inlet channel 8 becomes a closed channel bounded by side walls 15 and wall 16 of body 401, and by flat surface 23 of front cover 20. Referring to FIG. 31, front inlet channel 8 places first chamber 44 in fluid flow communication, and in air flow communication with front cross port 7. Referring to FIG. 3B and FIG. 31, in the assembled filter device 440, back inlet channel 8a becomes a closed channel bounded by side walls 15a and wall 16a of body 401, and by flat surface 33 of back cover 30. Referring to FIG. 31, back inlet channel 8a places first chamber 45 in fluid flow communication, and in air flow communication with back cross port 7a.

Referring to FIG. 28a, FIG. 29, FIG. 30 and FIG. 31, the assembled filter device 440 contains second chamber 447 of first filter well 13 bounded by the downstream surface 48 of the last filter element 82 in first filter well 13 of body 401, and by well 469. Second chamber 447 of first filter well 13 contains vertical channel 487, vertical filter support ribs 499, vertical filter support ribs 498, and front outlet port 6. As shown in FIG. 28a and FIG. 29, the portion of well 469 outside of vertical channel 487 is an open well with a pattern of vertical filter support ribs 498 protruding from flat surface 489. The space between vertical filter support ribs 498 should be small enough to provide the proper support for filter elements 80, 81, and 82, but large enough to allow gas, or gas bubbles in liquid to freely flow vertically through second chamber 447, between vertical filter support ribs 498. Furthermore, the height of vertical filter support ribs 498 and 499 should be high enough to allow gas, or gas bubbles in liquid to freely flow vertically through second chamber 447, between vertical filter support ribs 498. Referring to FIG. 28b, FIG. 30 and FIG. 31, the assembled filter device 440 contains second chamber 447a of second filter well 13a bounded by the downstream surface 48a of the last filter element 82a in second filter well 13a of body 401, and by well 469a. Second chamber 447a of second filter well 13a contains vertical channel 487a, vertical filter support ribs 499a, vertical filter support ribs 498a, and back outlet port 6a. As shown in FIG. 28b the portion of well 469a outside of vertical channel 487a is an open well with a pattern of vertical filter support ribs 498a protruding from flat surface 489a. The space between vertical filter support ribs 498a should be small enough to provide the proper support for filter elements 80, 81, and 82, but large enough to allow gas, or gas bubbles in liquid to freely flow vertically through second chamber 447a, between vertical filter support ribs 498a. Furthermore, the height of vertical filter support ribs 498 and 499 should be high enough to allow gas, or gas bubbles in liquid to freely flow vertically through second chamber 447, between vertical filter support ribs 498.

Filter device 440 could replace filter device 40 of assembly 60 shown in FIG. 9. Referring to FIG. 28A, FIG. 4B, FIG. 5B, FIG. 9, and FIG. 31 the filtration with filter device 440 replacing filter device 40 in FIG. 9 is performed as follows. The user opens inlet tube clamp 74. Gravity now forces blood to flow from feed blood bag 54, through inlet tubing 52, through inlet port 9 of body 401. After passing through inlet port 9, a portion of the blood passes through front cross port 7, while the remainder of the blood passes through back cross port 7a. The portion of the blood that passes through front cross port 7, then passes through front inlet channel 8, through gap 26 of front cover 20, into first chamber 44 of filter device 440. The portion of the blood that passes through back cross port 7a, then passes through back inlet channel 8a, through gap 36 of back cover 30, into first chamber 45 of filter device 440. A portion of the air that was in inlet tubing 52 and inlet port 9 before blood flow started will be pushed ahead of the blood, through front cross port 7, through front inlet channel 8, through gap 26 of front cover 20, into first chamber 44 of filter device 440. The remainder of the air that was in inlet tubing 52 and inlet port 9 before blood flow started will be pushed ahead of the blood, through back cross port 7a, through back inlet channel 8a, through gap 36 of back cover 30, into first chamber 45 of filter device 440. Because the usable surface area of hydrophobic filter 41 is much smaller than the usable surface area of filter elements 80, 81, and 82; and because the pressure drop across sterilizing grade hydrophobic filter 41 is much greater per unit volume of air flow per unit surface area of filter material than the combined pressure drop across filter elements 80, 81, and 82 per unit volume of air flow per unit surface area of filter material, only a very small portion of the air that was in inlet tubing 52, inlet port 9, front cross port 7, and front inlet channel 8 before blood flow started, will pass through hydrophobic filter 41, and then through slots 21 of front cover 20 to atmosphere. Therefore, most of the air that is forced into first chamber 44 by blood flow from the blood bag, and most of the air that was initially in first chamber 44 will be forced by the positive pressure (due to the blood flow) in first chamber 44, through filter elements 80, 81, and 82, into second chamber 447, through vertical channel 487, through front outlet port 6, through link port 11, through outlet port 10, through outlet tubing 53, into receiving blood bag 55; and all of the air that is forced into first chamber 45 by blood flow from the blood bag, and all of the air that was initially in first chamber 45 will be forced by the positive pressure (due to the blood flow) in first chamber 45, through filter elements 80a, 81a, and 82a, into second chamber 447a, through vertical channel 487a, through back outlet port 6a, through link port 11, through outlet port 10, through outlet tubing 53, into receiving blood bag 55.

As first chamber 44 of filter device 440 fills from the bottom up most of the air in first chamber 44 will be forced (by the positive pressure in first chamber 44) through filter elements 80, 81, and 82, for the same reasons described in the previous paragraph. This initial air will flow into second chamber 447 of first filter well 13 of filter device 440. Second chamber 447 is a closed chamber bounded by flat surface 489 and side wall 488, both of partition wall 300 of body 401, and by downstream surface 48 of filter element 82. Second chamber 447 contains closed vertical channel 487, bound by flat surface 489 of partition wall 300 of body 401, the side walls of vertical filter support ribs 499 of body 401 adjacent to vertical channel 487, and by downstream surface 48 of filter element 82. The bottom of vertical channel 487 is in fluid flow relation to outlet port 10 via front outlet port 6 and link port 11. The top end of vertical channel 487 is open to the top portion of second chamber 447. The initial air that enters second chamber 447 from filter elements 80, 81, and 82 plus all of the initial air that was in second chamber 447 will be forced from second chamber 447, through vertical channel 487, through front outlet port 6, through link port 11 through outlet port 10, through outlet tubing 53, into receiving blood bag 55. Because the volume of first chamber 44 is small, and the flow rate of blood entering first chamber 44 is much greater than the initial flow rate of blood through filter elements 80, 81, and 82, first chamber 44 will fill in a very small fraction of the time that it takes to wet filter elements 80, 81, and 82. The pressure head at the bottom of first chamber 44 will be larger than the pressure head at the top of first chamber 44, because of the height difference between the top and bottom of first chamber 44. Therefore liquid will start to come through filter element 82 into second chamber 447 from the bottom up. As second chamber 447 fills from the bottom up with blood the remaining air in second chamber 447 will be forced from second chamber 447, through vertical channel 487, through front outlet port 6, through link port 11, through outlet port 10, through outlet tubing 53, into receiving blood bag 55. Because the total volume of second chamber 447 is small (to minimize holdup) second chamber 447 may fill with blood (from the bottom up) before the upper part of filter element 82 has wet with blood. Once second chamber 447 is filled with blood, the blood from the top of second chamber 447 will flow through vertical channel 487, through front outlet port 6, through link port 11 through outlet port 10, through outlet tubing 53, into receiving blood bag 55. Once a sufficient quantity of blood flows through outlet tubing 53 the pressure head at the top of vertical channel 487 will become negative. (The negative pressure head at the top of vertical channel 487 will reach its maximum negative value when the blood in outlet tubing reaches receiving blood bag 55). Any additional air that is forced through the filter elements into second chamber 447 by blood flowing through and wetting the top portion of the filter elements will bubble to the top of second chamber 447 (because of the buoyancy of air in the blood) and be sucked out of second chamber 447, through vertical channel 487, through front outlet port 6, through link port 11 through outlet port 10, through outlet tubing 53, into receiving blood bag 55, by the negative pressure at the top of vertical channel 487 (as long as blood flow continues). This assures that filter elements 80, 81, and 82 will completely wet, and that all of the air that was in first chamber 44, filter elements 80, 81, and 82, second chamber 447, front outlet port 6, link port 11, outlet port 10, and the interior of outlet tubing 53 will be forced into receiving blood bag 55.

As first chamber 45 of filter device 440 fills from the bottom up all of the air in first chamber 45 will be forced (by the positive pressure in first chamber 45) through filter elements 80a, 81a, and 82a, for the same reasons described in the previous paragraph. This initial air will flow into second chamber 447a of second filter well 13a of filter device 440. Second chamber 447a is a closed chamber bounded by flat surface 489a and side wall 488a, both of partition wall 300 of body 401, and by downstream surface 48a of filter element 82a. Second chamber 447a contains closed vertical channel 487a, bound by flat surface 489a of partition wall 300 of body 401, the side walls of vertical filter support ribs 499a of body 401 adjacent to vertical channel 487a, and by downstream surface 48a of filter element 82a. The bottom of vertical channel 487a is in fluid flow relation to outlet port 10 via back outlet port 6a and link port 11. The top end of vertical channel 487a is open to the top portion of second chamber 447a. The initial air that enters second chamber 447a from filter elements 80a, 81a, and 82a plus all of the initial air that was in second chamber 447a will be forced from second chamber 447a, through vertical channel 487a, through back outlet port 6a, through link port 11 through outlet port 10, through outlet tubing 53, into receiving blood bag 55. Because the volume of first chamber 45 is small, and the flow rate of blood entering first chamber 45 is much greater than the initial flow rate of blood through filter elements 80a, 81a, and 82a, first chamber 45 will fill in a very small fraction of the time that it takes to wet filter elements 80a, 81a, and 82a. The pressure head at the bottom of first chamber 45 will be larger than the pressure head at the top of first chamber 45, because of the height difference between the top and bottom of first chamber 45. Therefore liquid will start to come through filter element 82a into second chamber 447a from the bottom up. As second chamber 447a fills from the bottom up with blood the remaining air in second chamber 447a will be forced from second chamber 447a, through vertical channel 487a, through back outlet port 6a, through link port 11 through outlet port 10, through outlet tubing 53, into receiving blood bag 55. Because the total volume of second chamber 447a is small (to minimize holdup) second chamber 447a may fill with blood (from the bottom up) before the upper part of filter element 82a has wet with blood. Once second chamber 447a is filled with blood, the blood from the top of second chamber 447a will flow through vertical channel 487a, through back outlet port 6a, through link port 11 through outlet port 10, through outlet tubing 53, into receiving blood bag 55. Once a sufficient quantity of blood flows through outlet tubing 53 the pressure head at the top of vertical channel 487a will become negative. (The negative pressure at the top of vertical channel 487a will reach its maximum negative value when the blood in outlet tubing reaches receiving blood bag 55). Any additional air that is forced through the filter elements into second chamber 447a by blood flowing through and wetting the top portion of the filter elements will bubble to the top of second chamber 447a (because of the buoyancy of air in blood) and be sucked out of second chamber 447a, through vertical channel 487a, through back outlet port 6a, through link port 11 through outlet port 10, through outlet tubing 53, into receiving blood bag 55, by the negative pressure at the top of vertical channel 487a (as long as blood flow continues). This assures that filter elements 80a, 81a, and 82a will completely wet, and that all of the air that was in first chamber 45, filter elements 80a, 81a, and 82a, second chamber 447a, back outlet port 6a, link port 11, outlet port 10, and the interior of outlet tubing 53 will be forced into receiving blood bag 55.

Figure 32:
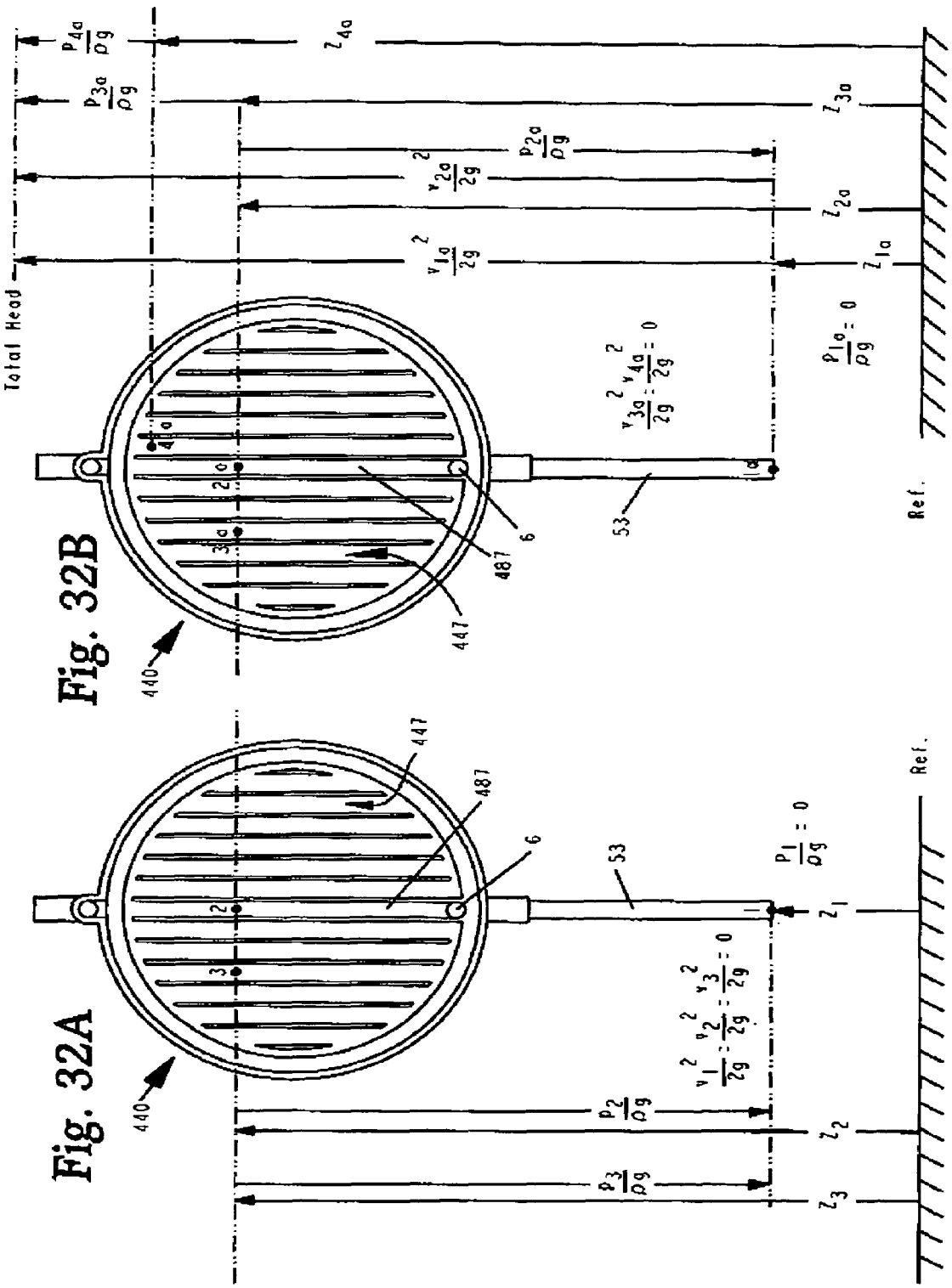
FIG. 32A is a schematic representation of the pressures in the downstream chamber of the filtration device depicted in FIG. 30, after the filtration device has been primed, for static conditions.
FIG. 32B is a schematic representation of the pressures in the downstream chamber of the filtration device depicted in FIG. 30, after the filtration device has been primed, for dynamic conditions.

FIG. 32A shows a schematic representation of second chamber 447 after the initial air that was in first chamber 44 and in second chamber 447 has been forced form chamber 447, through vertical channel 487, through front outlet port 6, through link port 11, through outlet port 10, through outlet tubing 53, into receiving blood bag 55; and after blood has filled second chamber 447, and at least a portion of the top of vertical channel 487, as explained above. FIG. 32A shows that the blood level has reached point 1 in outlet tubing 53, and that vertical channel 487 and outlet tubing 53 from point 1 to the top of vertical channel 487 are filled with blood. Because the receiving blood bag is surrounded by atmospheric pressure, point 1 is considered to be at atmospheric pressure. In FIG. 32A it is assumed that blood flow from the feed blood bag has been shut off, so that blood flow through filter elements 80, 81, and 82 has also stopped. Applying Bernoulli's equation to FIG. 32A, we have:

$$(v_1^2/2\ g)+(p_1/\rho g)+(z_1)=(v_2^2/2\ g)+(p_2/\rho g)+(z_2)=(v_3^2/2\ g)+(p_3/\rho g)+(z_3)$$

Where:

$(v^2/2\ g)$ is the velocity head $(p/\rho g)$ is the pressure head $z$ is the elevation head Because the blood bag is surrounded by atmospheric pressure:

$$(p_1/\rho g)=0$$

Because it is assumed that flow has stopped:

$$v_1=v_2=v_3=0$$

Therefore:

$$z_1=(z_2+(p_2/\rho g))=(z_3+(p_3/\rho g))$$

Therefore the pressure at any point on any horizontal line in second chamber 447 is equal to the pressure at any other point on the same horizontal line, as shown by points 2 and 3 in FIG. 32A. Because there is no pressure differential between point 2 inside of vertical channel 487 and point 3 outside of vertical channel 487, or between any other two points on any horizontal line in second chamber 447, any air that bubbles to the top of second chamber 447 because of the buoyancy of the air will not be sucked out of second chamber 447 into vertical channel 487 if there is no blood flow through the filter elements.

FIG. 32B shows a schematic representation of second chamber 447 after the initial air that was in first chamber 44 and in second chamber 447 has been forced form chamber 447, through vertical channel 487, through front outlet port 6, through link port 11, through outlet port 10, through outlet tubing 53, into receiving blood bag 55; and after blood has filled second chamber 447, and at least a portion of the top of vertical channel 487, as explained above. FIG. 32A shows that the blood level has reached point 1a in outlet tubing 53, and that vertical channel 487 and outlet tubing 53 from point 1a to the top of vertical channel 487 are filled with blood. Because the receiving blood bag is surrounded by atmospheric pressure, point 1a is considered to be at atmospheric pressure. In FIG. 32B it is assumed that blood is flowing from the feed blood bag, hence blood will also be flowing through filter elements 80, 81, and 82. Applying Bernoulli's equation to FIG. 32B, we have:

$$(v_{1a}^2/2\ g)+(p_{1a}/\rho g)+(z_{1a})=(v_{2a}^2/2\ g)+(p_{2a}/\rho g)+(z_{2a})=$$

$$(v_{3a}^2/2\ g)+(p_{3a}/\rho g)+(z_{3a})=(v_{4a}^2/2\ g)+(p_{4a}/\rho g)+(z_{4a})=$$
Total Head Because the blood bag is surrounded by atmospheric pressure:

$$(p_{1a}/\rho g)=0$$

Because all of the blood flow through filter elements 80, 81, and 82, must flow through vertical channel 487 and outlet tubing 53, the flow rate through vertical channel 487 and outlet tubing will be at least ten times the flow through any channel between adjacent pairs of vertical filter support ribs outside of vertical channel 487. Since the velocity head is proportional to the square of velocity it is assumed that the velocity head outside of vertical channel 487 equals zero, hence:

$$(v_{3a}^2/2\ g)=(v_{4a}^2/2\ g)=0$$

Therefore applying Bernoulli's equation to FIG. 32B, it can be seen that when blood flows through the filter elements because of a positive pressure on the upstream side of the filter elements, the head pressure inside of vertical channel 487 will be negative, with the maximum negative value at the top of vertical channel 487. It can also be seen that in a small region immediately outside of vertical channel 487 the head pressure will be negative, but less negative than the head pressure at the top of vertical channel 487. For all other points outside of vertical channel 487, inside of second chamber 447 the head pressure will be positive. Hence any air that is forced from the filter elements into second chamber 447 by blood flow through the filter will bubble to the top of second chamber 447 because of the buoyancy of the air in blood, and will then be sucked into vertical channel 487 because of the negative pressure head inside of vertical channel 487, and the positive pressure head outside of vertical channel 487. Both the forcing of air out of the filter elements into second chamber 447, and the sucking of the air out of the top of second chamber 447 into vertical channel 487, are dependent on blood flow through the filter elements, which is in turn dependent upon a positive pressure in first chamber 44. The positive pressure in first chamber 44 can be created by gravity flow from a reservoir positioned above chamber 44, or by any other source of positive pressure such as a pump.

Bernoulli's equation can be applied in the same way as above, for first chamber 45, filter elements 80a, 81a, 82a, and second chamber 447a.

In FIG. 32B it is assumed that the cross-sectional area of the vertical channel and that of the outlet tubing are equal. Therefore, the velocity head at point 2 equals the velocity head at point 1. However, in FIG. 2, FIG. 11, and in FIG. 29, the cross-sectional area of the link port is shown smaller than that of the vertical channels of either the first filter well or the second filter well. Therefore, by applying Bernoulli's equation it can be seen that the maximum negative pressure will occur in the link port, not at the top of the vertical channel, because the velocity head will have its maximum value in the link port, and the total head at all points on the downstream side of the filter elements must be equal as described above. With the cross-sectional area of the link port less than that of the vertical channel, air that bubbles to the top of the second chamber will be sucked into the vertical channel as described above. Hence it can be seen that the link port, or the front outlet port, or the back outlet port, or the outlet port may have a cross-sectional area less than that of the vertical channel.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in front outlet port 6, and the pressure head in back outlet port 6a will be negative, as will be the pressure head in second chamber 447, and second chamber 447a, all of body 401. Once blood flow has stopped the pressure drop across filter elements 80, 81, and 82, will fall to zero. The pressure drop across filter elements 80a, 81a, and 82a, will also fall to zero. Hence the pressure in first chamber 44 and first chamber 45 will become negative. Once the pressure in first chamber 44 falls below atmospheric pressure air will begin to flow from atmosphere through slots 21, through sterilizing grade hydrophobic filter 41, into first chamber 44. The sterile air that enters first chamber 44 will bubble up to the top of first chamber 44, thus causing first chamber 44 to drain from the top down. Because of the negative pressure in first chamber 45, some of the air that bubbles to the top of first chamber 44 will pass through gap 26, through front inlet channel 8, through front cross port 7, through back cross port 7a, through gap 36, through back inlet channel 8a, into first chamber 45, causing first chamber 45 to drain from the top down, and causing the blood in front inlet channel 8 to drain into first chamber 44, and causing the blood in back inlet channel 8a to drain into first chamber 45, and causing the blood in front cross port 7 and back cross port 7a to drain into both first chamber 44 and first chamber 45. Because the air entering first chamber 44 bubbles to the top of first chamber 44, thus draining first chamber 44 from the top down, vent filter element 41 can be located anywhere on flat surface 23 of front cover 20. Filter elements 80, 81, 82, 80a, 81a, and 82a will be plugged sufficiently at this point, therefore very little if any blood will be sucked from these filter elements by the negative pressure in second chamber 447, and by the negative pressure in second chamber 447a.

Hence blood flow will stop after first chamber 44 and first chamber 45 have drained and blood will remain in filter elements 80, 81, 82, 80a, 81a, and 82a, in second chamber 447, in second chamber 447a, and in front outlet port 6, back outlet port 6a, link port 11, outlet port 10 all of body 401, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 440 can now be discarded in a safe manner. Outlet tubing 53 will have segments marked on them. The user can now seal the tubing at the segment marks. The blood that is left in outlet tubing 53 will be used for cross matching and for quality control purposes.

Although the filter support means (including vertical channel 487) of second chamber 447 and the filter support means (including vertical channel 487a) of second chamber 447a are used in conjunction with the two sided filter device of the seventh embodiment of the present invention it will be appreciated by those skilled in the art that the same filter support means could be used with a single sided filter.

Body 101, and body 201, could also be modified to incorporate second chamber 447 of body 401, and second chamber 447a of body 401. Hence any of the embodiments from the first embodiment to the sixth embodiment could function like the seventh embodiment.

Figure 33:
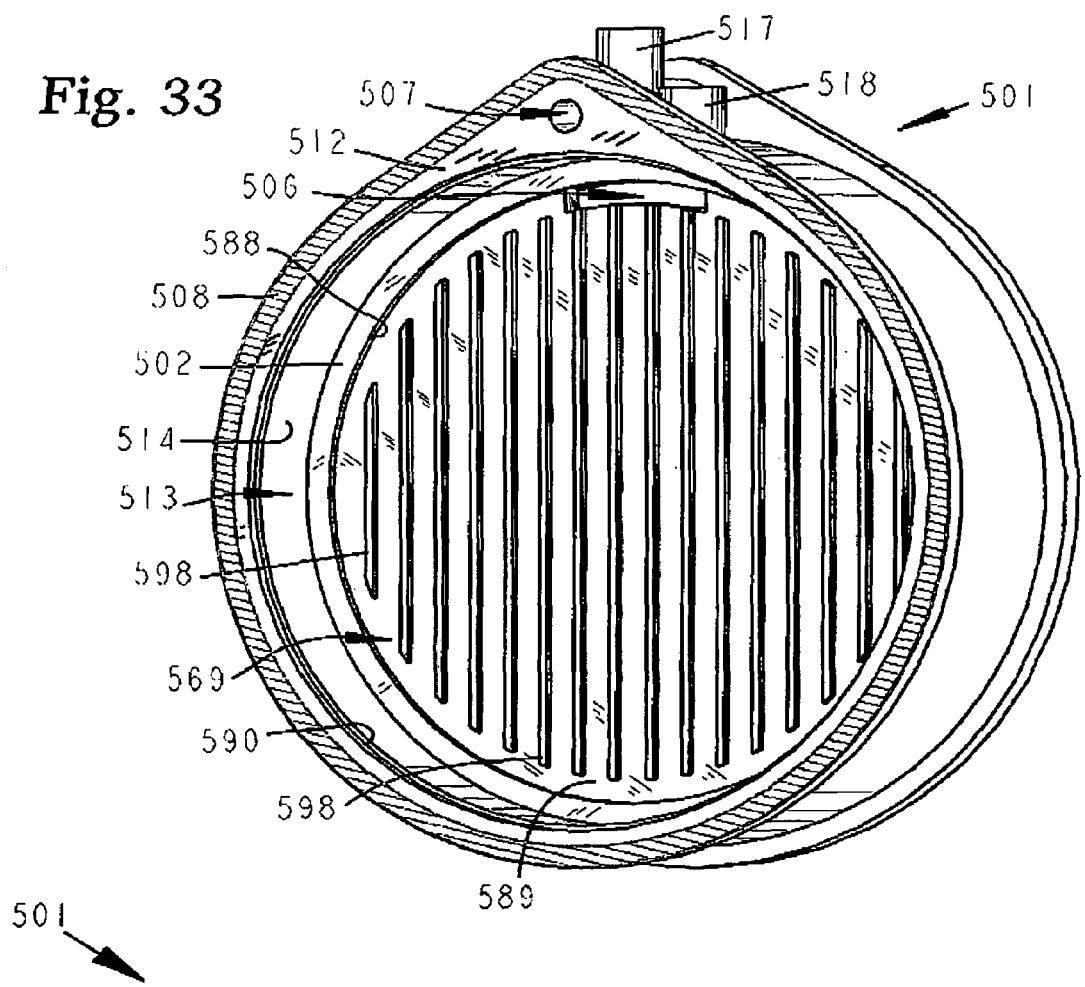
FIG. 33 is a front isometric view of the body of the filtration apparatus depicted in FIG. 39.
Figure 39:
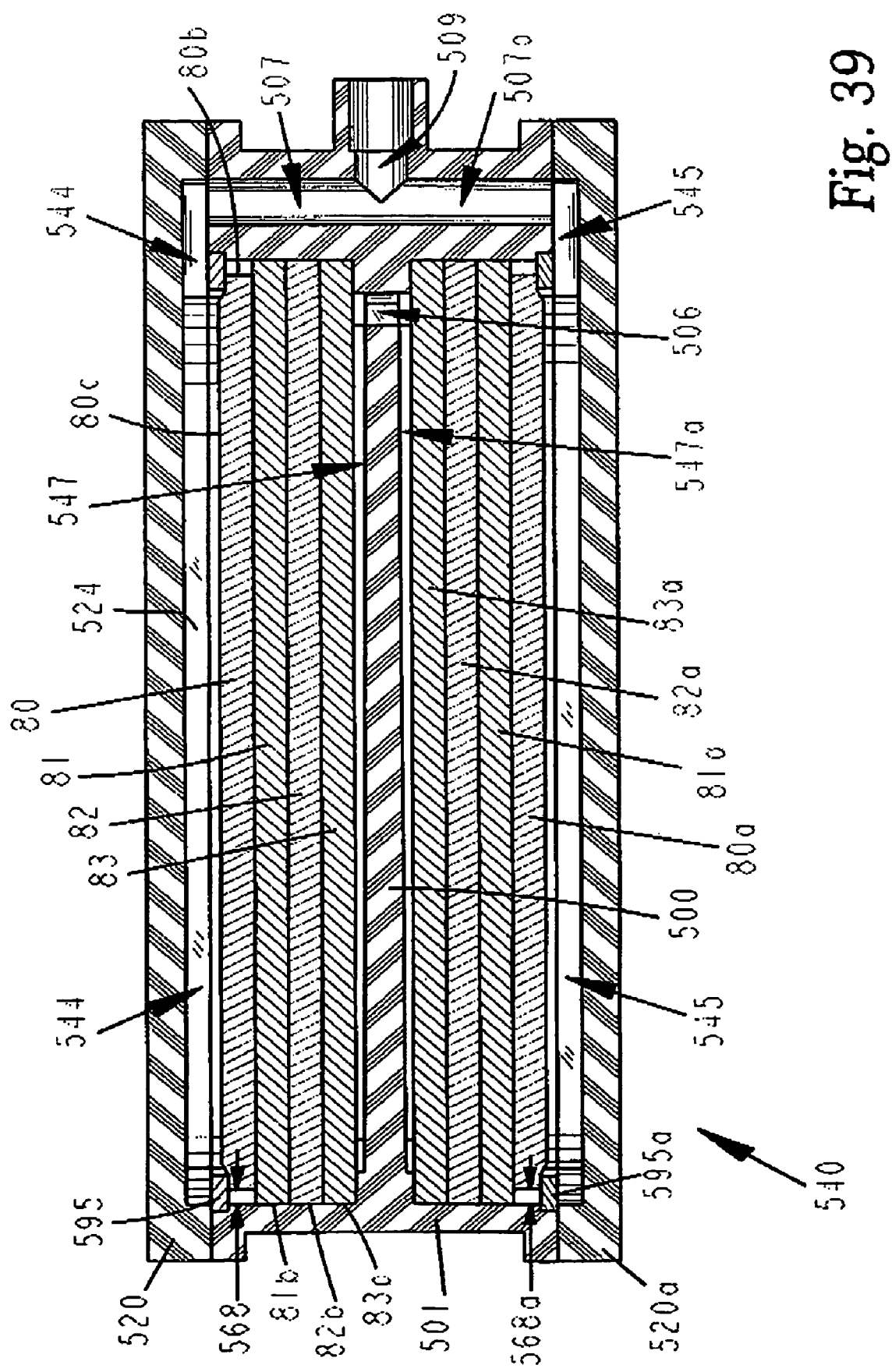
FIG. 39 is a cross-sectional view of the eighth embodiment of the filtration apparatus, constructed in accordance with the principles of the present invention, usable for the filtration of blood and blood products.

An eight embodiment of the filtration device constructed in accordance with the principles of the present invention, is shown in FIG. 33, through FIG. 39. FIG. 39 shows a cross-sectional view of filter device 540, with the plane of the cross-section intersecting the central axis of inlet port 509, and the central axis of front cross port 507 and back cross port 507a. Filter device 540 includes the following components: front cover 520, body 501, back cover 520a, filter elements 80, 81, 82, 83, 80a, 81a, 82a, and 83a.

Figure 34:
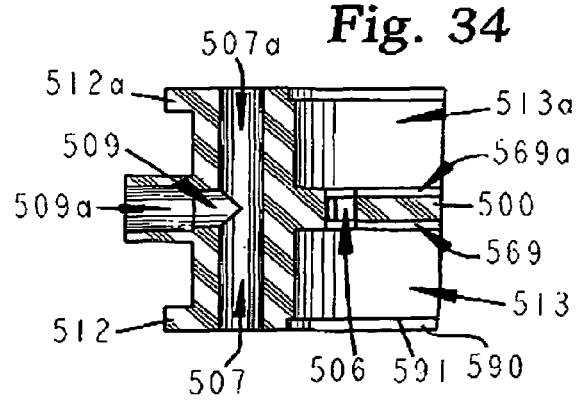
FIG. 34 is partial cross-sectional view of the body shown in FIG. 33, with the plane of the cross-section being perpendicular to the partition wall, and intersecting the center of the inlet.
Figure 35:
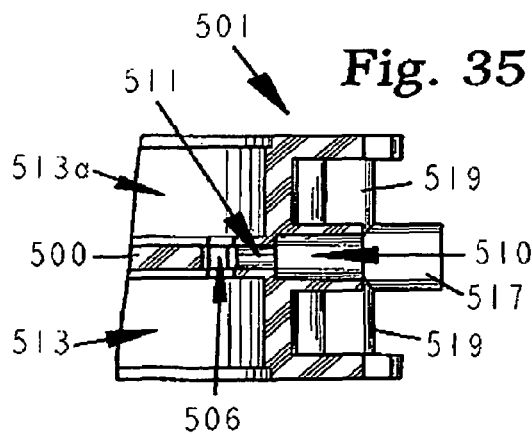
FIG. 35 is partial cross-sectional view of the body shown in FIG. 33, with the plane of the cross-section being perpendicular to the partition wall, and intersecting the center of the outlet.
Figure 36:
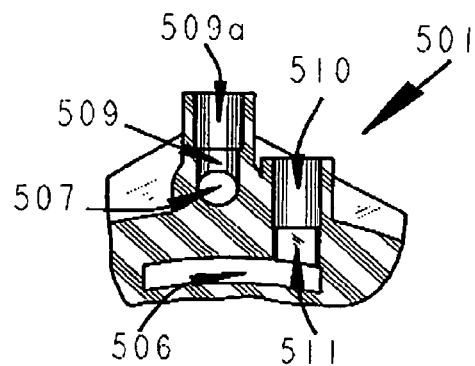
FIG. 36 is partial cross-sectional view of the body shown in FIG. 33, with the plane of the cross-section being parallel to the partition wall, and intersecting the center of the inlet and the center of the outlet.
Figure 37:
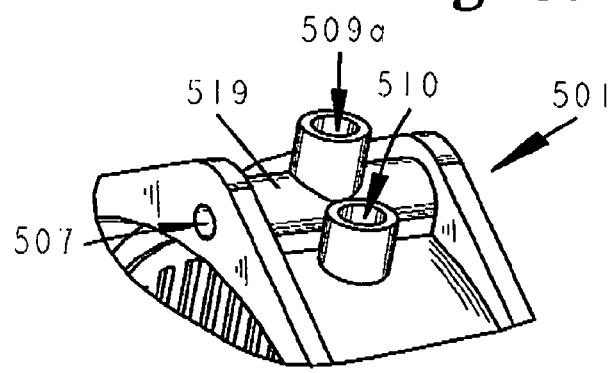
FIG. 37 is a partial isometric view of the body shown in FIG. 33 showing the top portion of the body.

Referring to FIG. 33 through FIG. 37, and FIG. 39, the front part of body 501 contains first filter well 513 bounded by a plane that goes through filter seal surface 502, and by side wall 514. The front part of body 501 also contains first downstream well 569 bounded by the front side of partition wall 500 labeled as flat surface 589, and by side wall 588. Vertical filter support ribs 598 protrude from flat surface 589. The top surface of vertical filter support ribs 598 preferably lies in the plane that goes through filter seal surface 502. Flat surface 589 may be skewed relative to filter seal surface 502 to create a tapered first downstream well 569 with the top of the well being deeper than the bottom as shown in FIG. 33 and FIG. 39. The top of first filter well 513 may contain counterbore 590. The front part of body 501 also contains front flange 512. The back part of body 501 is a mirror image of the front part of body 501 mirrored about a plane that goes through the center of partition wall 500. Body 501 also contains cross protrusion 519 and inlet tube socket protrusion 517, which in turn contain inlet tube socket 509a, inlet port 509, front cross port 507, and back cross port 507a. The outlet end of front cross port 507 terminates at the front surface of front flange 512, and the outlet end of back cross port 507a terminates at the front surface of back flange 512a as shown in FIG. 34. Front cross port 507 and first filter well 513 lie within the inner perimeter of front cover seal surface 508 shown cross-hatched in FIG. 33. Likewise, back cross port 507a and second filter well 513a lie within the inner perimeter of the back cover seal surface. Body 501 also contains outlet tube socket protrusion 518, outlet tube socket 510, outlet port 511, and through slot 506. The top of first downstream well 569 and the top of second downstream well 569a communicate with outlet port 511 via through slot 506. As shown in FIG. 36, the centerline of front cross port 507 is offset slightly to the left of the vertical center line of first filter well 513 so that outlet port 511 is placed as close to the top of first filter well 513 as possible. The centerline of front cross port 507 could however, be aligned with the vertical center line of first filter well 513. Body 501 is preferably made from an injection moldable medical grade plastic such acrylic, polycarbonate, polysulfone, polypropylene, polyethylene, but is not limited to these materials.

Figure 38:
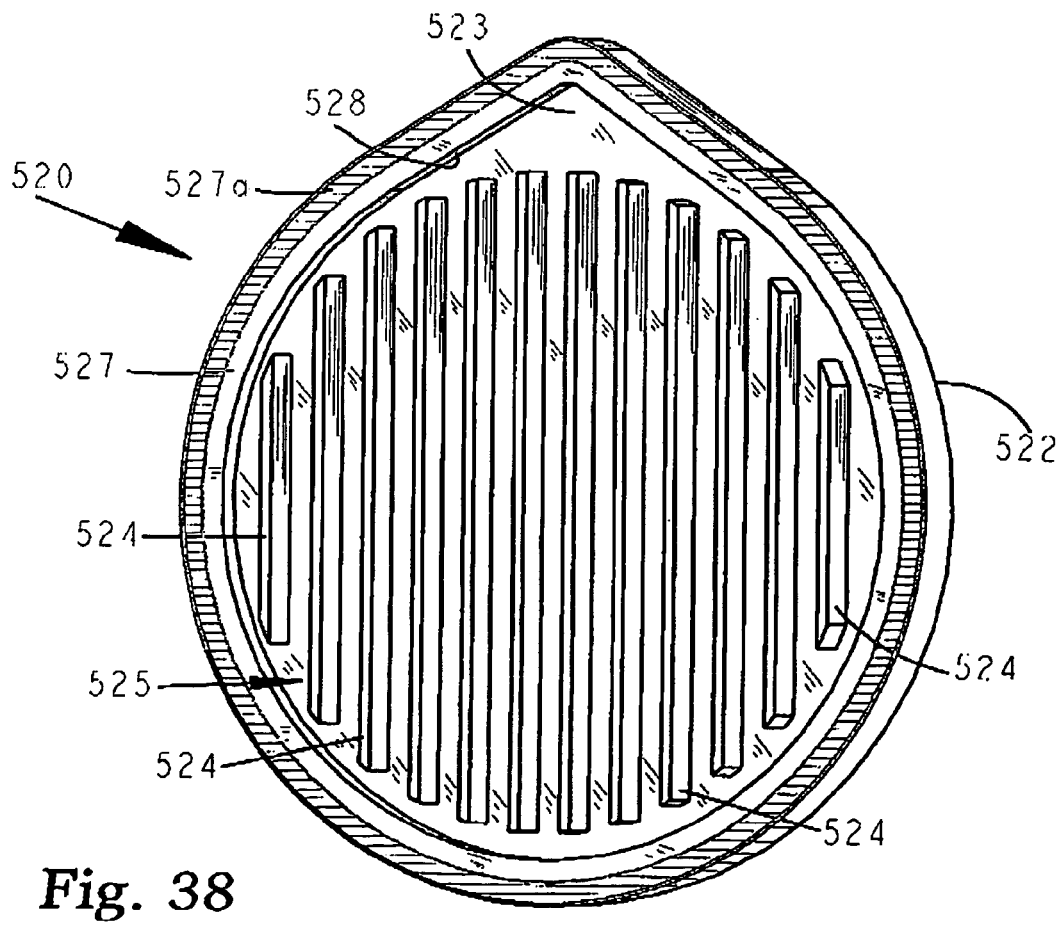
FIG. 38 is an isometric view of the front cover, showing the interior of the front cover.

Referring to FIG. 38, front cover 520 contains well 525 bounded by flat surface 523 and by side wall 528. Filter support ribs 524 protrude from flat surface 523. The outer periphery of surface 527 located at the top of well 525, and designated as seal surface 527a, and shown cross-hatched is sealed to front cover seal surface 508 of body 501 as shown in FIG. 39. Filter support ribs 524 protrude beyond surface 527 to add support to the upstream surface of the filter media in the first filter well of body 501 as shown in FIG. 39. Back cover 520a shown in FIG. 39 is a mirror image of front cover 520 mirrored about outside surface 522 of front cover 520. Front cover 520 and back cover 520a are preferably made from an injection moldable medical grade plastic such acrylic, polycarbonate, polysulfone, polypropylene, polyethylene, but is not limited to these materials.

Referring to FIG. 39, filter device 540 includes a housing that contains body 501, front cover 520, and back cover 520a. A first filtration media composed of filter elements 80, 81, 82, and 83, is inserted into the first filter well of body 501, and a second filtration media composed of elements 80a, 81a, 82a, and 83a is inserted into the second filter well of body 501.

Referring to FIG. 33 through FIG. 39, filter device 540 contains a first filter well 513 that contains a first filtration media composed of filter elements 80, 81, 82, and 83. The filtration media must contain at least one filter element, with each filter element composed of one or more layers of filter material of the same type. All filter elements may be made from the same type of filter material, or they may be made from different types of filter material. The outer edges of all of the filter elements of the first filtration media are disposed below the top of first filter well 513, with the shape of the outer edge of each filter element being the same as the shape of the side wall of the first filter well. Therefore, if first filter well is round as shown, the filter elements must also be round, or if the shape of the first filter well is square, then the shape of the filter elements must also be square. The outer edge of each filter element is designated with the reference number of the filter element plus the extension b, therefore the outer edge of filter element 80 is designated as outer edge 80b. Because the outer edge of all of the filter elements of the first filtration media lie below the top of the first filter well, and because the shape of the filter elements is the same as the shape of the side wall of the first filter well, the filter elements may be sealed to the first filter well with a compression fit between the outer edge of the filter elements and the side wall of the first filter well. Filter elements 81, 82, and 83 shown in FIG. 39 are sealed to filter device 540 with a compression fit between the outer edge of each respective filter element and the side wall of the first filter well. To form a compression fit between the outer edge of a filter element and the filter well into which it is inserted the outside diameter of the filter element must be greater than the inside diameter of the filter well. Referring to FIG. 39, filter element 80 has an outside diameter smaller than the inside diameter of the side wall of the first filter well.

Therefore filter element 80 can not be sealed to the first filter well with a compression fit between the outer edge of filter element 80 and the side wall of the first filter well. Referring to FIG. 33 and FIG. 39, first filter compression ring 595 is press fitted into counterbore 590 of body 501, thereby compressing the outer periphery of filter element 80, thereby sealing filter element 80 to filter device 540. Alternately first filter compression ring 595 could be eliminated, and all of the filter elements in first filter well could be sealed to filter device 540 with a compression fit between the outer edge of each respective filter element and the side wall of the first filter well. A second alternative would be to keep first filter compression ring and also have a compression fit between the outer edge of all of the filter elements in the first filter well and the side wall of the first filter well. A third alternative would be to make the outside diameter of all of the filter elements in the first filter well smaller than the inside diameter of the side wall of the first filter well, and compress the outer periphery of all of the filter elements in the first filter well between the first filter compression ring and filter seal surface 502 of the first filter well. This method of sealing would not be as effective as the other methods just mentioned. Other alternatives would be to bond one or more of the filter elements in the first filter well to the first filter well with a heat bond, an ultrasonic bond, a glue bond, a solvent bond or any other type of leak tight bond. Any combination of the above mentioned sealing methods could also be used. The second filter well of filter device 540 contains a second filtration media that should contain the same type of filter elements that are contained in the first filter well, sealed to the second filter well in the same manner that the first filtration media is sealed to the first filter well.

Front cover 520 and back cover 520a are bonded to body 501 as described above using a heat bond, an ultrasonic bond, a glue bond, a solvent bond, a radio frequency bond, or any other type of leak tight bond.

Referring to FIG. 36 and FIG. 39 a first fluid flow path is defined between inlet port 509 of filter device 540 and outlet port 511 of filter device 540 with the first filtration media interposed between inlet port 509 and outlet port 511, and across the first fluid flow path. The first fluid flow path flows from inlet port 509, through front cross port 507, into first chamber 544, through the first filtration media, into second chamber 547, into through slot 506, into outlet port 511. A second fluid flow path is defined between inlet port 509 of filter device 540 and outlet port 511 of filter device 540 with the second filtration media interposed between inlet port 509 and outlet port 511, and across the second fluid flow path. The second fluid flow path flows from inlet port 509, through back cross port 507a, into first chamber 545, through the second filtration media, into second chamber 547a, into through slot 506, into outlet 511. The first filtration media contains filter elements 80, 81, 82, and 83. The second filtration media contains filter elements 80a, 81a, 82a, and 83a.

Filter device 540 could replace filter device 40 of assembly 60 shown in FIG. 9. Referring to FIG. 33 through FIG. 39 the filtration with filter device 540 replacing filter device 40 in FIG. 9 is performed as follows. The user opens inlet tube clamp 74. Gravity now forces blood to flow from feed blood bag 54, through inlet tubing 52, through inlet port 509 of body 501. After passing through inlet port 509, a portion of the blood passes through front cross port 507, while the remainder of the blood passes through back cross port 507a. Because the outlet end of front cross port 507 is located within first chamber 544, the portion of the blood that passes through front cross port 507, then passes into first chamber 544 of filter device 540; and because the outlet end of back cross port 507a is located within first chamber 545, the portion of the blood that passes through back cross port 507a, then passes into first chamber 545 of filter device 540. A portion of the air that was in inlet tubing 52 and inlet port 509 before blood flow started will be pushed ahead of the blood, through front cross port 507 into first chamber 544 of filter device 540. The remainder of the air that was in inlet tubing 52 and inlet port 509 before blood flow started will be pushed ahead of the blood, through back cross port 507a into first chamber 545 of filter device 540. All of the air that is forced into first chamber 544 by blood flow from the blood bag, and all of the air that was initially in first chamber 544 will be forced by the positive pressure (due to the blood flow) in first chamber 544, through filter elements 80, 81, 82, and 83, into second chamber 547, into through slot 506, through outlet port 511, through outlet tubing 53, into receiving blood bag 55; and all of the air that is forced into first chamber 545 by blood flow from the blood bag, and all of the air that was initially in first chamber 545 will be forced by the positive pressure (due to the blood flow) in first chamber 545, through filter elements 80a, 81a, 82a, and 83a, into second chamber 547a, into through slot 506, through outlet port 511, through outlet tubing 53, into receiving blood bag 55.

As first chamber 544 of filter device 540 fills from the bottom up all of the air in first chamber 544 will be forced (by the positive pressure in first chamber 544) through filter elements 80, 81, 82, and 83, for the same reasons described in the previous paragraph. This initial air will flow into second chamber 547 of first filter well 513 of filter device 540. Second chamber 547 is a closed chamber bounded by flat surface 589 and side wall 588, both of partition wall 500 of body 501, and by the downstream surface of filter element 83. The top of second chamber 547 is in fluid flow communication with outlet port 511 via through slot 506 located at the top of second chamber 547. The initial air that enters second chamber 547 from filter elements 80, 81, 82, and 83, plus all of the initial air that was in second chamber 547 will be forced from second chamber 547, into through slot 506, through outlet port 511, through outlet tubing 53, into receiving blood bag 55. Outlet port 511 and outlet tube socket 510 are located near the top of filter device 540. Therefore a loop must be formed in the end of outlet tubing 53 that is bonded to the outlet tube socket so that outlet tubing 53 can change direction from upward as it comes out of the outlet tube socket to downward toward the receiving blood bag. Because the volume of first chamber 544 is small, and the flow rate of blood entering first chamber 544 is much greater than the initial flow rate of blood through filter elements 80, 81, 82, and 83, first chamber 544 will fill in a fraction of the time that it takes to wet filter elements 80, 81, 82, and 83. The pressure head at the bottom of first chamber 544 will be larger than the pressure head at the top of first chamber 544, because of the height difference between the top and bottom of first chamber 544. Therefore liquid will start to come through filter element 83 into second chamber 547 from the bottom up. As second chamber 547 fills from the bottom up with blood the remaining air in second chamber 547 will be forced from second chamber 547, into through slot 506, through outlet port 511, through outlet tubing 53, into receiving blood bag 55. Because the total volume of second chamber 547 is small (to minimize holdup) second chamber 547 may fill with blood (from the bottom up) before the upper part of filter element 83 has wet with blood. Once second chamber 547 is filled with blood, the blood will flow from of second chamber 547 into through slot 506, through outlet port 511, through outlet tubing 53, into receiving blood bag 55. Any additional air that is forced through the filter elements into second chamber 547 by blood flowing through and wetting the top portion of the filter elements will bubble to the top of second chamber 547 (because of the buoyancy of air in the blood) and be forced out of second chamber 547, into through slot 506, through outlet port 511, through outlet tubing 53, into receiving blood bag 55, by the flow of blood from second chamber 547, into through slot 506, through outlet port 511. This assures that filter elements 80, 81, 82, and 83 will completely wet, and that all of the air that was in first chamber 544, filter elements 80, 81, 82, and 83, second chamber 547, through slot 506, outlet port 511, and the interior of outlet tubing 53 will be forced into receiving blood bag 55. Because there is no siphon tube in second chamber 547, all of the air will be purged from within the filter device by the positive pressure within the filter device, and by the flow of blood through the filter device created by the positive pressure. The initial air in first chamber 545, filter elements 80a, 81a, 82a, 83a, and second chamber 547a will be also purged as just described.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in outlet port 511 will be negative, as will be the pressure head in second chamber 547, and second chamber 547a, all of body 501. Once blood flow has stopped the pressure drop across filter elements 80, 81, 82, and 83, will fall to zero. The pressure drop across filter elements 80a, 81a, 82a, and 83a, will also fall to zero. Hence the pressure in first chamber 544 and first chamber 545 will become negative. The pressure in front cross port 507, back cross port 507a, inlet port 509, and inlet tubing 52 will also be negative. If a means (not shown) is provided to allow sterile air to enter inlet tubing 52 after filtration is complete, the portion of inlet tubing 52 below the point of sterile air entry, along with inlet port 509, front cross port 507, back cross port 507a, first chamber 544, and first chamber 545 will drain until first chamber 544 and first chamber 545 are empty, and blood will remain in filter elements 80, 81, 82, 83, 80a, 81a, 82a, and 83a, second chamber 547, second chamber 547a, through slot 506, outlet port 511, and in outlet tubing 53. If a means is not provided to allow sterile air to enter inlet tubing 52 after filtration is complete, blood will remain in inlet tubing 52, inlet port 511, front cross port 507, back cross port 507a, first chamber 544, first chamber 545, filter elements 80, 81, 82, 83, 80a, 81a, 82a, and 83a, second chamber 547, second chamber 547a, through slot 506, outlet port 511, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 540 can now be discarded in a safe manner. Outlet tubing 53 will have segments marked on it. The user can now seal the outlet tubing at the segment marks. The blood that is left in outlet tubing 53 will be used for cross matching and for quality control purposes.

Although the filter support means of second chamber 547 and the filter support means of second chamber 547a are used in conjunction with the two sided filter device of the eighth embodiment of the present invention it will be appreciated by those skilled in the art that the same filter support means could be used with a single sided filter device.

Body 101, body 201, and body 401, could also be modified to incorporate second chamber 547 of body 501, and second chamber 547a of body 501. Hence any of the embodiments from the first embodiment to the seventh embodiment could function like the eighth embodiment.

Alternately filter device 540 could be used as follows. Referring to FIG. 33 through FIG. 39, inlet port 509 and outlet 511 could be transposed so that the inlet port becomes the outlet port and the outlet port becomes the inlet port. In this case when filter device 540 is used to replace filter device 40 in assembly 60 (shown in FIG. 9), the outlet end of inlet tubing 52 will be connected to outlet tube socket 510 of body 501, and the inlet end of outlet tubing 53 will be connected to inlet tube socket 509a of body 501. Referring to FIG. 33 through FIG. 39 and to FIG. 9, when filter device 540 is used with the inlet port and outlet port transposed, the filtration is performed as follows. The user opens inlet tube clamp 74. Gravity now forces blood to flow from feed blood bag 54, through inlet tubing 52, through outlet port 511, into through slot 506. A portion of the blood then passes from through slot 506 into second chamber 547, while the remainder of the blood passes from through slot 506 into second chamber 547a. A portion of the air that was in inlet tubing 52 and outlet port 511 before blood flow started will be pushed ahead of the blood, into through slot 506, into second chamber 547 of filter device 540. The remainder of the air that was in inlet tubing 52 and outlet port 511 before blood flow started will be pushed ahead of the blood, into through slot 506, and then into second chamber 547a of filter device 540. All of the air that is forced into second chamber 547 by blood flow from the blood bag, and all of the air that was initially in second chamber 547 will be forced by the positive pressure (due to the blood flow) in second chamber 547, through filter elements 83, 82, 81, and 80, into first chamber 545, into front cross port 507, through inlet port 509, through outlet tubing 53, into receiving blood bag 55; and all of the air that is forced into second chamber 547a by blood flow from the blood bag, and all of the air that was initially in second chamber 547a will be forced by the positive pressure (due to the blood flow) in second chamber 547a, through filter elements 83a, 82a, 81a, and 80a, into first chamber 545, into back cross port 507a, through inlet port 509, through outlet tubing 53, into receiving blood bag 55.

As second chamber 547 of filter device 540 fills from the bottom up all of the air in second chamber 547 will be forced (by the positive pressure in second chamber 547) through filter elements 83, 82, 81, and 80, for the same reasons described in the previous paragraph. This initial air will flow into first chamber 544 of filter device 540. First chamber 544 is a closed chamber bounded by flat surface 523 and side wall 528, both of front cover 520, and by the downstream surface of filter element 80. The top of first chamber 544 is in fluid flow communication with inlet port 509 via front cross port 507 located at the top of first chamber 544. The initial air that enters first chamber 544 from filter elements 83, 82, 81, and 80 plus all of the initial air that was in first chamber 544 will be forced from first chamber 544, into front cross port 507, through inlet port 509, through outlet tubing 53, into receiving blood bag 55. Because the volume of second chamber 547 is small, and the flow rate of blood entering second chamber 547 is greater than the initial flow rate of blood through filter elements 83, 82, 81, and 80, second chamber 547 will fill in a fraction of the time that it takes to wet filter elements 83, 82, 81, and 80. The pressure head at the bottom of second chamber 547 will be larger than the pressure head at the top of second chamber 547, because of the height difference between the top and bottom of second chamber 547. Therefore liquid will start to come through filter element 80 into first chamber 544 from the bottom up. As first chamber 544 fills from the bottom up with blood the remaining air in first chamber 544 will be forced from first chamber 544, into front cross port 507, through inlet port 509, through outlet tubing 53, into receiving blood bag 55. Because the total volume of first chamber 544 is small (to minimize holdup) first chamber 544 may fill with blood (from the bottom up) before the upper part of filter element 80 has wet with blood. Once first chamber 544 is filled with blood, blood will flow from the top of first chamber 544 into front cross port 507, through inlet port 509, through outlet tubing 53, into receiving blood bag 55. Any additional air that is forced through the filter elements into first chamber 544 by blood flowing through and wetting the top portion of the filter elements will bubble to the top of first chamber 544 (because of the buoyancy of air in the blood) and be forced out of first chamber 544, into front cross port 507, through inlet port 509, through outlet tubing 53, into receiving blood bag 55, by the flow of blood from first chamber 544 into front cross port 507, through inlet port 509. This assures that filter elements 83, 82, 81, and 80 will completely wet, and that all of the air that was in second chamber 547, filter elements 83, 82, 81, and 80, first chamber 544, front cross port 507, inlet port 509, and the interior of outlet tubing 53 will be forced into receiving blood bag 55. Because there is no siphon tube in first chamber 544, all of the air will be purged from within the filter device by the positive pressure within the filter device, and by the flow of blood through the filter device created by the positive pressure in second chamber 547. The initial air in second chamber 547a, filter elements 83a, 82a, 81a, 80a, and first chamber 545 will be purged as just described.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in inlet port 509 will be negative, as will be the pressure head in first chamber 544, and first chamber 545, all of body 501. Once blood flow has stopped the pressure drop across filter elements 83, 82, 81, and 80, will fall to zero. The pressure drop across filter elements 83a, 82a, 81a, and 80a, will also fall to zero. Hence the pressure in second chamber 547 and second chamber 547a will become negative. The pressure in through slot 506, outlet port 511, and inlet tubing 52 will also be negative. If a means (not shown) is provided to allow sterile air to enter inlet tubing 52 after filtration is complete, the portion of inlet tubing below the point of sterile air entry, along with outlet port 511, through slot 506, second chamber 547, and second chamber 547a will drain until second chamber 547 and second chamber 547a are empty, and blood will remain in filter elements 83, 82, 81, 80, 83a, 82a, 81a, and 80a, first chamber 544, first chamber 545, front cross port 507, back cross port 507a, inlet port 509, and in outlet tubing 53. If a means is not provided to allow sterile air to enter inlet tubing 52 after filtration is complete, blood will remain in inlet tubing 52, outlet port 511, through slot 506, second chamber 547, second chamber 547a, filter elements 83, 82, 81, 80, 83a, 82a, 81a, and 80a, first chamber 544, first chamber 545, front cross port 507, back cross port 507a, inlet port 509, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 540 can now be discarded in a safe manner. Outlet tubing 53 will have segments marked on it. The user can now seal the outlet tubing at the segment marks. The blood that is left in outlet tubing 53 will be used for cross matching and for quality control purposes.

Referring to FIG. 36 and FIG. 39, when filter device 540 is used with the inlet port and the outlet port transposed as just described, a first fluid flow path is defined between outlet port 511 of filter device 540 and inlet port 509 of filter device 540 with the first filtration media interposed between outlet port 511 and inlet port 509, and across the first fluid flow path. The first fluid flow path flows from outlet port 511, into through slot 506, into second chamber 547, through the first filtration media, into first chamber 544, through front cross port 507, into inlet port 509. A second fluid flow path is defined between outlet port 511 of filter device 540 and inlet port 509 of filter device 540 with the second filtration media interposed between outlet port 511 and inlet port 509, and across the second fluid flow path. The second fluid flow path flows from outlet port 511, into through slot 506, into second chamber 547a, through the second filtration media, into first chamber 545, through back cross port 507a, into inlet port 509.

When filter device 540 is used with the inlet port and the outlet port transposed as just described, it is be desirable to make second chamber 547 and second chamber 547a deeper, and to make first chamber 544 and first chamber 545 shallower than shown in FIG. 39, thereby transposing the depths of the first and second chambers.

Figure 40:
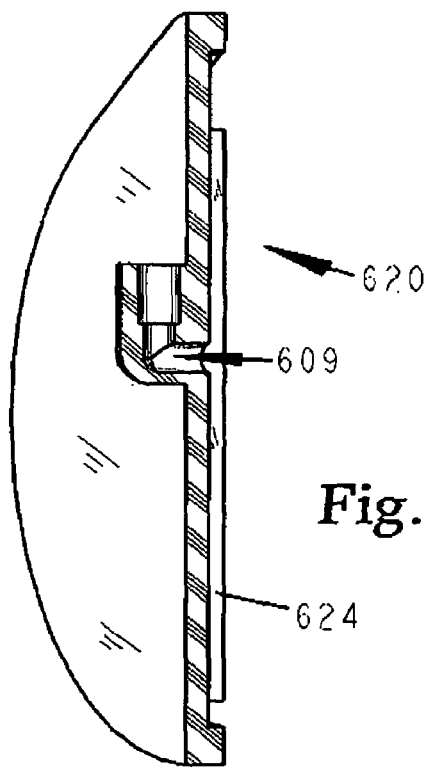
FIG. 40 is an isometric view, having portions thereof removed, of the front cover of the filtration apparatus depicted in FIG. 42.
Figure 42:
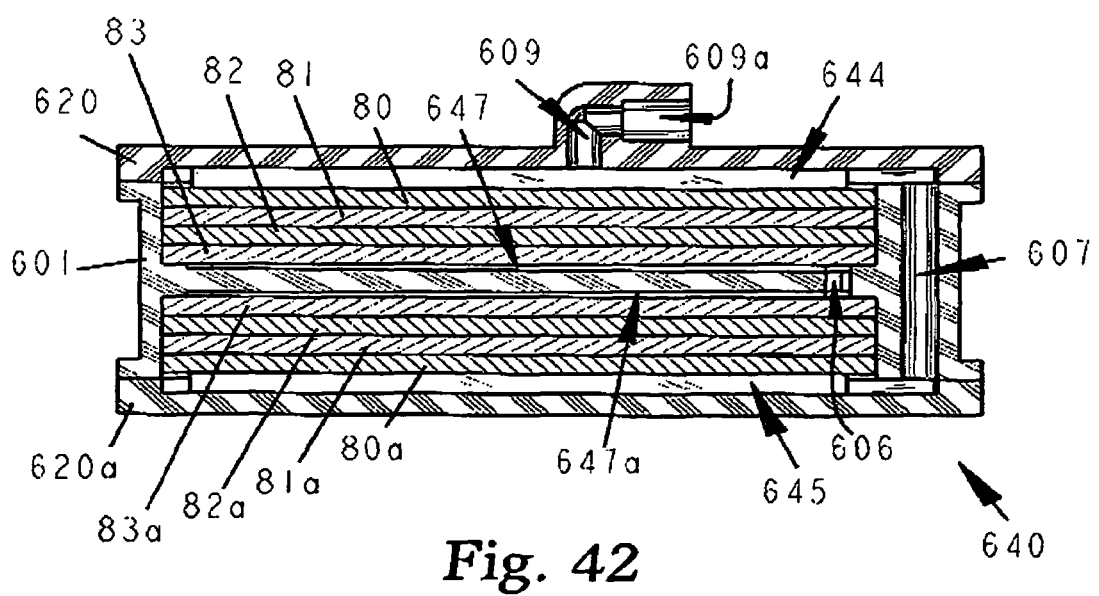
FIG. 42 is a cross-sectional view of the ninth embodiment of the filtration apparatus, constructed in accordance with the principles of the present invention, usable for the filtration of blood and blood products.

A ninth embodiment of the filtration device constructed in accordance with the principles of the present invention, is shown in FIG. 40, through FIG. 42. FIG. 40 shows a cross-sectional view of filter device 640, with the plane of the cross-section intersecting the central axis of cross port 607. Filter device 640 includes the following components: front cover 620, body 601, back cover 620a, filter elements 80, 81, 82, 83, 80a, 81a, 82a, and 83a. Body 601 is identical to body 501 except that body 601 does not contain an inlet tube socket protrusion, an inlet port, or an inlet tube socket. Because cross port 607 is not divided by an inlet port it is referred to as cross port 607, not as front cross port 607 and back cross port 607a. Front cover 620 is identical to front cover 520 except that front cover 620 contains inlet port 609, and inlet tube socket 609a. Inlet port 609 is shown located above the center of first chamber 644, and on the vertical center line of first chamber 644. Inlet port 609 could however be located on front cover any where from the bottom to the top of first chamber 644, and to the right or to the left of the vertical center line of first chamber 644. Back cover 620a is identical to back cover 520a. Filter elements 80, 81, 82, and 83 shown in FIG. 42 are sealed to filter device 640 with a compression fit between the outer edge of each respective filter element and the side wall of the first filter well, and filter elements 80a, 81a, 82a, and 83a, are sealed to filter device 640 with a compression fit between the outer edge of each respective filter element and the side wall of the second filter well. The first and second filter compression rings used in filter device 540 are eliminated in filter device 640.

Figure 41:
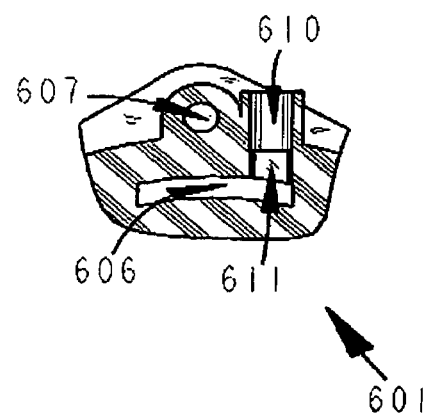
FIG. 41 is a partial cross-sectional view of the body of the filtration apparatus depicted in FIG. 42, showing the top part of the body.

Referring to FIG. 41 and FIG. 42 a first fluid flow path is defined between inlet port 609 of filter device 640 and outlet port 611 of filter device 640 with the first filtration media interposed between inlet port 609 and outlet port 611, and across the first fluid flow path. The first fluid flow path flows from inlet port 609, into first chamber 644, through the first filtration media, into second chamber 647, into through slot 606, into outlet port 611. A second fluid flow path is defined between inlet port 609 of filter device 640 and outlet port 611 of filter device 640 with the second filtration media interposed between inlet port 609 and outlet port 611, and across the second fluid flow path. The second fluid flow path flows from inlet port 609, through first chamber 644, through cross port 607, into first chamber 645, through the second filtration media, into second chamber 647a, into through slot 606, into outlet 611. The first filtration media contains filter elements 80, 81, 82, and 83. The second filtration media contains filter elements 80a, 81a, 82a, and 83a.

Filter device 640 could replace filter device 40 of assembly 60 shown in FIG. 9. Referring to FIG. 40 through FIG. 42 the filtration with filter device 640 replacing filter device 40 in FIG. 9 is performed as follows. The user opens inlet tube clamp 74. Gravity now forces blood to flow from feed blood bag 54, through inlet tubing 52, through inlet port 609, into first chamber 644, filling first chamber 644 from the bottom up. One end of cross port 607 is located within first chamber 644, with the other end of cross port 607 located within first chamber 645. Therefore, once first chamber 644 has filled with blood, blood will flow through cross port 607, and fill first chamber 645 from the bottom up. The air that was initially in inlet tubing 52, inlet port 609, first chamber 644, cross port 607, and first chamber 645 will be forced through filter elements 80, 81, 82, and 83, into second chamber 647, and through filter elements 80a, 81a, 82a, and 83a, into second chamber 647a, and then from second chamber 647 and second chamber 647a, into through slot 606, through outlet port 611, through outlet tubing 53, into receiving blood bag 55.

The initial air that enters second chamber 647 from filter elements 80, 81, 82, and 83, plus all of the initial air that was in second chamber 647 will be forced from second chamber 647, into through slot 606, through outlet port 611, through outlet tubing 53, into receiving blood bag 55. Because the volume of first chamber 644 is small, and the flow rate of blood entering first chamber 644 is greater than the initial flow rate of blood through filter elements 80, 81, 82, and 83, first chamber 644 will fill in a fraction of the time that it takes to wet filter elements 80, 81, 82, and 83. The pressure head at the bottom of first chamber 644 will be larger than the pressure head at the top of first chamber 644, because of the height difference between the top and bottom of first chamber 644. Therefore liquid will start to come through filter element 83 into second chamber 647 from the bottom up. As second chamber 647 fills from the bottom up with blood the remaining air in second chamber 647 will be forced from second chamber 647, into through slot 606, through outlet port 611, through outlet tubing 53, into receiving blood bag 55. Because the total volume of second chamber 647 is small (to minimize holdup) second chamber 647 may fill with blood (from the bottom up) before the upper part of filter element 83 has wet with blood. Once second chamber 647 is filled with blood, the blood will flow from the top of second chamber 647 into through slot 606, through outlet port 611, through outlet tubing 53, into receiving blood bag 55. Any additional air that is forced through the filter elements into second chamber 647 by blood flowing through and wetting the top portion of the filter elements will bubble to the top of second chamber 647 (because of the buoyancy of air in the blood) and be forced out of second chamber 647, into through slot 606, through outlet port 611, through outlet tubing 53, into receiving blood bag 55, by the flow of blood from second chamber 647, into through slot 606, through outlet port 611. This assures that filter elements 80, 81, 82, and 83 will completely wet, and that all of the air that was in first chamber 644, filter elements 80, 81, 82, and 83, second chamber 647, through slot 606, outlet port 611, and the interior of outlet tubing 53 will be forced into receiving blood bag 55. Because there is no siphon tube in second chamber 647, all of the air will be purged from within the filter device by the positive pressure within the filter device, and by the flow of blood through the filter device created by the positive pressure in first chamber 644. The initial air in first chamber 645, filter elements 80a, 81a, 82a, 83a, and second chamber 647a will be also purged as just described.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in outlet port 611 will be negative, as will be the pressure head in second chamber 647, and second chamber 647a, all of body 601. Once blood flow has stopped the pressure drop across filter elements 80, 81, 82, and 83, will fall to zero. The pressure drop across filter elements 80a, 81a, 82a, and 83a, will also fall to zero. Hence the pressure in first chamber 644 and the pressure in first chamber 645 will become negative. The pressure in inlet port 609, and inlet tubing 52 will also be negative. If a means (not shown) is provided to allow sterile air to enter inlet tubing 52 after filtration is complete, the portion of inlet tubing below the point of sterile air entry, along with inlet port 609, first chamber 644, first chamber 645, and cross port 607, will drain until first chamber 644, first chamber 645, and cross port 607 are empty, and blood will remain in filter elements 80, 81, 82, 83, 80a, 81a, 82a, and 83a, second chamber 647, second chamber 647a, through slot 606, outlet port 611, and in outlet tubing 53. If a means is not provided to allow sterile air to enter inlet tubing 52 after filtration is complete, blood will remain in inlet tubing 52, inlet port 611, first chamber 644, first chamber 645, cross port 607, filter elements 80, 81, 82, 83, 80a, 81a, 82a, and 83a, second chamber 647, second chamber 647a, through slot 606, outlet port 611, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 640 can now be discarded in a safe manner. Outlet tubing 53 will have segments marked on it. The user can now seal the outlet tubing at the segment marks. The blood that is left in outlet tubing 53 will be used for cross matching and for quality control purposes.

A tenth embodiment of the filtration device constructed in accordance with the principles of the present invention, is shown in FIG. 43. FIG. 43 shows a cross-sectional view of filter device 740, with the plane of the cross-section intersecting the central axis of outlet port 711, first inlet port 709, and second inlet port 709a. Filter device 740 includes the following components: front cover 720, body 701, back cover 720a, filter elements 80, 81, 82, 83, 80a, 81a, 82a, and 83a. Body 701 is identical to body 501 except that body 701 does not contain an inlet tube socket protrusion, an inlet port, an inlet tube socket, a cross port protrusion, a cross port, or a front and back flange, and outlet port 711 is located on the center vertical axis of body 701. Body 701 is identical to body 901 shown in FIG. 45 and FIG. 46, with the exception that inlet port 909 of body 901 is replaced with outlet port 711 of body 701, and that second chambers 947 and 947a of body 901 are deeper than second chambers 747 and 747a of body 701. Front cover 720 is round in shape to match body 701, and contains first inlet port 709, and is otherwise identical to front cover 620. First inlet port 709 is shown located above the center of first chamber 744, and on the vertical center line of first chamber 744. First inlet port 709 could however be located on front cover 720 anywhere from the bottom to the top of first chamber 744, and to the right or to the left of the vertical center line of first chamber 744. Back cover 720a is identical to front cover 720. Back cover 720a contains second inlet port 709a. Filter elements 80, 81, 82, and 83 shown in FIG. 43 are sealed to filter device 740 with a compression fit between the outer edge of each respective filter element and the side wall of the first filter well, and filter elements 80a, 81a, 82a, and 83a, are sealed to filter device 740 with a compression fit between the outer edge of each respective filter element and the side wall of the second filter well. In addition first filter compression ring 795 compresses the outer periphery of filter element 80, thereby sealing filter element 80 to filter device 740 with a second seal. Second filter compression ring 795a compresses the outer periphery of filter element 80a, thereby sealing filter element 80a to filter device 740 with a second seal.

Referring to FIG. 43, outlet port 711 is located at the top of filter device 740. The arrow labeled UP in FIG. 43 indicates the upward direction, toward the feed blood bag. A first fluid flow path is defined between first inlet port 709 of filter device 740 and outlet port 711 of filter device 740 with the first filtration media interposed between first inlet port 709 and outlet port 711, and across the first fluid flow path. The first fluid flow path flows from first inlet port 709, into first chamber 744, through the first filtration media, into second chamber 747, into through slot 706, into outlet port 711. A second fluid flow path is defined between second inlet port 709a of filter device 740 and outlet port 711 of filter device 740 with the second filtration media interposed between second inlet port 709a and outlet port 711, and across the second fluid flow path. The second fluid flow path flows from second inlet port 709a, into first chamber 745, through the second filtration media, into second chamber 747a, into through slot 706, into outlet port 711. The first filtration media contains filter elements 80, 81, 82, and 83. The second filtration media contains filter elements 80a, 81a, 82a, and 83a.

Filter device 740 contains two inlet ports and two inlet tube sockets. Therefore, if a single feed blood bag is to be used in the filtration process, the first inlet tube socket of filter device 740 could be connected to a first connector of a tubing Tee via a first length of tubing, the second inlet tube socket of filter device 740 could be connected to a second connector of a tubing Tee via a second length of tubing, and the length of tubing coming from the feed blood bag could connect to the third connector of the tubing Tee, thereby placing the first inlet port in fluid flow communication with the second inlet port, and placing both inlet ports in fluid flow communication with the feed blood bag. A tubing Y could replace the tubing Tee. Alternately if two units of blood from different feed blood bags are to be used, the first feed blood bag could be connected to the first inlet tube socket of filter device 740, and the second feed blood bag could be connected to the second inlet tube socket of filter device 740.

Filter device 740 could replace filter device 40 of assembly 60 shown in FIG. 9. Referring to FIG. 43, the filtration with filter device 740 replacing filter device 40 in FIG. 9 is performed as follows, assuming that the first inlet port is in fluid flow communication with the second inlet port as just described. The user opens inlet tube clamp 74. Gravity now forces blood to flow from feed blood bag 54, through inlet tubing 52, through first inlet port 709, into first chamber 744, filling first chamber 744 from the bottom up. The air that was initially in inlet tubing 52, first inlet port 709, and first chamber 744, will be forced through filter elements 80, 81, 82, and 83, into second chamber 747, and then from second chamber 747, into through slot 706, through outlet port 711, through outlet tubing 53, into receiving blood bag 55. Outlet port 711 and the outlet tube socket are located at the top of filter device 740. Therefore a loop must be formed in the end of outlet tubing 53 that is bonded to the outlet tube socket so that outlet tubing 53 can change direction from upward as it comes out of the outlet tube socket to downward toward the receiving blood bag. Referring to FIG. 43, the arrow labeled UP shows the upward direction of filter device 740, that is the direction toward the feed blood bag.

The initial air that enters second chamber 747 from filter elements 80, 81, 82, and 83, plus all of the initial air that was in second chamber 747 will be forced from second chamber 747, into through slot 706, through outlet port 711, through outlet tubing 53, into receiving blood bag 55. Because the volume of first chamber 744 is small, and the flow rate of blood entering first chamber 744 is greater than the initial flow rate of blood through filter elements 80, 81, 82, and 83, first chamber 744 will fill in a fraction of the time that it takes to wet filter elements 80, 81, 82, and 83. The pressure head at the bottom of first chamber 744 will be larger than the pressure head at the top of first chamber 744, because of the height difference between the top and bottom of first chamber 744. Therefore liquid will start to come through filter element 83 into second chamber 747 from the bottom up. As second chamber 747 fills from the bottom up with blood the remaining air in second chamber 747 will be forced from second chamber 747, into through slot 706, through outlet port 711, through outlet tubing 53, into receiving blood bag 55. Because the total volume of second chamber 747 is small (to minimize holdup) second chamber 747 may fill with blood (from the bottom up) before the upper part of filter element 83 has wet with blood. Once second chamber 747 is filled with blood, blood will flow from the top of second chamber 747 into through slot 706, through outlet port 711, through outlet tubing 53, into receiving blood bag 55. Any additional air that is forced through the filter elements into second chamber 747 by blood flowing through and wetting the top portion of the filter elements will bubble to the top of second chamber 747 (because of the buoyancy of air in the blood) and be forced out of second chamber 747, into through slot 706, through outlet port 711, through outlet tubing 53, into receiving blood bag 55, by the flow of blood from second chamber 747 into through slot 706, through outlet port 711. This assures that filter elements 80, 81, 82, and 83 will completely wet, and that all of the air that was in first chamber 744, filter elements 80, 81, 82, and 83, second chamber 747, through slot 706, outlet port 711, and the interior of outlet tubing 53 will be forced into receiving blood bag 55. Because there is no siphon tube in second chamber 747, all of the air will be purged from within the filter device by the positive pressure within the filter device, and by the flow of blood through the filter device created by the positive pressure in first chamber 744. The initial air in first chamber 745, filter elements 80a, 81a, 82a, 83a, and second chamber 747a will be purged as just described.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in outlet port 711 will be negative, as will be the pressure head in second chamber 747, and second chamber 747*a*, all of body 701. Once blood flow has stopped the pressure drop across filter elements 80, 81, 82, and 83, will fall to zero. The pressure drop across filter elements 80*a*, 81*a*, 82*a*, and 83*a*, will also fall to zero. Hence the pressure in first chamber 744 and the pressure in first chamber 745 will become negative. The pressure in first inlet port 709, second inlet port 709*a*, and inlet tubing 52 will also be negative. If a means (not shown) is provided to allow sterile air to enter inlet tubing 52 after filtration is complete, the portion of inlet tubing below the point of sterile air entry, along with first inlet port 709, first chamber 744, second inlet port 709*a*, and first chamber 745, will drain until first chamber 744, and first chamber 745, are empty, and blood will remain in filter elements 80, 81, 82, 83, 80*a*, 81*a*, 82*a*, and 83*a*, second chamber 747, second chamber 747*a*, through slot 706, outlet port 711, and in outlet tubing 53. If a means is not provided to allow sterile air to enter inlet tubing 52 after filtration is complete, blood will remain in inlet tubing 52, first inlet port 709, first chamber 744, second inlet port 709*a*, first chamber 745, filter elements 80, 81, 82, 83, 80*a*, 81*a*, 82*a*, and 83*a*, second chamber 747, second chamber 747*a*, through slot 706, outlet port 711, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 740 can now be discarded in a safe manner. Outlet tubing 53 will have segments marked on it. The user can now seal the outlet tubing at the segment marks. The blood that is left in outlet tubing 53 will be used for cross matching and for quality control purposes.

An eleventh embodiment of the filtration device constructed in accordance with the principles of the present invention, is shown in FIG. 44. FIG. 44 shows a cross-sectional view of filter device 840, with the plane of the cross-section intersecting the central axis of inlet port 809, first outlet port 811, and second outlet port 811*a*. Filter device 840 includes the following components: front cover 820, body 801, back cover 820*a*, filter elements 80, 81, 82, 83, 80*a*, 81*a*, 82*a*, and 83*a*. Referring to FIG. 33, FIG. 44, FIG. 45, and FIG. 46, body 801 is identical to body 501 except that body 801 does not contain a cross port protrusion, a cross port, or a front and back flange, and that inlet port 809 of body 801 replaces outlet port 511 of body 501. Inlet port 809 is located on the center vertical axis of body 801. Body 801 is identical to body 901 shown in FIG. 45 and FIG. 46, with the exception that second chambers 947 and 947*a* of body 901 are deeper than second chambers 847 and 847*a* of body 801. Front cover 820 is round in shape to match body 801, and contains first outlet port 811. Front cover 820 also contains filter support ribs 824 that are the same as filter support ribs 524 of front cover 520. First outlet port 811 is shown located at the top of first chamber 844, and on the vertical center line of first chamber 844. Back cover 820*a* is identical to front cover 820. Back cover 820*a* contains second outlet port 811*a*. Filter elements 80, 81, and 82, are shown in FIG. 44 are sealed to filter device 840 with a compression fit between the outer edge of each respective filter element and the side wall of the first filter well, and filter elements 80*a*, 81*a*, and 82*a*, are sealed to filter device 840 with a compression fit between the outer edge of each respective filter element and the side wall of the second filter well. In addition first filter compression ring 895 compresses the outer periphery of filter element 80, thereby sealing filter element 80 to filter device 840 with a second seal. Filter element 80*a* is also sealed to filter device 840 with a second seal. Filter element 83 has an outside diameter smaller than the inside diameter of the side wall of the first filter well. Therefore filter element 83 can not be sealed to the first filter well with a compression fit between the outer edge of filter element 83 and the side wall of the first filter well. Filter element 83 is sealed to filter device 840 by compressing the downstream outer periphery of filter element 83 against filter seal surface 802. Filter element 83*a* is sealed to filter device 840 in the same manner as filter element 83.

Referring to FIG. 44, inlet port 809 is located at the top of filter device 840. The arrow labeled UP in FIG. 44 indicates the upward direction, toward the feed blood bag. A first fluid flow path is defined between inlet port 809 of filter device 740 and first outlet port 811 of filter device 840 with the first filtration media interposed between inlet port 809 and first outlet port 811, and across the first fluid flow path. The first fluid flow path flows from inlet port 809, into through slot 806, into second chamber 847, through the first filtration media, into first chamber 844, into first outlet port 811. A second fluid flow path is defined between inlet port 809 of filter device 840 and second outlet port 811*a* of filter device 840 with the second filtration media interposed between inlet port 809 and second outlet port 811*a*, and across the second fluid flow path. The second fluid flow path flows from inlet port 809, into through slot 806, into second chamber 847*a*, through the second filtration media, into first chamber 845, into second outlet port 811*a*. The first filtration media contains filter elements 80, 81, 82, and 83. The second filtration media contains filter elements 80*a*, 81*a*, 82*a*, and 83*a*.

Filter device 840 contains two outlet ports and two outlet tube sockets. Therefore, if a single receiving blood bag is to be used in the filtration process, the first outlet tube socket of filter device 840 could be connected to a first connector of a tubing Tee via a first length of tubing, the second outlet tube socket of filter device 840 could be connected to a second connector of a tubing Tee via a second length of tubing, and the length of tubing coming from the receiving blood bag could connect to the third connector of the tubing Tee, thereby placing the first outlet port in fluid flow communication with the second outlet port, and placing both outlet ports in fluid flow communication with the receiving blood bag. A tubing Y could replace the tubing Tee. Alternately if two units of blood are to be filtered, a first receiving blood bag could be connected to the first outlet tube socket of filter device 840, and the second receiving blood bag could be connected to the second outlet tube socket of filter device 840.

Filter device 840 could replace filter device 40 of assembly 60 shown in FIG. 9. Referring to FIG. 44, the filtration with filter device 840 replacing filter device 40 in FIG. 9 is performed as follows, assuming that the first outlet port is in fluid flow communication with the second outlet port as just described. The user opens inlet tube clamp 74. Gravity now forces blood to flow from feed blood bag 54, through inlet tubing 52, through inlet port 809, into through slot 806. A portion of the blood then passes from through slot 806 into second chamber 847, while the remainder of the blood passes from through slot 806 into second chamber 847*a*. A portion of the air that was in inlet tubing 52 and inlet port 809 before blood flow started will be pushed ahead of the blood, into through slot 806, into second chamber 847 of filter device 840. The remainder of the air that was in inlet tubing 52 and inlet port 809 before blood flow started will be pushed ahead of the blood, into through slot 806, and then into second chamber 847a of filter device 840. All of the air that is forced into second chamber 847 by blood flow from the blood bag, and all of the air that was initially in second chamber 847 will be forced by the positive pressure (due to the blood flow) in second chamber 847, through filter elements 83, 82, 81, and 80, into first chamber 844, through first outlet port 811, through outlet tubing 53, into receiving blood bag 55; and all of the air that is forced into second chamber 847a by blood flow from the blood bag, and all of the air that was initially in second chamber 847a will be forced by the positive pressure (due to the blood flow) in second chamber 847a, through filter elements 83a, 82a, 81a, and 80a, into first chamber 845, through second outlet port 811a, through outlet tubing 53, into receiving blood bag 55.

As second chamber 847 of filter device 840 fills from the bottom up all of the air in second chamber 847 will be forced (by the positive pressure in second chamber 847) through filter elements 83, 82, 81, and 80, for the same reasons described in the previous paragraph. This initial air will flow into first chamber 844 of filter device 840. The top of first chamber 844 is in fluid flow communication with first outlet port 811. The initial air that enters second chamber 844 from filter elements 83, 82, 81, and 80 plus all of the initial air that was in first chamber 844 will be forced from first chamber 844, through first outlet port 811, through outlet tubing 53, into receiving blood bag 55. Because the volume of second chamber 847 is small, and the flow rate of blood entering second chamber 847 is greater than the initial flow rate of blood through filter elements 83, 82, 81, and 80, second chamber 847 will fill in a fraction of the time that it takes to wet filter elements 83, 82, 81, and 80. The pressure head at the bottom of second chamber 847 will be larger than the pressure head at the top of second chamber 847, because of the height difference between the top and bottom of second chamber 847. Therefore liquid will start to come through filter element 80 into first chamber 844 from the bottom up. As first chamber 844 fills from the bottom up with blood the remaining air in first chamber 844 will be forced from first chamber 844, through first outlet port 811, through outlet tubing 53, into receiving blood bag 55. Because the total volume of first chamber 844 is small (to minimize holdup) first chamber 844 may fill with blood (from the bottom up) before the upper part of filter element 80 has wet with blood. Once first chamber 844 is filled with blood, blood will flow from the top of first chamber 844, through first outlet port 811, through outlet tubing 53, into receiving blood bag 55. Any additional air that is forced through the filter elements into first chamber 844 by blood flowing through and wetting the top portion of the filter elements will bubble to the top of first chamber 844 (because of the buoyancy of air in the blood) and be forced out of first chamber 844, through first outlet port 811, through outlet tubing 53, into receiving blood bag 55, by the flow of blood from first chamber 844, through first outlet port 811. This assures that filter elements 83, 82, 81, and 80 will completely wet, and that all of the air that was in second chamber 847, filter elements 83, 82, 81, and 80, first chamber 844, first outlet port 811, and the interior of outlet tubing 53 will be forced into receiving blood bag 55. Because there is no siphon tube in first chamber 844, all of the air will be purged from within the filter device by the positive pressure within the filter device, and by the flow of blood through the filter device created by the positive pressure in second chamber 847. The initial air in second chamber 847a, filter elements 83a, 82a, 81a, 80a, and first chamber 845 will be purged as just described.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in first outlet port 811, first chamber 844, second outlet port 811a, and first chamber 845, will be negative. Once blood flow has stopped the pressure drop across filter elements 83, 82, 81, and 80, will fall to zero. The pressure drop across filter elements 83a, 82a, 81a, and 80a, will also fall to zero. Hence the pressure in second chamber 847 and second chamber 847a will become negative. The pressure in through slot 806, inlet port 809, and inlet tubing 52 will also be negative. If a means (not shown) is provided to allow sterile air to enter inlet tubing 52 after filtration is complete, the portion of inlet tubing below the point of sterile air entry, along with inlet port 809, through slot 806, second chamber 847, and second chamber 847a will drain until second chamber 847 and second chamber 847a are empty, and blood will remain in filter elements 83, 82, 81, 80, 83a, 82a, 81a, and 80a, first chamber 844, first chamber 845, first outlet port 811, second outlet port 811a, and in outlet tubing 53. If a means is not provided to allow sterile air to enter inlet tubing 52 after filtration is complete, blood will remain in inlet tubing 52, inlet port 809, through slot 806, second chamber 847, second chamber 847a, filter elements 83, 82, 81, 80, 83a, 82a, 81a, and 80a, first chamber 844, first chamber 845, first outlet port 811, second outlet port 811a, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 840 can now be discarded in a safe manner. Outlet tubing 53 will have segments marked on it. The user can now seal the outlet tubing at the segment marks. The blood that is left in outlet tubing 53 will be used for cross matching and for quality control purposes.

Figure 45:
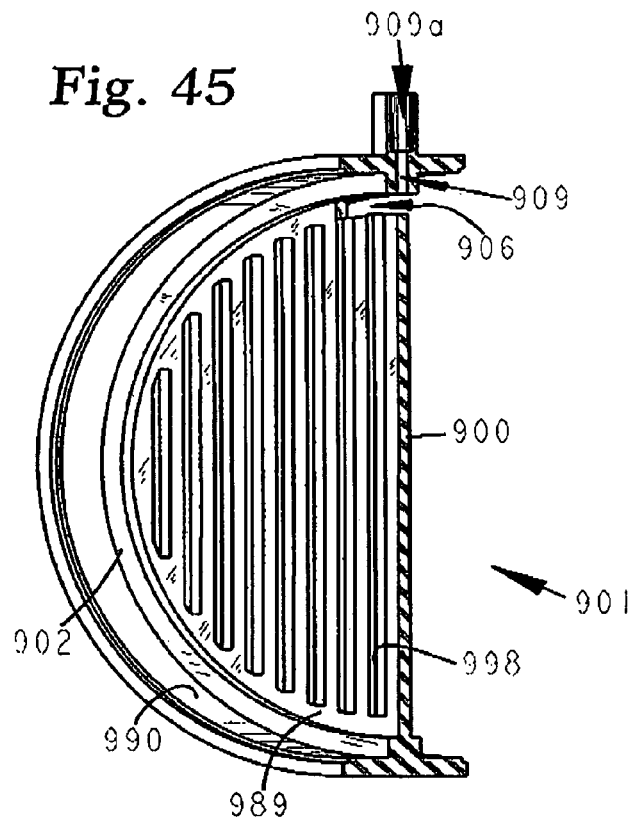
FIG. 45 is a cross-sectional view, having portions thereof removed, of the body of the filtration apparatus depicted in FIG. 43, and of the filtration apparatus depicted in FIG. 44, and of the filtration apparatus depicted in FIG. 46.
Figure 46:
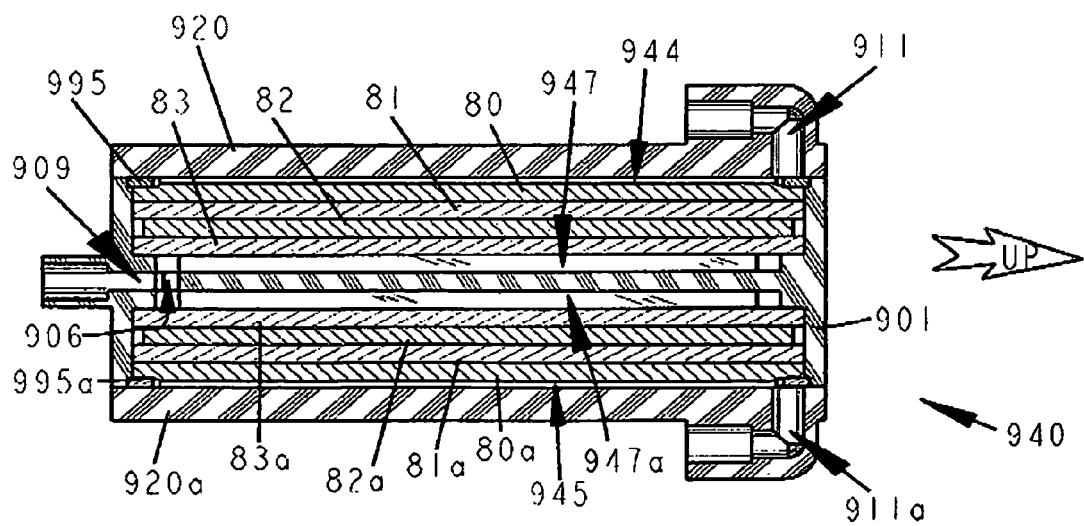
FIG. 46 is a cross-sectional view of the twelfth embodiment of the filtration apparatus, constructed in accordance with the principles of the present invention, usable for the filtration of blood and blood products.

An twelfth embodiment of the filtration device constructed in accordance with the principles of the present invention, is shown in FIG. 45 and FIG. 46. FIG. 46 shows a cross-sectional view of filter device 940, with the plane of the cross-section intersecting the central axis of inlet port 909, first outlet port 911, and second outlet port 911a. Filter device 940 includes the following components: front cover 920, body 901, back cover 920a, filter elements 80, 81, 82, 83, 80a, 81a, 82a, and 83a. Referring to FIG. 44, FIG. 45, and FIG. 46, body 901 is identical to body 801 except that second chambers 947 and 947a of body 901 are deeper than second chambers 847 and 847a of body 801. Front cover 920 is round in shape to match body 901, and contains first outlet port 911. First outlet port 911 is shown located at the top of first chamber 944, and on the vertical center line of first chamber 944. Front cover 920 is identical to front cover 820 with the exception that first chamber 944 of front cover 920 is not as deep as first chamber 844 of front cover 820. Back cover 920a is identical to front cover 920. Back cover 920a contains second outlet port 911a. Filter elements 80, 81, and 83, are shown in FIG. 46 are sealed to filter device 940 with a compression fit between the outer edge of each respective filter element and the side wall of the first filter well, and filter elements 80a, 81a, and 83a, are sealed to filter device 940 with a compression fit between the outer edge of each respective filter element and the side wall of the second filter well. In addition first filter compression ring 995 compresses the outer periphery of filter element 80, thereby sealing filter element 80 to filter device 940 with a second seal. Filter element 80a is also sealed to filter device 940 with a second seal. Filter element 82 has an outside diameter smaller than the inside diameter of the side wall of the first filter well. Therefore filter element 82 can not be sealed to the first filter well with a compression fit between the outer edge of filter element 82 and the side wall of the first filter well. Filter element 82 is compressed between filter element 81 and filter element 83. Filter element 82a is compressed between filter element 81a and filter element 83a.

Referring to FIG. 46, inlet port 909 is located at the bottom of filter device 940. The arrow labeled UP in FIG. 46 indicates the upward direction, toward the feed blood bag. A first fluid flow path is defined between inlet port 909 of filter device 940 and first outlet port 911 of filter device 940 with the first filtration media interposed between inlet port 909 and first outlet port 911, and across the first fluid flow path. The first fluid flow path flows from inlet port 909, into through slot 906, into second chamber 947, through the first filtration media, into first chamber 944, into first outlet port 911. A second fluid flow path is defined between inlet port 909 of filter device 940 and second outlet port 911a of filter device 940 with the second filtration media interposed between inlet port 909 and second outlet port 911a, and across the second fluid flow path. The second fluid flow path flows from inlet port 909, into through slot 906, into second chamber 947a, through the second filtration media, into first chamber 945, into second outlet port 911a. The first filtration media contains filter elements 80, 81, 82, and 83. The second filtration media contains filter elements 80a, 81a, 82a, and 83a.

Filter device 940 contains two outlet ports and two outlet tube sockets. Therefore, if a single receiving blood bag is to be used in the filtration process, the first outlet tube socket of filter device 940 could be connected to a first connector of a tubing Tee via a first length of tubing, the second outlet tube socket of filter device 940 could be connected to a second connector of a tubing Tee via a second length of tubing, and the length of tubing coming from the receiving blood bag could connect to the third connector of the tubing Tee, thereby placing the first outlet port in fluid flow communication with the second outlet port, and placing both outlet ports in fluid flow communication with the receiving blood bag. A tubing Y could replace the tubing Tee. Alternately if two units of blood are to be filtered, a first receiving blood bag could be connected to the first outlet tube socket of filter device 940, and a second receiving blood bag could be connected to the second outlet tube socket of filter device 940.

Filter device 940 could replace filter device 40 of assembly 60 shown in FIG. 9. Inlet port 909 and the inlet tube socket are located at the bottom of filter device 940. Therefore a loop must be formed in the end of inlet tubing 52 that is bonded to the inlet tube socket so that inlet tubing 52 can change direction from downward as it comes from the feed blood bag to upward to inlet port 909. Referring to FIG. 46, the filtration with filter device 940 replacing filter device 40 in FIG. 9 is performed as follows, assuming that the first outlet port is in fluid flow communication with the second outlet port as just described. The user opens inlet tube clamp 74. Gravity now forces blood to flow from feed blood bag 54, through inlet tubing 52, through inlet port 909, into through slot 906. A portion of the blood then passes from through slot 906 into second chamber 947, while the remainder of the blood passes from through slot 906 into second chamber 947a. A portion of the air that was in inlet tubing 52 and inlet port 909 before blood flow started will be pushed ahead of the blood, into through slot 906, into second chamber 947 of filter device 940. The remainder of the air that was in inlet tubing 52 and inlet port 909 before blood flow started will be pushed ahead of the blood, into through slot 906, and then into second chamber 947a of filter device 940. All of the air that is forced into second chamber 947 by blood flow from the blood bag, and all of the air that was initially in second chamber 947 will be forced by the positive pressure (due to the blood flow) in second chamber 947, through filter elements 83, 82, 81, and 80, into first chamber 944, through first outlet port 911, through outlet tubing 53, into receiving blood bag 55; and all of the air that is forced into second chamber 947a by blood flow from the blood bag, and all of the air that was initially in second chamber 947a will be forced by the positive pressure (due to the blood flow) in second chamber 947a, through filter elements 83a, 82a, 81a, and 80a, into first chamber 945, through second outlet port 911a, through outlet tubing 53, into receiving blood bag 55.

As second chamber 947 of filter device 940 fills from the bottom up all of the air in second chamber 947 will be forced (by the positive pressure in second chamber 947) through filter elements 83, 82, 81, and 80, for the same reasons described in the previous paragraph. This initial air will flow into first chamber 944 of filter device 940. The top of first chamber 944 is in fluid flow communication with first outlet port 911. The initial air that enters first chamber 944 from filter elements 83, 82, 81, and 80 plus all of the initial air that was in first chamber 944 will be forced from first chamber 944, through first outlet port 911, through outlet tubing 53, into receiving blood bag 55. Because the volume of second chamber 947 is small, and the flow rate of blood entering second chamber 947 is greater than the initial flow rate of blood through filter elements 83, 82, 81, and 80, second chamber 947 will fill in a fraction of the time that it takes to wet filter elements 83, 82, 81, and 80. The pressure head at the bottom of second chamber 947 will be larger than the pressure head at the top of second chamber 947, because of the height difference between the top and bottom of second chamber 947. Therefore liquid will start to come through filter element 80 into first chamber 944 from the bottom up. As first chamber 944 fills from the bottom up with blood, the remaining air in first chamber 944 will be forced from first chamber 944, through first outlet port 911, through outlet tubing 53, into receiving blood bag 55. Because the total volume of first chamber 944 is small (to minimize holdup) first chamber 944 may fill with blood (from the bottom up) before the upper part of filter element 80 has wet with blood. Once first chamber 944 is filled with blood, blood will flow from the top of first chamber 944, through first outlet port 911, through outlet tubing 53, into receiving blood bag 55. Any additional air that is forced through the filter elements into first chamber 944 by blood flowing through and wetting the top portion of the filter elements will bubble to the top of first chamber 944 (because of the buoyancy of air in the blood) and be forced out of first chamber 944, through first outlet port 911, through outlet tubing 53, into receiving blood bag 55, by the flow of blood from first chamber 944, through first outlet port 911. This assures that filter elements 83, 82, 81, and 80 will completely wet, and that all of the air that was in through slot 906, second chamber 947, filter elements 83, 82, 81, and 80, first chamber 944, first outlet port 911, and the interior of outlet tubing 53 will be forced into receiving blood bag 55. Because there is no siphon tube in first chamber 944, all of the air will be purged from within the filter device by the positive pressure within the filter device, and by the flow of blood through the filter device created by the positive pressure in second chamber 947. The initial air in second chamber 947a, filter elements 83a, 82a, 81a, 80a, and first chamber 945 will be purged as just described.

Blood filtration will continue until feed blood bag 54 is empty. When feed blood bag 54 is empty it will be collapsed and therefore close the inlet end of inlet tubing 52. Because outlet tubing 53 will be full of blood, and because the outside of receiving blood bag 55 is at atmospheric pressure, the pressure head in first outlet port 911, first chamber 944, second outlet port 911a, and first chamber 945, will be negative. Once blood flow has stopped the pressure drop across filter elements 83, 82, 81, and 80, will fall to zero. The pressure drop across filter elements 83a, 82a, 81a, and 80a, will also fall to zero. Hence the pressure in second chamber 947 and second chamber 947a will become negative. The pressure in through slot 906, inlet port 909, and inlet tubing 52 will also be negative. If a means (not shown) is provided to allow sterile air to enter inlet tubing 52 after filtration is complete, the portion of inlet tubing below the point of sterile air entry, along with inlet port 909, through slot 906, second chamber 947, and second chamber 947a will drain until second chamber 947 and second chamber 947a are empty, and blood will remain in filter elements 83, 82, 81, 80, 83a, 82a, 81a, and 80a, first chamber 944, first chamber 945, first outlet port 911, second outlet port 911a, and in outlet tubing 53. If a means is not provided to allow sterile air to enter inlet tubing 52 after filtration is complete, blood will remain in inlet tubing 52, inlet port 909, through slot 906, second chamber 947, second chamber 947a, filter elements 83, 82, 81, 80, 83a, 82a, 81a, and 80a, first chamber 944, first chamber 945, first outlet port 911, second outlet port 911a, and in outlet tubing 53.

The user can now close tube clamp 75 on outlet tubing 53 and then seal outlet tubing 53 above tube clamp 75, and then cut outlet tubing 53 above the seal just made. Feed blood bag 54, inlet tubing 52, and filter device 940 can now be discarded in a safe manner. Outlet tubing 53 will have segments marked on it. The user can now seal the outlet tubing at the segment marks. The blood that is left in outlet tubing 53 will be used for cross matching and for quality control purposes.

Although the present invention has been shown and described in terms of specific preferred embodiments, it will be appreciated by those skilled in the art that changes or modifications are possible which do not depart from the inventive concepts described and taught herein. Such changes and modifications are deemed to fall within the purview of these inventive concepts. In addition it is contemplated that the filter assembly may be employed in an environment other than blood filtration. A fluid system in which components of the fluid must be removed can benefit from the use of a filter apparatus embodying the teachings of the present invention.

What is claimed is:

1. A filter device for filtering blood or blood product to remove components of the blood or blood product from the blood or blood product comprising:

a body having a partition wall fixed to the inner periphery of said body, said partition wall dividing said body into a first filter well on the first side of said partition wall, and a second filter well on the second side of said partition wall, a first filtration media having a first surface and a second surface, comprised of at least one filter element disposed within and sealed to said first filter well to prevent bypass around said first filtration media, with the outer edge of all of the filter elements of said first filtration media disposed below the top of said first filter well, a second filtration media having a first surface and a second surface, comprised of at least one filter element disposed within and sealed to said second filter well to prevent bypass around said second filtration media, with the outer edge of all of the filter elements of said second filtration media disposed below the top of said second filter well, a first chamber located between the first surface of said first filtration media and the first side of said partition wall, a second chamber located between the first surface of said second filtration media and the second side of said partition wall, with said partition wall containing a through slot, with said through slot being in fluid flow communication with said first chamber, and in fluid flow communication with said second chamber, an first port leading outside of said device in fluid flow communication with said through slot, a front cover, sealed with a first seal to the outer periphery of said first filter well, a back cover, sealed with a second seal to the outer periphery of said second filter well, a third chamber located between the second surface of said first filtration media and the inside wall side of said front cover, a fourth chamber located between the second surface of said second filtration media and the inside wall side of said back cover, a second port leading outside of said device in fluid flow communication with said third chamber, a third port leading outside of said device in fluid flow communication with said fourth chamber.

2. The filter device of claim 1 wherein said first port is an inlet port, and wherein said second port is a first outlet port, and wherein said third port is a second outlet port.

3. The filter device of claim 1 wherein said first port is an outlet port, and wherein said second port is a first inlet port, and wherein said third port is a second inlet port.

4. The filter device of claim 1 wherein the shape of the outer edge of said first filtration media is the same as the shape of the side wall of said first filter well, thereby providing a means to seal said first filtration media to said first filter well with a compression fit between the outer edge of said first filtration media and the side wall of said first filter well, and wherein the shape of the outer edge of said second filtration media is the same as the shape of the side wall of said second filter well, thereby providing a means to seal said second filtration media to said second filter well with a compression fit between the outer edge of said second filtration media and the side wall of said second filter well.

5. The filter device of claim 4 wherein a first filter compression ring is inserted into said first filter well, and wherein the outer periphery of the second surface of said first filtration media is compressed by said first filter compression ring, thereby sealing the second surface of said first filtration media to said first filter well, and wherein a second filter compression ring is inserted into said second filter well, and wherein the outer periphery of the second surface of said second filtration media is compressed by said second filter compression ring, thereby sealing the second surface of said second filtration media to said second filter well.

6. The filter device of claim 1 wherein said first and said second filtration media are capable of removing leukocytes from blood or blood product.

7. A filter device for filtering blood or blood product to remove components of the blood or blood product from the blood or blood product comprising:
   a body having a partition wall that includes a first surface on one side of said partition wall and a second surface on the other side of said partition wall, with said partition wall fixed to the inner periphery of said body, said partition wall dividing said body into a first filter well on the first surface side of said partition wall, and a second filter well on the second surface side of said partition wall,
   a first filtration media including a first surface and a second surface with said first filtration media disposed within and sealed to said first filter well to prevent bypass around said first filtration media, with the outer edge of said first filtration media disposed below the top of said first filter well, with the shape of the outer edge of said first filtration media being the same as the shape of the side wall of said first filter well, thereby providing a means to seal said first filtration media to said first filter well with a compression fit between the entire outer edge of said first filtration media and the side wall of said first filter well,
   a second filtration media including a first surface and a second surface, with said second filtration media disposed within and sealed to said second filter well to prevent bypass around said second filtration media, with the outer edge of said second filtration media disposed below the top of said second filter well, with the shape of the outer edge of said second filtration media being the same as the shape of the side wall of said second filter well, thereby providing a means to seal said second filtration media to said second filter well with a compression fit between the entire outer edge of said second filtration media and the side wall of said second filter well,
   a first chamber located between said first surface of said partition wall and said first surface of said first filtration media,
   a second chamber located between said second surface of said partition wall and said first surface of said second filtration media,
   a cross port located on said body entirely outside of said first filter well and entirely outside of said second filter well,
   a front cover sealed with a first seal to said body, said first seal forming a single closed loop that encloses the outer periphery of said first filter well and a first end of said cross port, thereby creating a third chamber between the inner surface of said front cover and the second surface of said first filtration media, with the first end of said cross port in fluid flow communication with said third chamber,
   a back cover sealed with a second seal to said body, said second seal forming a single closed loop that encloses the outer periphery of said second filter well and a second end of said cross port, thereby creating a fourth chamber between the inner surface of said back cover and the second surface of said second filtration media, with the second end of said cross port in fluid flow communication with said fourth chamber,
   an first port leading outside of said device in fluid flow communication with said cross port,
   an second port leading outside of said device in fluid flow communication with said first chamber, and in fluid flow communication with said second chamber.

8. The filter device of claim 7 wherein said first port is an inlet port, and wherein said second port is an outlet port.

9. The filter device of claim 8 wherein said first port is located on said body.

10. The filter device of claim 8 wherein said first port is located on said front cover.

11. The filter device of claim 7 wherein said first port is an outlet port, and wherein said second port is an inlet port.

12. The filter device of claim 7 wherein said first filtration media includes one or more filter elements, and wherein at least one filter element of said first filtration media is sealed to the first filter well with a compression fit between the entire outer edge of said at least one filter element of said first filtration media and the side wall of the first filter well, and wherein said second filtration media includes one or more filter elements, and wherein at least one filter element of said second filtration media is sealed to the second filter well with a compression fit between the entire outer edge of said at least one filter element of said second filtration media and the side wall of the second filter well.

13. A method of filtering blood or blood product to remove components of the blood or blood product from the blood or blood product comprising:
   a) providing a filter device comprising:
      a body having a partition wall that includes a first surface on one side of said partition wall and a second surface on the other side of said partition wall, with said partition wall fixed to the inner periphery of said body, said partition wall dividing said body into a first filter well on the first surface side of said partition wall, and a second filter well on the second surface side of said partition wall,
      a first filtration media including a first surface and a second surface, with said first filtration media disposed within, and sealed to, said first filter well to prevent bypass around said first filtration media, with the outer edge of said first filtration media disposed below the top of said first filter well, with the shape of the outer edge of said first filtration media being the same as the shape of the side wall of said first filter well, thereby providing a means to seal said first filtration media to said first filter well with a compression fit between the entire outer edge of said first filtration media and the side wall of said first filter well,
      a second filtration media including a first surface and a second surface, with said second filtration media disposed within, and sealed to, said second filter well to prevent bypass around said second filtration media, with the outer edge of said second filtration media disposed below the top of said second filter well, with the shape of the outer edge of said second filtration media being the same as the shape of the side wall of said second filter well, thereby providing a means to seal said second filtration media to said second filter well with a compression fit between the entire outer edge of said second filtration media and the side wall of said second filter well,
      a first chamber located between said first surface of said partition wall and said first surface of said first filtration media, a second chamber located between said second surface of said partition wall and said first surface of said second filtration media, a cross port located on said body entirely outside of said first filter well and entirely outside of said second filter well, a front cover sealed with a first seal to said body, said first seal forming a single closed loop that encloses the outer periphery of said first filter well and a first end of said cross port, thereby creating a third chamber between the inner surface of said front cover and the second surface of said first filtration media, with the first end of said cross port in fluid flow communication with said third chamber, a back cover sealed with a second seal to said body, said second seal forming a single closed loop that encloses the outer periphery of said second filter well and a second end of said cross port, thereby creating a fourth chamber between the inner surface of said back cover and the second surface of said second filtration media, with the second end of said cross port in fluid flow communication with said fourth chamber, an first port leading outside of said device in fluid flow communication with said cross port, an second port leading outside of said device in fluid flow communication with said first chamber, and in fluid flow communication with said second chamber, b) flowing a first portion of the blood or blood product through a first fluid flow path between said first port and said second port, wherein the first fluid flow path includes flowing the blood or blood product through said first filtration media, c) flowing a second portion of the blood or blood product through a second fluid flow path between said first port and said second port, wherein the second fluid flow path includes flowing the blood or blood product through said second filtration media.

14. The method of claim 13 wherein said first port is an inlet port, and wherein said second port is an outlet port, and wherein said first fluid flow path flows from said inlet port, through said cross port, through said first filtration media, into said outlet port, and wherein said second fluid flow path flows from said inlet port, through said cross port, through said second filtration media, into said outlet port.

15. The method of claim 13 wherein said second port is an inlet port, and wherein said first port is an outlet port, and wherein said first fluid flow path flows from said inlet port, through said first filtration media, through said cross port into said outlet port, and wherein said second fluid flow path flows from said inlet port, through said second filtration media, through said cross port into said outlet port.

16. The filter device of claim 7 wherein the first end of said cross port is in direct fluid flow communication with said third chamber, and wherein the second end of said cross port in direct fluid flow communication with said fourth chamber.

17. The method of claim 13 wherein the first end of said cross port is in direct fluid flow communication with said third chamber, and wherein the second end of said cross port in direct fluid flow communication with said fourth chamber.

18. A filter device for filtering blood or blood product to remove components of the blood or blood product from the blood or blood product comprising:

a body having a partition wall that includes a first surface on one side of said partition wall and a second surface on the other side of said partition wall, with said partition wall fixed to the inner periphery of said body, said partition wall dividing said body into a first filter well on the first surface side of said partition wall, and a second filter well on the second surface side of said partition wall, a first filtration media including a first surface and a second surface with said first filtration media disposed within and sealed to said first filter well to prevent bypass around said first filtration media, with the outer edge of said first filtration media disposed below the top of said first filter well, with the shape of the outer edge of said first filtration media being the same as the shape of the side wall of said first filter well, thereby providing a means to seal said first filtration media to said first filter well with a compression fit between the outer edge of said first filtration media and the side wall of said first filter well, a second filtration media including a first surface and a second surface, with said second filtration media disposed within and sealed to said second filter well to prevent bypass around said second filtration media, with the outer edge of said second filtration media disposed below the top of said second filter well, with the shape of the outer edge of said second filtration media being the same as the shape of the side wall of said second filter well, thereby providing a means to seal said second filtration media to said second filter well with a compression fit between the outer edge of said second filtration media and the side wall of said second filter well, a first chamber located between said first surface of said partition wall and said first surface of said first filtration media, a second chamber located between said second surface of said partition wall and said first surface of said second filtration media, a cross port located on said body entirely outside of said first filter well and entirely outside of said second filter well, a front cover sealed with a first seal to said body, said first seal forming a single closed loop that encloses the outer periphery of said first filter well and a first end of said cross port, thereby creating a third chamber between the inner surface of said front cover and the second surface of said first filtration media, with the first end of said cross port in fluid flow communication with said third chamber, a back cover sealed with a second seal to said body, said second seal forming a single closed loop that encloses the outer periphery of said second filter well and a second end of said cross port, thereby creating a fourth chamber between the inner surface of said back cover and the second surface of said second filtration media, with the second end of said cross port in fluid flow communication with said fourth chamber, an first port leading outside of said device in fluid flow communication with said cross port, said first port being located on said front cover, an second port leading outside of said device in fluid flow communication with said first chamber, and in fluid flow communication with said second chamber.

19. A filter device for filtering blood or blood product to remove components of the blood or blood product from the blood or blood product comprising:

a body having a partition wall that includes a first surface on one side of said partition wall and a second surface on the other side of said partition wall, with said partition wall fixed to the inner periphery of said body, said partition wall dividing said body Into a first filter well on the first surface side of said partition wall, and a second filter well on the second surface side of said partition wall, a first filtration media including a first surface and a second surface with said first filtration media disposed within and sealed to said first filter well to prevent bypass around said first filtration media, with the outer edge of said first filtration media disposed below the top of said first filter well, with the shape of the outer edge of said first filtration media being the same as the shape of the side wall of said first filter well, thereby providing a means to seal said first filtration media to said first filter well with a compression fit between the outer edge of said first filtration media and the side wall of said first filter well, a second filtration media including a first surface and a second surface, with said second filtration media disposed within and sealed to said second filter well to prevent bypass around said second filtration media, with the outer edge of said second filtration media disposed below the top of said second filter well, with the shape of the outer edge of said second filtration media being the same as the shape of the side wall of said second filter well, thereby providing a means to seal said second filtration media to said second filter well with a compression fit between the outer edge of said second filtration media and the side wall of said second filter well, a first filter compression ring inserted into said first filter well, wherein the outer periphery of the second surface of said first filtration media is compressed by said first filter compression ring, thereby sealing the second surface of said first filtration media to said first filter well, and a second filter compression ring inserted into said second filter well, wherein the outer periphery of the second surface of said second filtration media is compressed by said second filter compression ring, thereby sealing the second surface of said second filtration media to said second filter well, a first chamber located between said first surface of said partition wall and said first surface of said first filtration media, a second chamber located between said second surface of said partition wall and said first surface of said second filtration media, a cross port located on said body entirely outside of said first filter well and entirely outside of said second filter well, a front cover sealed with a first seal to said body, said first seal forming a single closed loop that encloses the outer periphery of said first filter well and a first end of said cross port, thereby creating a third chamber between the inner surface of said front cover and the second surface of said first filtration media, with the first end of said cross port in fluid flow communication with said third chamber, a back cover sealed with a second seal to said body, said second seal forming a single closed loop that encloses the outer periphery of said second filter well and a second end of said cross port, thereby creating a fourth chamber between the inner surface of said back cover and the second surface of said second filtration media, with the second end of said cross port in fluid flow communication with said fourth chamber, a first port leading outside of said device in fluid flow communication with said cross port, a second port leading outside of said device in fluid flow communication with said first chamber, and in fluid flow communication with said second chamber.

20. The filter device of claim 19 wherein said first filter compression ring is an integral part of said front cover, and wherein said second filter compression ring is an integral part of said back cover.

21. A method of filtering blood or blood product to remove components of the blood or blood product from the blood or blood product comprising:

a) providing a filter device comprising:

a body having a partition wall fixed to the inner periphery of said body, said partition wall dividing said body into a first filter well on the first side of said partition wall, and a second filter well on the second side of said partition wall, a first filtration media having a first surface and a second surface, comprised of at least one filter element disposed within and sealed to said first filter well to prevent bypass around said first filtration media, with the outer edge of all of the filter elements of said first filtration media disposed below the top of said first filter well, a second filtration media having a first surface and a second surface, comprised of at least one filter element disposed within and sealed to said second filter well to prevent bypass around said second filtration media, with the outer edge of all of the filter elements of said second filtration media disposed below the top of said second filter well, a first chamber located between the first surface of said first filtration media and the first side of said partition wall, a second chamber located between the first surface of said second filtration media and the second side of said partition wall, with said partition wall containing a through slot, with said through slot being in fluid flow communication with said first chamber, and in fluid flow communication with said second chamber, an first port leading outside of said device in fluid flow communication with said through slot, a front cover, sealed with a first seal to the outer periphery of said first filter well, a back cover, sealed with a second seal to the outer periphery of said second filter well, a third chamber located between the second surface of said first filtration media and the inside wall side of said front cover, a fourth chamber located between the second surface of said second filtration media and the inside wall side of said back cover, a second port leading outside of said device in fluid flow communication with said third chamber, a third port leading outside of said device in fluid flow communication with said fourth chamber, b) flowing a first portion of the blood or blood product through a first fluid flow path between said first port and said second port, wherein the first fluid flow path includes flowing the blood or blood product through said first filtration media, c) flowing a second portion of the blood or blood product through a second fluid flow path between said first port and said third port, wherein the second fluid flow path includes flowing the blood or blood product through said second filtration media.

* * * * *